US007423128B2

(12) United States Patent
Gazit-Bornstein et al.

(10) Patent No.: US 7,423,128 B2
(45) Date of Patent: Sep. 9, 2008

(54) ANTI-PROPERDIN ANTIBODIES, AND METHODS FOR MAKING AND USING SAME

(75) Inventors: Gadi Gazit-Bornstein, Mountain View, CA (US); Giorgio Senaldi, Dublin, CA (US); Xiao-Dong Yang, Palo Alto, CA (US); Bruce Keyt, Hillsborough, CA (US); Gerardo Zapata, San Mateo, CA (US)

(73) Assignee: Amgen Fremont Inc., Fremont, CA (US)

( * ) Notice: Subject to any disclaimer, the term of this patent is extended or adjusted under 35 U.S.C. 154(b) by 462 days.

(21) Appl. No.: 10/981,300

(22) Filed: Nov. 3, 2004

(65) Prior Publication Data

US 2006/0093599 A1 May 4, 2006

(51) Int. Cl.
*C07K 16/18* (2006.01)
*C07K 16/40* (2006.01)

(52) U.S. Cl. .......................... 530/388.15; 530/388.25; 530/388.26; 530/391.3

(58) Field of Classification Search ............ 530/388.15, 530/388.25, 388.26, 391.3
See application file for complete search history.

(56) References Cited

U.S. PATENT DOCUMENTS

| | | | |
|---|---|---|---|
| 5,770,429 A | 6/1998 | Lonberg | |
| 5,861,156 A * | 1/1999 | George et al. ............ | 424/135.1 |
| 6,075,181 A | 6/2000 | Kucherlapati | |
| 6,114,598 A | 9/2000 | Kucherlapati | |
| 6,150,584 A | 11/2000 | Kucherlapati | |
| 6,162,963 A | 12/2000 | Kucherlapati | |
| 2002/0015701 A1 | 2/2002 | Gupta-Bansal et al. | |

OTHER PUBLICATIONS

Whiteman, Leslie Y. et al., "Association of Activated Properdin With Complexes of Properdin With C3," The Journal of Immunology, vol. 147, 1344-1351, No. 4, Aug. 15, 1991.
International Search Report for International Application No. PCT/US05/39628 dated Jul. 21, 2006.
Written Opinion of the International Searching Authority for International Application No. PCT/US05/39628 dated Jul. 21, 2006.
Green (1999) *J. Immunol. Methods* 231:11-23.
Wells (2000) *Chem Biol* 7:R185-6.
Davis et al. (1999) Cancer Metastasis Rev 18(4):421-5.
Vuagnat et al. (2000) *Mol. Immunol.* 37:467-478.
Perdikoulis et al. (2001) *Biochim. Biophys. Acta* 1548:265-277.
Gupta-Bansal et al. (2000) *Mol. Immunol.* 37:191-201.

* cited by examiner

*Primary Examiner*—David A. Saunders
*Assistant Examiner*—F. Pierre VanderVegt
(74) *Attorney, Agent, or Firm*—Knobbe Martens Olson & Bear LLP

(57) ABSTRACT

The present invention is related to antibodies directed to the antigen properdin and uses of such antibodies. In particular, in accordance with the present invention, there are provided fully human monoclonal antibodies directed to the antigen properdin. Nucleotide sequences encoding, and polypeptides comprising, heavy and light chain immunoglobulin molecules, particularly sequences corresponding to contiguous heavy and light chain sequences spanning the framework regions and/or complementarity determining regions (CDR's), specifically from FR1 through FR4 or CDR1 through CDR3, are provided. Hybridomas or other cell lines expressing such immunoglobulin molecules and monoclonal antibodies are also provided.

34 Claims, 24 Drawing Sheets

| Ab No | Chain Name | V | J | FR1 |
|---|---|---|---|---|
| GL | | | | |
| GL | | | | DIQMTQSPSSLSASVGDRVTITC |
| 1 | GL001H1_12_1_1N1K | A20 | JK1 | ----------------------- |
| 2 | GL001H1_6_2_1N1K | " | " | ----------------------S-- |
| GL | | | | DIQMTQSPSSLSASVGDRVTITC |
| 3 | GL001H8_14_1N1K | O12 | JK4 | ----------------------- |
| GL | | | | DIQMTQSPSSVSASVGDRVTITC |
| 4 | GL001H8_7_1N1K | L5 | JK1 | ----------------------- |
| GL | | | | DIQMTQSPSSLSASVGDRVTITC |
| 5 | GL001H8_11_1N1K | O18 | JK4 | ----------------------- |

| Ab No | CDR1 | FR2 | CDR2 |
|---|---|---|---|
| GL | RASQGISNYLA | WYQQKPGKVPKLLIY | AASTLQS |
| 1 | ----------- | --------------- | ------- |
| 2 | ----D------ | --------------- | ------- |
| GL | RASQSISSYLN | WYQQKPGKAPKLLIY | AASSLQS |
| 3 | ----N---F-- | -----S--------F | -T-R--- |
| GL | RASQGISSWLA | WYQQKPGKAPKLLIY | AASSLQS |
| 4 | ----------- | --------------- | V------ |
| GL | QASQDISNYLN | WYQQKPGKAPKLLIY | DASNLET |
| 5 | ----------- | --------------- | ---T--- |

| Ab No | FR3 | CDR3 | J | SEQ ID NO |
|---|---|---|---|---|
| GL | GVPSRFSGSGSGTDFTLTISSLQPEDVATYYC | QKYNSAPWT | FGQGTKVEIKR | 21 |
| 1 | ------------------------------- | ---D----- | ----------- | 22 |
| 2 | ------------------------------- | --------- | ----------- | 23 |
| GL | GVPSRFSGSGSGTDFTLTISSLQPEDFATYYC | QQSYS###T | FGGGTKVEIKR | 24 |
| 3 | ------I--------------G--------F-- | -----IPL- | -------D--- | 25 |
| GL | GVPSRFSGSGSGTDFTLTISSLQPEDFATYYC | QQANSF##T | FGQGTKVEIKR | 26 |
| 4 | ------------------------I----- | ---D--PR- | ----------- | 27 |
| GL | GVPSRFSGSGSGTDFTFTISSLQPEDIATYYC | QQYDNLPLT | FGGGTKVEIKR | 28 |
| 5 | ------------------------------- | -N------- | ----------- | 29 |

FIG. 12

| Ab No | Clone | VL | V Sequence | #N's | N | JL |
|---|---|---|---|---|---|---|
| 1 | GL001H1_12_1_1N1K | A20 (1-284) | TGCCCC | 0 | | JK1 (285-322) |
| 2 | GL001H1_6_2_1N1K | A20 (1-284) | TGCCCC | 0 | | JK1 (285-322) |
| 3 | GL001H8_14_1N1K | O12 (1-280) | ACAGTA | 6 | TTCCAC | JK4 (287-322) |
| 4 | GL001H8_11_1N1K | O18 (46-331) | TCCCTC | 0 | | JK4 (332-367) |
| 5 | GL001H8_7_1N1K | L5 (1-284) | TTTCCC | 2 | CC | JK1 (287-322) |

| Ab No | J Sequence | Constant Region | CDR1 | CDR2 | CDR3 | CDR1 AA Seq |
|---|---|---|---|---|---|---|
| 1 | GTGGAC | IGKC (323-642) | 70-102 | 148-168 | 265-291 | RASQGISNYLA (SEQ ID NO:30) |
| 2 | GTGGAC | IGKC (323-642) | 70-102 | 148-168 | 265-291 | RASQDISNYLA (SEQ ID NO:31) |
| 3 | TCACTT | IGKC (323-462) | 70-102 | 148-168 | 265-291 | RASQNISSFLN (SEQ ID NO:32) |
| 4 | TCACTT | IGKC (368-514) | 115-147 | 193-213 | 310-336 | QASQDISNYLN (SEQ ID NO:33) |
| 5 | GGACGT | IGKC (323-462) | 70-102 | 148-168 | 265-291 | RASQGISSWLA (SEQ ID NO:34) |

| Ab No | CDR2 AA Seq | CDR3 AA Seq |
|---|---|---|
| 1 | AASTLQS (SEQ ID NO:35) | QKYDSAPWT (SEQ ID NO:40) |
| 2 | AASTLQS (SEQ ID NO:36) | QKYNSAPWT (SEQ ID NO:41) |
| 3 | ATSRLQS (SEQ ID NO:37) | QQSYSIPLT (SEQ ID NO:42) |
| 4 | DASTLET (SEQ ID NO:38) | QNYDNLPLT (SEQ ID NO:43) |
| 5 | VASSLQS (SEQ ID NO:39) | QQADSFPRT (SEQ ID NO:44) |

| | Chain Name | V | D |
|---|---|---|---|
| GL 3 | GL001H8_14_1N1G4 | VH3-33 | D3-22 |
| GL 4 | GL001H8_11_1N1G2 | VH3-33 | D3-16 |
| GL 2 | GL001H1_6_2_1N1G2 | VH1-24 | D3-9 |
| GL 5 | GL001H8_7_1N1G4 | VH4-31 | D7-27 |
| GL 1 | GL001H1_12_1_1N1G2 | VH4-59 | D1-7 |

| Ab No | J | FR1 | CDR1 |
|---|---|---|---|
| GL | | QVQLVESGGGVVQPGRSLRLSCAAS | GFTFSSYGMH |
| 3 | JH6B | ###QEQ------------------- | -----N--I- |
| GL | | QVQLVESGGGVVQPGRSLRLSCAAS | GFTFSSYGMH |
| 4 | JH6B | ------------------------- | -----C---- |
| GL | | QVQLVQSGAEVKKPGASVKVSCKVS | GYTLTELSMH |
| 2 | JH6B | ------------------------- | ---------- |
| GL | | QVQLQESGPGLVKPSQTLSLTCTVS | GGSISSGGYYWS |
| 5 | JH4B | ----EQ------------------- | -D------H--- |
| GL | | QVQLQESGPGLVKPSETLSLTCTVS | GGSISSYYWS |
| 1 | JH3B | ------------------------- | -----I---- |

| Ab No | FR2 | CDR2 | FR3 |
|---|---|---|---|
| GL | WVRQAPGKGLEWVA | VIWYDGSNKYYADSVKG | RFTISRDNSKNTLYLQMNSLRAEDTAVYYCAR |
| 3 | -------------- | ------N---------- | -------------------------------- |
| GL | WVRQAPGKGLEWVA | VIWYDGSNKYYADSVKG | RFTISRDNSKNTLYLQMNSLRAEDTAVYYC#G |
| 4 | -------------- | ----------------- | ------------------------------A- |
| GL | WVRQAPGKGLEWMG | GFDPEDGETIYAQKFQG | RVTMTEDTSTDTAYMELSSLRSEDTAVYYCA# |
| 2 | -------------- | ------------M--- | ---------------D--------------T |
| GL | WIRQHPGKGLEWIG | YIYYSGSTYYNPSLKS | RVTISVDTSKNQFSLKLSSVTAADTAVYYCAR |
| 5 | -------------- | -------S-------- | -F--------------T--------------- |
| GL | WIRQPPGKGLEWIG | YIYYSGSTNYNPSLKS | RVTISVDTSKNQFSLKLSSVTAADTAVYYCA# |
| 1 | -------------- | ---------------- | -------------------------------V |

| Ab No | CDR3 | J | SEQ ID NO: |
|---|---|---|---|
| GL | ##YYDSSGYY##YYYYGMDV | WGQGTTVTVSSA | 45 |
| 3 | GG----R---TP-------- | ------------ | 46 |
| GL | G###MDV | WGQGTTVTVSSA | 47 |
| 4 | -ATA--- | ------------ | 48 |
| GL | ##YYDILTG##YYYYGMDV | WGQGTTVTVSSA | 49 |
| 2 | GT-------PS-----LG- | ------------ | 50 |
| GL | TGDYFDY | WGQGTLVTVSSA | 51 |
| 5 | ------- | --L--------- | 52 |
| GL | WNY##AFDI | WGQGTMVTVSSA | 53 |
| 1 | ---GD---- | ------------ | 54 |

| Ab No | Clone | VH | V Sequence | #N's | N |
|---|---|---|---|---|---|
| 3 | GL001H8_14_1N1G4 | VH3-33 (1-286) | CGAGAG | 4 | GGGG |
| 4 | GL001H8_11_1N1G2 | VH3-33 (61-350) | CTGTGC | 1 | C |
| 2 | GL001H1_6_2_1N1G2 | VH1-24 (1-293) | TGCAAC | 6 | CGGAAC |
| 5 | GL001H8_7_1N1G4 | VH4-31 (1-297) | GCGAGA | 0 | |
| 1 | GL001H1_12_1_1N1G2 | VH4-59 (1-288) | TGTGCG | 3 | GTT |

| Ab No | D1 | D1 Sequence | #N's | N | D2 | D2 Sequence |
|---|---|---|---|---|---|---|
| 3 | D3-22 (291-315) | TTACTATGATAGTCGTGGTTATTAC (SEQ ID NO:55) | -N.A- | -N.A- | -N.A- | -N.A- |
| 4 | D3-16 (352-358) | GGGGGAG | -N.A- | -N.A- | -N.A- | -N.A- |
| 2 | D3-9 (300-321) | GTATTACGATATTTTGACTGGT (SEQ ID NO:56) | -N.A- | -N.A- | -N.A- | -N.A- |
| 5 | D7-27 (298-304) | ACTGGGG | -N.A- | -N.A- | -N.A- | -N.A- |
| 1 | D1-7 (292-300) | TGGAACTAC | -N.A- | -N.A- | -N.A- | -N.A- |

| Ab No | #N's | N | JH | J Sequence | Constant Region | CDR1 |
|---|---|---|---|---|---|---|
| 3 | 5 | ACCCC | JH6B (321-379) | CTACTA | IGHG4 (380-565) | 67-96 |
| 4 | 8 | CTACGGCC | JH6B (367-409) | ATGGAC | IGHG1 (410-425) | 136-165 |
| 2 | 5 | CCCTC | JH6B (327-385) | CTACTA | IGHG2 (386-1362) | 76-105 |
| 5 | 0 | | JH4B (305-352) | ACTACT | IGHG4 (353-541) | 76-111 |
| 1 | 4 | GGGG | JH3B (305-352) | ATGCTT | IGHG2 (353-1329) | 76-105 |

| Ab No | CDR2 | CDR3 | CDR1 AA Seq | CDR2 AA Seq |
|---|---|---|---|---|
| 3 | 139-189 | 286-345 | GFTFSNYGIH (SEQ ID NO:57) | VIWYDGNNKYYADSVKG (SEQ ID NO:62) |
| 4 | 208-258 | 355-375 | GFTFSCYGMH (SEQ ID NO:58) | VIWYDGSNKYYADSVKG (SEQ ID NO:63) |
| 2 | 148-198 | 295-351 | GYTLTELSMH (SEQ ID NO:59) | GFDPEDGETIYAQMFQG (SEQ ID NO:64) |
| 5 | 154-201 | 298-318 | GDSISSGGHYWS (SEQ ID NO:60) | YIYYSGSSYYNPSLKS (SEQ ID NO:65) |
| 1 | 148-195 | 292-318 | GGSISIYYWS (SEQ ID NO:61) | YIYYSGSTNYNPSLKS (SEQ ID NO:66) |

| Ab No | CDR3 AA Seq |
|---|---|
| 3 | GGYYDSRGYYTPYYYYGMDV (SEQ ID NO:67) |
| 4 | GATAMDV (SEQ ID NO:68) |
| 2 | GTYYDILTGPSYYYYGLGV (SEQ ID NO:69) |
| 5 | TGDYFDY (SEQ ID NO:70) |
| 1 | WNYGDAFDI (SEQ ID NO:71) |

> GL001H8_7_1N1k
GACATCCAGATGACCCAGTCTCCATCTTCCGTGTCTGCAT
CTGTAGGAGACAGAGTCACCATCACTTGTCGGGCGAGTCA
GGGTATTAGCAGTTGGTTAGCCTGGTATCAGCAGAAACCA
GGGAAAGCCCCTAAGCTCCTGATCTATGTTGCATCCAGTT
TACAAAGTGGAGTCCCATCAAGGTTCAGCGGCAGTGGATC
TGGGACAGATTTCACTCTCACCATCAGCAGCCTGCAGCCT
GAAGATATTGCAACTTACTATTGTCAACAGGCTGACAGTT
TCCCCCGGACGTTCGGCCAAGGGACCAAGGTGGAAATCAA
ACGAACTGTGGCTGCACCATCTGTCTTCATCTTCCCGCCA
TCTGATGAGCAGTTGAAATCTGGAACTGCCTGTGTTGTGT
GCCTGCTGAATAACTTCTATCCCAGAGAGGCCAAAGTACA
GTGGAAGGTGGATAACGCCCTCACA (SEQ ID NO:01)

> GL001H8_7_1N1G4.txt
CAGGTGCAGCTGGAGCAGTCGGGCCCAGGACTGGTGAAGC
CTTCACAGACCCTGTCCCTCACCTGCACTGTCTCTGGTGA
CTCCATCAGCAGTGGTGGTCACTACTGGAGCTGGATCCGC
CAGCACCCAGGGAAGGGCCTGGAGTGGATTGGGTACATCT
ATTACAGTGGGAGTTCCTACTACAACCCGTCCCTCAAGAG
TCGATTTACCATATCAGTCGACACGTCTAAGAACCAGTTC
TCCCTGAAGCTGACCTCTGTGACTGCCGCGGACACGGCCG
TGTATTATTGTGCGAGAACTGGGGACTACTTTGACTACTG
GGGCCTGGGAACCCTGGTCACCGTCTCCTCAGCTTCCACC
AAGGGCCCATCCGTCTTCCCCCTGGCGCCCTGCTCCAGGA
GCACCTCCGAGAGCACAGCCGCCCTGGGCTGCCTGGTCAA
GGACTACTTCCCCGAACCGGTGACGGTGTCGTGGAACTCA
GGCGCCCTGACCAGCGGCGTGCACACCTTCCCGGCTGTCC
TACAGTCCTCAGGACTCTACT (SEQ ID NO:03)

> GL001H8_14_1N1K
GACATCCAGATGACCCAGTCTCCATCCTCCCTGTCTGCAT
CTGTAGGAGACAGAGTCACCATCACTTGCCGGGCAAGTCA
GAACATTAGCAGTTTTTTAAATTGGTATCAGCAGAAATCA
GGGAAAGCCCCTAAGCTCCTGATCTTTGCTACATCCCGTT
TACAAAGTGGGGTCCCATCAAGGATCAGTGGCAGTGGATC
TGGGACAGATTTCACTCTCACCATCAGCGGTCTGCAACCT
GAAGATTTTGCGACTTCTACTGTCAACAGAGTTACAGTA
TTCCACTCACTTTCGGCGGAGGGACCAAGGTGGACATCAA
ACGAACTGTGGCTGCACCATCTGTCTTCATCTTCCCGCCA
TCTGATGAGCAGTTGAAATCTGGAACTGCCTCTGTTGTGT
GCCTGCTGAATAACTTCTATCCCAGAGAGGCCAAAGTACA
GTGGAAGGTGGATAACGCCCTCA (SEQ ID NO:05)

FIG. 16B

> GL001H8_14_1N1G4.txt
CAGGAGCAGTCTGGGGGAGGCGTGGTCCAGCCTGGGAGGT
CCCTGAGACTCTCCTGTGCAGCGTCTGGATTCACCTTCAG
TAACTATGGCATACACTGGGTCCGCCAGGCTCCAGGCAAG
GGGCTGGAGTGGGTGGCAGTTATATGGTATGATGGAAATA
ATAAATACTATGCAGACTCCGTGAAGGGCCGATTCACCAT
CTCCAGAGACAATTCCAAGAACACGCTGTATCTGCAAATG
AACAGCCTGAGAGCCGAGGACACGGCTGTGTATTACTGTG
CGAGAGGGGGTTACTATGATAGTCGTGGTTATTACACCCC
CTACTACTACTACGGTATGGACGTCTGGGGCCAAGGGACC
ACGGTCACCGTCTCCTCAGCTTCCACCAAGGGCCCATCCG
TCTTCCCCCTGGCGCCCTGCTCCAGGAGCACCTCCGAGAG
CACAGCCGCCCTGGGCTGCCTGGTCAAGGACTACTTCCCC
GAACCGGTGACGGTGTCGTGGAACTCAGGCGCCCTGACCA
GCGGCGTGCACACCTTCCCGGCTGTCCTACAGTCCTCAGG
ACTCTCTC (SEQ ID NO:07)

> GL001H8_11_1N1K.txt
CAGCTCCTGGGGCTCCTGCTGCTCTGGCTCTCAGGTGCCA
GATGTGACATCCAGATGACCCAGTCTCCATCCTCCCTGTC
TGCATCTGTAGGAGACAGAGTCACCATCACTTGCCAGGCG
AGTCAGGACATTAGCAACTATTTAAATTGGTATCAGCAGA
AACCAGGGAAAGCCCCTAAGCTCCTGATCTACGATGCATC
CACTTTGGAAACAGGGGTCCCATCAAGGTTCAGTGGAAGT
GGATCTGGGACAGATTTTACTTTCACCATCAGCAGCCTGC
AGCCTGAAGATATTGCAACATATTACTGTCAAAACTATGA
TAATCTCCCTCTCACTTTCGGCGGAGGGACCAAGGTGGAG
ATCAAACGAACTGTGGCTGCACCATCTGTCTTCATCTTCC
CGCCATCTGATGAGCAGTTGAAATCTGGAACTGCCTCTGT
TGTGTGCCTGCTGAATAACTTCTATCCCAGAGAGGCCAAA
GTACAGTGGAAGGTGGATAACGCCCTCCCAATCG (SEQ ID NO:09)

> GL001H8_11_1N1G2.txt
CCATGGAAGTTGGGGCTGAGCTGGGTTTTCCTCGTTGCTC
TTTTAAGAGGTGTCCAGTGTCAGGTGCAGCTGGTGGAGTC
TGGGGGAGGCGTGGTCCAGCCTGGGAGGTCCCTGAGACTC
TCCTGTGCAGCGTCTGGATTCACCTTCAGTTGCTATGGCA
TGCACTGGGTCCGCCAGGCTCCAGGCAAGGGGCTGGAGTG
GGTGGCAGTTATATGGTATGATGGAAGTAATAAATACTAT
GCAGACTCCGTGAAGGGCCGATTCACCATCTCCAGAGACA
ATTCCAAGAACACGCTGTATCTGCAAATGAACAGCCTGAG
AGCCGAGGACACGGCTGTATATTACTGTGCCGGGGGAGCT
ACGGCCATGGACGTCTGGGGCCAAGGGACCACGGTCACCG
TCTCCTCAGCCTCCACCAAGGGCCC (SEQ ID NO:11)

FIG. 16C

> GL001H1_6_2_1N1K
GACATCCAGATGACCCAGTCTCCATCCTCCCTGTCTGCAT
CTGTAGGAGACAGAGTCACCAGCACTTGCCGGGCGAGTCA
GGACATTAGCAATTATTTAGCCTGGTATCAGCAGAAACCA
GGGAAAGTTCCTAAGCTCCTGATCTATGCTGCATCCACTT
TGCAATCAGGGGTCCCATCTCGGTTCAGTGGCAGTGGATC
TGGGACAGATTTCACTCTCACCATCAGCAGCCTGCAGCCT
GAAGATGTTGCAACTTATTACTGTCAAAGTATAACAGTG
CCCCGTGGACGTTCGGCCAAGGGACCAAGGTGGAAATCAA
ACGAACTGTGGCTGCACCATCTGTCTTCATCTTCCCGCCA
TCTGATGAGCAGTTGAAATCTGGAACTGCCTCTGTTGTGT
GCCTGCTGAATAACTTCTATCCAGAGAGGCCAAAGTACA
GTGGAAGGTGGATAACGCCCTCCAATCGGGTAACTCCCAG
GAGAGTGTCACAGAGCAGGACAGCAAGGACAGCACCTACA
GCCTCAGCAGCACCCTGACGCTGAGCAAAGCAGACTACGA
GAAACACAAAGTCTACGCCTGCGAAGTCACCCATCAGGGC
CTGAGCTCGCCCGTCACAAAGAGCTTCAACAGGGGAGAGT
GT (SEQ ID NO:13)

FIG. 16D

> GL001H1_6_2_1N1G2
CAGGTCCAGCTGGTACAGTCGGGGGCTGAGGTGAAGAAGC
CTGGGGCCTCAGTGAAGGTCTCCTGCAAGGTTTCCGGATA
CACCCTCACTGAATTATCCATGCACTGGGTGCGACAGGCT
CCTGGAAAAGGGCTTGAGTGGATGGGAGGTTTTGATCCTG
AAGATGGTGAAACAATCTACGCACAGATGTTCCAGGGCAG
AGTCACCATGACCGAGGACACATCTACAGACACAGCCTAC
ATGGACCTGAGCAGCCTGAGATCTGAGGACACGGCCGTGT
ATTACTGTGCAACCGGAACGTATTACGATATTTTGACTGG
TCCCTCCTACTACTACGGTTTGGGCGTCTGGGGCCAA
GGGACCACGGTCACCGTCTCCTCAGCCTCCACCAAGGGCC
CATCGGTCTTCCCCCTGGCGCCCTGCTCCAGGAGCACCTC
CGAGAGCACAGCGGCCCTGGGCTGCCTGGTCAAGGACTAC
TTCCCCGAACCGGTGACGGTGTCGTGGAACTCAGGCGCTC
TGACCAGCGGCGTGCACACCTTCCCAGCTGTCCTACAGTC
CTCAGGACTCTACTCCCTCAGCAGCGTGGTGACCGTGCCC
TCCAGCAACTTCGGCACCCAGACCTACACCTGCAACGTAG
ATCACAAGCCCAGCAACACCAAGGTGGACAAGACAGTTGA
GCGCAAATGTTGTGTCGAGTGCCCACCGTGCCCAGCACCA
CCTGTGGCAGGACCGTCAGTCTTCCTCTTCCCCCCAAAAC
CCAAGGACACCCTCATGATCTCCCGGACCCCTGAGGTCAC
GTGCGTGGTGGTGGACGTGAGCCACGAAGACCCCGAGGTC
CAGTTCAACTGGTACGTGGACGGCGTGGAGGTGCATAATG
CCAAGACAAAGCCACGGGAGGAGCAGTTCAACAGCACGTT
CCGTGTGGTCAGCGTCCTCACCGTTGTGCACCAGGACTGG
CTGAACGGCAAGGAGTACAAGTGCAAGGTCTCCAACAAAG
GCCTCCCAGCCCCCATCGAGAAAACCATCTCCAAAACCAA
AGGGCAGCCCCGAGAACCACAGGTGTACACCCTGCCCCCA
TCCCGGGAGGAGATGACCAAGAACCAGGTCAGCCTGACCT
GCCTGGTCAAAGGCTTCTACCCCAGCGACATCGCCGTGGA
GTGGGAGAGCAATGGGCAGCCGGAGAACAACTACAAGACC
ACACCTCCCATGCTGGACTCCGACGGCTCCTTCTTCCTCT
ACAGCAAGCTCACCGTGGACAAGAGCAGGTGGCAGCAGGG
GAACGTCTTCTCATGCTCCGTGATGCATGAGGCTCTGCAC
AACCACTACACGCAGAAGAGCCTCTCCCTGTCTCCGGGTA
AA (SEQ ID NO:15)

FIG. 16E

> GL001H1_12_1_1N1K
GACATCCAGATGACCCAGTCTCCATCCTCCCTGTCTGCAT
CTGTAGGAGACAGAGTCACCATCACTTGCCGGGCGAGTCA
GGGCATTAGCAATTATTTAGCCTGGTATCAGCAGAAACCA
GGGAAAGTTCCTAAGCTCCTGATCTATGCTGCATCCACTT
TGCAATCAGGGGTCCCATCTCGGTTCAGTGGCAGTGGATC
TGGGACAGATTTCACTCTCACCATCAGCAGCCTGCAGCCT
GAAGATGTTGCAACTTATTACTGTCAAAGTATGACAGTG
CCCCGTGGACGTTCGGCCAAGGGACCAAGGTGGAAATCAA
ACGAACTGTGGCTGCACCATCTGTCTTCATCTTCCCGCCA
TCTGATGAGCAGTTGAAATCTGGAACTGCCTCTGTTGTGT
GCCTGCTGAATAACTTCTATCCCAGAGAGGCCAAAGTACA
GTGGAAGGTGGATAACGCCCTCCAATCGGGTAACTCCAG
GAGAGTGTCACAGAGCAGGACAGCAAGGACAGCACCTACA
GCCTCAGCAGCACCCTGACGCTGAGCAAAGCAGACTACGA
GAAACACAAAGTCTACGCCTGCGAAGTCACCCATCAGGGC
CTGAGCTCGCCCGTCACAAAGAGCTTCAACAGGGGAGAGT
GT (SEQ ID NO:17)

FIG. 16F

> GL001H1_12_1_1N1G2
CAGGTGCAGCTGCAGGAGTCGGGCCCAGGACTGGTGAAGC
CTTCGGAGACCCTGTCCCTCACCTGCACTGTCTCTGGTGG
CTCCATCAGTATTTACTACTGGAGCTGGATCCGGCAGCCC
CCAGGGAAGGGACTGGAGTGGATTGGGTATATCTATTACA
GTGGGAGCACCAACTACAACCCCTCCCTCAAGAGTCGAGT
CACCATATCAGTAGACACGTCCAAGAACCAGTTCTCCCTG
AAGCTGAGCTCTGTGACCGCTGCGGACACGGCCGTGTATT
ACTGTGCGGTTTGGAACTACGGGGATGCTTTTGATATCTG
GGGCCAAGGGACAATGGTCACCGTCTCTTCAGCCTCCACC
AAGGGCCCATCGGTCTTCCCCCTGGCGCCCTGCTCCAGGA
GCACCTCCGAGAGCACAGCGGCCCTGGGCTGCCTGGTCAA
GGACTACTTCCCCGAACCGGTGACGGTGTCGTGGAACTCA
GGCGCTCTGACCAGCGGCGTGCACACCTTCCAGCTGTCC
TACAGTCCTCAGGACTCTACTCCCTCAGCAGCGTGGTGAC
CGTGCCCTCCAGCAACTTCGGCACCCAGACCTACACCTGC
AACGTAGATCACAAGCCCAGCAACACCAAGGTGGACAAGA
CAGTTGAGCGCAAATGTTGTGTCGAGTGCCCACCGTGCCC
AGCACCACCTGTGGCAGGACCGTCAGTCTTCCTCTTCCCC
CCAAAACCCAAGGACACCCTCATGATCTCCCGGACCCCTG
AGGTCACGTGCGTGGTGGTGGACGTGAGCCACGAAGACCC
CGAGGTCCAGTTCAACTGGTACGTGGACGGCGTGGAGGTG
CATAATGCCAAGACAAAGCCACGGGAGGAGCAGTTCAACA
GCACGTTCCGTGTGGTCAGCGTCCTCACCGTTGTGCACCA
GGACTGGCTGAACGGCAAGGAGTACAAGTGCAAGGTCTCC
AACAAAGGCCTCCCAGCCCCCATCGAGAAAACCATCTCCA
AAACCAAAGGGCAGCCCCGAGAACCACAGGTGTACACCCT
GCCCCCATCCCGGGAGGAGATGACCAAGAACCAGGTCAGC
CTGACCTGCCTGGTCAAAGGCTTCTACCCCAGCGACATCG
CCGTGGAGTGGGAGAGCAATGGGCAGCCGGAGAACAACTA
CAAGACCACACCTCCCATGCTGGACTCCGACGGCTCCTTC
TTCCTCTACAGCAAGCTCACCGTGGACAAGAGCAGGTGGC
AGCAGGGGAACGTCTTCTCATGCTCCGTGATGCATGAGGC
TCTGCACAACCACTACACGCAGAAGAGCCTCTCCCTGTCT
CCGGGTAAAA (SEQ ID NO:19)

FIG. 17A

\> GL001H8_7_1N1k
DIQMTQSPSSVSASVGDRVTITCRASQGIS
SWLAWYQQKPGKAPKLLIYVASSLQSGVPS
RFSGSGSGTDFTLTISSLQPEDIATYYCQQ
ADSFPRTFGQGTKVEIKRTVAAPSVFIFPP
SDEQLKSGTACVVCLLNNFYPREAKVQWKV
DNALT (SEQ ID NO:02)

\> GL001H8_7_1N1G4.txt
QVQLEQSGPGLVKPSQTLSLTCTVSGDSIS
SGGHYWSWIRQHPGKGLEWIGYIYYSGSSY
YNPSLKSRFTISVDTSKNQFSLKLTSVTAA
DTAVYYCARTGDYFDYWGLGTLVTVSSAST
KGPSVFPLAPCSRSTSESTAALGCLVKDYF
PEPVTVSWNSGALTSGVHTFPAVLQSSGLY
(SEQ ID NO:04)

\> GL001H8_14_1N1K
DIQMTQSPSSLSASVGDRVTITCRASQNIS
SFLNWYQQKSGKAPKLLIFATSRLQSGVPS
RISGSGSGTDFTLTISGLQPEDFATFYCQQ
SYSIPLTFGGGTKVDIKRTVAAPSVFIFPP
SDEQLKSGTASVVCLLNNFYPREAKVQWKV
DNAL (SEQ ID NO:06)

\> GL001H8_14_1N1G4.txt
QEQSGGGVVQPGRSLRLSCAASGFTFS
NYGIHWVRQAPGKGLEWVAVIWYDGNNKYY
ADSVKGRFTISRDNSKNTLYLQMNSLRAED
TAVYYCARGGYYDSRGYYTPYYYYGMDVWG
QGTTVTVSSASTKGPSVFPLAPCSRSTSES
TAALGCLVKDYFPEPVTVSWNSGALTSGVH
TFPAVLQSSGLS (SEQ ID NO:08)

\> GL001H8_11_1N1K.txt
QLLGLLLLWLSGARCDIQMTQSPSSLSASV
GDRVTITCQASQDISNYLNWYQQKPGKAPK
LLIYDASTLETGVPSRFSGSGSGTDFTFTI
SSLQPEDIATYYCQNYDNLPLTFGGGTKVE
IKRTVAAPSVFIFPPSDEQLKSGTASVVCL
LNNFYPREAKVQWKVDNALPI (SEQ ID NO:10)

FIG. 17B

> GL001H8_11_1N1G2.txt
PWKLGLSWVFLVALLRGVQCQVQLVESGGG
VVQPGRSLRLSCAASGFTFSCYGMHWVRQA
PGKGLEWVAVIWYDGSNKYYADSVKGRFTI
SRDNSKNTLYLQMNSLRAEDTAVYYCAGGA
TAMDVWGQGTTVTVSSASTKG (SEQ ID NO:12)

> GL001H1_6_2_1N1K
DIQMTQSPSSLSASVGDRVTSTCRASQDIS
NYLAWYQQKPGKVPKLLIYAASTLQSGVPS
RFSGSGSGTDFTLTISSLQPEDVATYYCQK
YNSAPWTFGQGTKVEIKRTVAAPSVFIFPP
SDEQLKSGTASVVCLLNNFYPREAKVQWKV
DNALQSGNSQESVTEQDSKDSTYSLSSTLT
LSKADYEKHKVYACEVTHQGLSSPVTKSFN
RGEC (SEQ ID NO:14)

> GL001H1_6_2_1N1G2
QVQLVQSGAEVKKPGASVKVSCKVSGYTLT
ELSMHWVRQAPGKGLEWMGGFDPEDGETIY
AQMFQGRVTMTEDTSTDTAYMDLSSLRSED
TAVYYCATGTYYDILTGPSYYYYGLGVWGQ
GTTVTVSSASTKGPSVFPLAPCSRSTSEST
AALGCLVKDYFPEPVTVSWNSGALTSGVHT
FPAVLQSSGLYSLSSVVTVPSSNFGTQTYT
CNVDHKPSNTKVDKTVERKCCVECPPCPAP
PVAGPSVFLFPPKPKDTLMISRTPEVTCVV
VDVSHEDPEVQFNWYVDGVEVHNAKTKPRE
EQFNSTFRVVSVLTVVHQDWLNGKEYKCKV
SNKGLPAPIEKTISKTKGQPREPQVYTLPP
SREEMTKNQVSLTCLVKGFYPSDIAVEWES
NGQPENNYKTTPPMLDSDGSFFLYSKLTVD
KSRWQQGNVFSCSVMHEALHNHYTQKSLSL
SPGK (SEQ ID NO:16)

> GL001H1_12_1_1N1K
DIQMTQSPSSLSASVGDRVTITCRASQGIS
NYLAWYQQKPGKVPKLLIYAASTLQSGVPS
RFSGSGSGTDFTLTISSLQPEDVATYYCQK
YDSAPWTFGQGTKVEIKRTVAAPSVFIFPP
SDEQLKSGTASVVCLLNNFYPREAKVQWKV
DNALQSGNSQESVTEQDSKDSTYSLSSTLT
LSKADYEKHKVYACEVTHQGLSSPVTKSFN
RGEC (SEQ ID NO:18)

FIG. 17C

> GL001H1_12_1_1N1G2
QVQLQESGPGLVKPSETLSLTCTVSGGSISI
YYWSWIRQPPGKGLEWIGYIYYSGSTNYNPS
LKSRVTISVDTSKNQFSLKLSSVTAADTAVY
YCAVWNYGDAFDIWGQGTMVTVSSASTKGPS
VFPLAPCSRSTSESTAALGCLVKDYFPEPVT
VSWNSGALTSGVHTFPAVLQSSGLYSLSSVV
TVPSSNFGTQTYTCNVDHKPSNTKVDKTVER
KCCVECPPCPAPPVAGPSVFLFPPKPKDTLM
ISRTPEVTCVVVDVSHEDPEVQFNWYVDGVE
VHNAKTKPREEQFNSTFRVVSVLTVVHQDWL
NGKEYKCKVSNKGLPAPIEKTISKTKGQPRE
PQVYTLPPSREEMTKNQVSLTCLVKGFYPSD
IAVEWESNGQPENNYKTTPPMLDSDGSFFLY
SKLTVDKSRWQQGNVFSCSVMHEALHNHYTQ
KSLSLSPGK (SEQ ID NO:20)

SEQUENCE LISTING

<160> NUMBER OF SEQ ID NOS: 71

<210> SEQ ID NO 1
<211> LENGTH: 465
<212> TYPE: DNA
<213> ORGANISM: homo sapien

<400> SEQUENCE: 1

```
gacatccaga tgacccagtc tccatcttcc gtgtctgcat ctgtaggaga cagagtcacc      60
atcacttgtc gggcgagtca gggtattagc agttggttag cctggtatca gcagaaacca     120
gggaaagccc ctaagctcct gatctatgtt gcatccagtt tacaaagtgg agtcccatca     180
aggttcagcg gcagtggatc tgggacagat ttcactctca ccatcagcag cctgcagcct     240
gaagatattg caacttacta ttgtcaacag gctgacagtt tcccccggac gttcggccaa     300
```

```
gggaccaagg tggaaatcaa acgaactgtg gctgcaccat ctgtcttcat cttcccgcca    360
tctgatgagc agttgaaatc tggaactgcc tgtgttgtgt gcctgctgaa taacttctat    420
cccagagagg ccaaagtaca gtggaaggtg ataacgccc tcaca                     465
```

<210> SEQ ID NO 2
<211> LENGTH: 155
<212> TYPE: PRT
<213> ORGANISM: homo sapien

<400> SEQUENCE: 2

```
Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Ile Ser Ser Trp
                20                  25                  30

Leu Ala Trp Tyr Gln Gln Lys Pro Gly Lys Ala Pro Lys Leu Leu Ile
         35                  40                  45

Tyr Val Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Ile Ala Thr Tyr Tyr Cys Gln Gln Ala Asp Ser Phe Pro Arg
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Cys Val Val Cys Leu Leu Asn Asn Phe Tyr Pro Arg Glu Ala
    130                 135                 140

Lys Val Gln Trp Lys Val Asp Asn Ala Leu Thr
145                 150                 155
```

<210> SEQ ID NO 3
<211> LENGTH: 541
<212> TYPE: DNA
<213> ORGANISM: homo sapien

<400> SEQUENCE: 3

```
caggtgcagc tggagcagtc gggcccagga ctggtgaagc cttcacagac cctgtccctc    60
acctgcactg tctctggtga ctccatcagc agtggtggtc actactggag ctggatccgc   120
cagcacccag gaagggcct ggagtggatt gggtacatct attacagtgg agttcctac    180 tacaacccgt ccctcaagag tcgatttacc atatcagtcg acacgtctaa gaaccagttc   240
tccctgaagc tgacctctgt gactgccgcg gacacggccg tgtattattg cgagaact    300 ggggactact ttgactactg gggcctggga accctggtca ccgtctcctc agcttccacc   360
aagggcccat ccgtcttccc cctggcgccc tgctccagga gcacctccga gagcacagcc   420
gccctgggct gcctggtcaa ggactacttc cccgaaccgg tgacggtgtc gtggaactca   480
ggcgccctga ccagcggcgt gcacaccttc ccggctgtcc tacagtcctc aggactctac   540
t                                                                   541
```

<210> SEQ ID NO 4
<211> LENGTH: 180
<212> TYPE: PRT
<213> ORGANISM: homo sapien

<400> SEQUENCE: 4

Gln Val Gln Leu Glu Gln Ser Gly Pro Gly Leu Val Lys Pro Ser Gln
1               5                   10                  15

Thr Leu Ser Leu Thr Cys Thr Val Ser Gly Asp Ser Ile Ser Ser Gly
            20                  25                  30

Gly His Tyr Trp Ser Trp Ile Arg Gln His Pro Gly Lys Gly Leu Glu
        35                  40                  45

Trp Ile Gly Tyr Ile Tyr Ser Gly Ser Ser Tyr Tyr Asn Pro Ser
    50                  55                  60

Leu Lys Ser Arg Phe Thr Ile Ser Val Asp Thr Ser Lys Asn Gln Phe
65                  70                  75                  80

Ser Leu Lys Leu Thr Ser Val Thr Ala Ala Asp Thr Ala Val Tyr Tyr
                85                  90                  95

Cys Ala Arg Thr Gly Asp Tyr Phe Asp Tyr Trp Gly Leu Gly Thr Leu
            100                 105                 110

Val Thr Val Ser Ser Ala Ser Thr Lys Gly Pro Ser Val Phe Pro Leu
            115                 120                 125

Ala Pro Cys Ser Arg Ser Thr Ser Glu Ser Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr
            180

<210> SEQ ID NO 5
<211> LENGTH: 463
<212> TYPE: DNA
<213> ORGANISM: homo sapien

<400> SEQUENCE: 5
gacatccaga tgacccagtc tccatcctcc ctgtctgcat ctgtaggaga cagagtcacc      60
atcacttgcc gggcaagtca gaacattagc agttttttaa attggtatca gcagaaatca     120
gggaaagccc ctaagctcct gatctttgct catcccgtt acaaagtgg ggtcccatca       180 aggatcagtg gcagtggatc tgggacagat ttcactctca ccatcagcgg tctgcaacct     240
gaagattttg cgactttcta ctgtcaacag agttacagta ttccactcac tttcggcgga    300
gggaccaagg tggacatcaa acgaactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tca                      463

<210> SEQ ID NO 6
<211> LENGTH: 154
<212> TYPE: PRT
<213> ORGANISM: homo sapien

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Ser Ser Phe
            20                  25                  30

Leu Asn Trp Tyr Gln Gln Lys Ser Gly Lys Ala Pro Lys Leu Leu Ile
        35                  40                  45

```
Phe Ala Thr Ser Arg Leu Gln Ser Gly Val Pro Ser Arg Ile Ser Gly
     50                  55                  60
Ser Gly Ser Gly Thr Asp Phe Thr Leu Thr Ile Ser Gly Leu Gln Pro
 65                  70                  75                  80
Glu Asp Phe Ala Thr Phe Tyr Cys Gln Gln Ser Tyr Ser Ile Pro Leu
                 85                  90                  95
Thr Phe Gly Gly Gly Thr Lys Val Asp Ile Lys Arg Thr Val Ala Ala
                100                 105                 110
Pro Ser Val Phe Ile Phe Pro Pro Ser Asp Glu Gln Leu Lys Ser Gly
            115                 120                 125
Thr Ala Ser Val Val Cys Leu Leu Asn Asn Phe Tyr Pro Arg Glu Ala
130                 135                 140
Lys Val Gln Trp Lys Val Asp Asn Ala Leu
145                 150
```

<210> SEQ ID NO 7
<211> LENGTH: 568
<212> TYPE: DNA
<213> ORGANISM: homo sapien

<400> SEQUENCE: 7

```
caggagcagt ctgggggagg cgtggtccag cctgggaggt ccctgagact ctcctgtgca      60
gcgtctggat tcaccttcag taactatggc atacactggg tccgccaggc tccaggcaag     120
gggctggagt gggtggcagt tatatggtat gatggaaata taaatacta tgcagactcc      180
gtgaagggcc gattcaccat ctccagagac aattccaaga cacgctgta tctgcaaatg      240
aacagcctga gagccgagga cacggctgtg tattactgtg cgagagggg ttactatgat      300
agtcgtggtt attacacccc ctactactac tacggtatgg acgtctgggg ccaagggacc     360
acggtcaccg tctcctcagc ttccaccaag ggcccatccg tcttccccct ggcgccctgc     420
tccaggagca cctccgagag cacagccgcc ctgggctgcc tggtcaagga ctacttcccc     480
gaaccggtga cggtgtcgtg gaactcaggc gccctgacca gcggcgtgca caccttcccg     540
gctgtcctac agtcctcagg actctctc                                         568
```

<210> SEQ ID NO 8
<211> LENGTH: 189
<212> TYPE: PRT
<213> ORGANISM: homo sapien

<400> SEQUENCE: 8

```
Gln Glu Gln Ser Gly Gly Gly Val Val Gln Pro Gly Arg Ser Leu Arg
  1               5                  10                  15
Leu Ser Cys Ala Ala Ser Gly Phe Thr Phe Ser Asn Tyr Gly Ile His
                 20                  25                  30
Trp Val Arg Gln Ala Pro Gly Lys Gly Leu Glu Trp Val Ala Val Ile
             35                  40                  45
Trp Tyr Asp Gly Asn Asn Lys Tyr Tyr Ala Asp Ser Val Lys Gly Arg
         50                  55                  60
Phe Thr Ile Ser Arg Asp Asn Ser Lys Asn Thr Leu Tyr Leu Gln Met
 65                  70                  75                  80
Asn Ser Leu Arg Ala Glu Asp Thr Ala Val Tyr Tyr Cys Ala Arg Gly
                 85                  90                  95
Gly Tyr Tyr Asp Ser Arg Gly Tyr Tyr Thr Pro Tyr Tyr Tyr Tyr Gly
                100                 105                 110
```

```
Met Asp Val Trp Gly Gln Gly Thr Thr Val Thr Val Ser Ser Ala Ser
        115                 120                 125

Thr Lys Gly Pro Ser Val Phe Pro Leu Ala Pro Cys Ser Arg Ser Thr
130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Ser
            180                 185

<210> SEQ ID NO 9
<211> LENGTH: 514
<212> TYPE: DNA
<213> ORGANISM: homo sapien

<400> SEQUENCE: 9
cagctcctgg ggctcctgct gctctggctc tcaggtgcca gatgtgacat ccagatgacc      60
cagtctccat cctccctgtc tgcatctgta ggagacagag tcaccatcac ttgccaggcg     120
agtcaggaca ttagcaacta tttaaattgg tatcagcaga accagggaa agcccctaag     180 ctcctgatct acgatgcatc cactttggaa acaggggtcc catcaaggtt cagtggaagt     240
ggatctggga cagattttac tttcaccatc agcagcctgc agcctgaaga tattgcaaca     300
tattactgtc aaaactatga taatctccct ctcactttcg gcggagggac caaggtggag     360
atcaaacgaa ctgtggctgc accatctgtc ttcatcttcc cgccatctga tgagcagttg     420
aaatctggaa ctgcctctgt tgtgtgcctg ctgaataact tctatcccag agaggccaaa     480
gtacagtgga aggtggataa cgccctccca atcg                                 514

<210> SEQ ID NO 10
<211> LENGTH: 171
<212> TYPE: PRT
<213> ORGANISM: homo sapien

<400> SEQUENCE: 10

Gln Leu Leu Gly Leu Leu Leu Trp Leu Ser Gly Ala Arg Cys Asp
 1               5                  10                  15

Ile Gln Met Thr Gln Ser Pro Ser Ser Leu Ser Ala Ser Val Gly Asp
            20                  25                  30

Arg Val Thr Ile Thr Cys Gln Ala Ser Gln Asp Ile Ser Asn Tyr Leu
        35                  40                  45

Asn Trp Tyr Gln Gln Lys Pro Gly Lys Ala Pro Lys Leu Leu Ile Tyr
    50                  55                  60

Asp Ala Ser Thr Leu Glu Thr Gly Val Pro Ser Arg Phe Ser Gly Ser
65                  70                  75                  80

Gly Ser Gly Thr Asp Phe Thr Phe Thr Ile Ser Ser Leu Gln Pro Glu
                85                  90                  95

Asp Ile Ala Thr Tyr Tyr Cys Gln Asn Tyr Asp Asn Leu Pro Leu Thr
            100                 105                 110

Phe Gly Gly Gly Thr Lys Val Glu Ile Lys Arg Thr Val Ala Ala Pro
        115                 120                 125

Ser Val Phe Ile Phe Pro Pro Ser Asp Glu Gln Leu Lys Ser Gly Thr
    130                 135                 140
```

```
Ala Ser Val Val Cys Leu Leu Asn Asn Phe Tyr Pro Arg Glu Ala Lys
145                 150                 155                 160

Val Gln Trp Lys Val Asp Asn Ala Leu Pro Ile
            165                 170

<210> SEQ ID NO 11
<211> LENGTH: 425
<212> TYPE: DNA
<213> ORGANISM: homo sapien

<400> SEQUENCE: 11
ccatggaagt tggggctgag ctgggttttc ctcgttgctc ttttaagagg tgtccagtgt     60
caggtgcagc tggtggagtc tgggggaggc gtggtccagc ctgggaggtc cctgagactc    120
tcctgtgcag cgtctggatt caccttcagt tgctatggca tgcactgggt ccgccaggct    180
ccaggcaagg ggctggagtg ggtggcagtt atatggtatg atggaagtaa taaatactat    240
gcagactccg tgaagggccg attcaccatc tccagagaca attccaagaa cacgctgtat    300
ctgcaaatga acagcctgag agccgaggac acggctgtat attactgtgc cggggggagct    360 acggccatgg acgtctgggg ccaagggacc acggtcaccg tctcctcagc ctccaccaag    420
ggccc                                                                425

<210> SEQ ID NO 12
<211> LENGTH: 141
<212> TYPE: PRT
<213> ORGANISM: homo sapien

<400> SEQUENCE: 12

Pro Trp Lys Leu Gly Leu Ser Trp Val Phe Leu Val Ala Leu Leu Arg
1               5                   10                  15

Gly Val Gln Cys Gln Val Gln Leu Val Glu Ser Gly Gly Gly Val Val
                20                  25                  30

Gln Pro Gly Arg Ser Leu Arg Leu Ser Cys Ala Ala Ser Gly Phe Thr
            35                  40                  45

Phe Ser Cys Tyr Gly Met His Trp Val Arg Gln Ala Pro Gly Lys Gly
50                  55                  60

Leu Glu Trp Val Ala Val Ile Trp Tyr Asp Gly Ser Asn Lys Tyr Tyr
65                  70                  75                  80

Ala Asp Ser Val Lys Gly Arg Phe Thr Ile Ser Arg Asp Asn Ser Lys
                85                  90                  95

Asn Thr Leu Tyr Leu Gln Met Asn Ser Leu Arg Ala Glu Asp Thr Ala
            100                 105                 110

Val Tyr Tyr Cys Ala Gly Gly Ala Thr Ala Met Asp Val Trp Gly Gln
        115                 120                 125

Gly Thr Thr Val Thr Val Ser Ser Ala Ser Thr Lys Gly
    130                 135                 140

<210> SEQ ID NO 13
<211> LENGTH: 642
<212> TYPE: DNA
<213> ORGANISM: homo sapien

<400> SEQUENCE: 13
gacatccaga tgacccagtc tccatcctcc ctgtctgcat ctgtaggaga cagagtcacc     60
agcacttgcc gggcgagtca ggacattagc aattatttag cctggtatca gcagaaacca    120
gggaaagttc ctaagctcct gatctatgct gcatccactt tgcaatcagg ggtcccatct    180
```

```
cggttcagtg gcagtggatc tgggacagat tcactctca ccatcagcag cctgcagcct    240
gaagatgttg caacttatta ctgtcaaaag tataacagtg ccccgtggac gttcggccaa    300
gggaccaagg tggaaatcaa acgaactgtg ctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag cacccctgacg    540 ctgagcaaag cagactacga gaaacacaaa gtctacgcct gcgaagtcac ccatcagggc    600
ctgagctcgc ccgtcacaaa gagcttcaac aggggagagt gt                       642
```

<210> SEQ ID NO 14
<211> LENGTH: 214
<212> TYPE: PRT
<213> ORGANISM: homo sapien

<400> SEQUENCE: 14

```
Asp Ile Gln Met Thr Gln Ser Pro Ser Ser Leu Ser Ala Ser Val Gly
 1               5                  10                  15

Asp Arg Val Thr Ser Thr Cys Arg Ala Ser Gln Asp Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 15
<211> LENGTH: 1362
<212> TYPE: DNA
<213> ORGANISM: homo sapien

<400> SEQUENCE: 15

```
caggtccagc tggtacagtc gggggctgag gtgaagaagc ctggggcctc agtgaaggtc    60
tcctgcaagg tttccggata caccctcact gaattatcca tgcactgggt gcgacaggct    120
cctggaaaag ggcttgagtg gatgggaggt tttgatcctg aagatggtga acaatctac    180
```

-continued

```
gcacagatgt tccagggcag agtcaccatg accgaggaca catctacaga cacagcctac    240
atggacctga gcagcctgag atctgaggac acggccgtgt attactgtgc aaccggaacg    300
tattacgata ttttgactgg tccctcctac tactactacg gtttgggcgt ctggggccaa    360
gggaccacgg tcaccgtctc ctcagcctcc accaagggcc catcggtctt ccccctggcg    420
ccctgctcca ggagcacctc cgagagcaca gcggccctgg gctgcctggt caaggactac    480
ttccccgaac cggtgacggt gtcgtggaac tcaggcgctc tgaccagcgg cgtgcacacc    540
ttcccagctg tcctacagtc ctcaggactc tactccctca gcagcgtggt gaccgtgccc    600
tccagcaact tcggcaccca gacctacacc tgcaactag atcacaagcc cagcaacacc    660
aaggtggaca agacagttga gcgcaaatgt tgtgtcgagt gcccaccgtg cccagcacca    720
cctgtggcag accgtcagt cttcctcttc cccccaaaac ccaaggacac cctcatgatc    780
tcccggaccc ctgaggtcac gtgcgtggtg gtggacgtga gccacgaaga ccccgaggtc    840
cagttcaact ggtacgtgga cggcgtggag gtgcataatg ccaagacaaa gccacgggag    900
gagcagttca acagcacgtt ccgtgtggtc agcgtcctca ccgttgtgca ccaggactgg    960
ctgaacggca aggagtacaa gtgcaaggtc tccaacaaag gcctcccagc ccccatcgag   1020
aaaaccatct ccaaaaccaa agggcagccc cgagaaccac aggtgtacac cctgccccca   1080
tcccgggagg agatgaccaa gaaccaggtc agcctgacct gcctggtcaa aggcttctac   1140
cccagcgaca tcgccgtgga gtgggagagc aatgggcagc cggagaacaa ctacaagacc   1200
acacctccca tgctggactc cgacggctcc ttcttcctct acagcaagct caccgtggac   1260
aagagcaggt ggcagcaggg gaacgtcttc tcatgctccg tgatgcatga ggctctgcac   1320
aaccactaca cgcagaagag cctctccctg tctccgggta aa                      1362
```

<210> SEQ ID NO 16
<211> LENGTH: 454
<212> TYPE: PRT
<213> ORGANISM: homo sapien

<400> SEQUENCE: 16

```
Gln Val Gln Leu Val Gln Ser Gly Ala Glu Val Lys Lys Pro Gly Ala
  1               5                  10                  15

Ser Val Lys Val Ser Cys Lys Val Ser Gly Tyr Thr Leu Thr Glu Leu
             20                  25                  30

Ser Met His Trp Val Arg Gln Ala Pro Gly Lys Gly Leu Glu Trp Met
         35                  40                  45

Gly Gly Phe Asp Pro Glu Asp Gly Glu Thr Ile Tyr Ala Gln Met Phe
     50                  55                  60

Gln Gly Arg Val Thr Met Thr Glu Asp Thr Ser Thr Asp Thr Ala Tyr
 65                  70                  75                  80

Met Asp Leu Ser Ser Leu Arg Ser Glu Asp Thr Ala Val Tyr Tyr Cys
                 85                  90                  95

Ala Thr Gly Thr Tyr Tyr Asp Ile Leu Thr Gly Pro Ser Tyr Tyr Tyr
            100                 105                 110

Tyr Gly Leu Gly Val Trp Gly Gln Gly Thr Thr Val Thr Val Ser Ser
        115                 120                 125

Ala Ser Thr Lys Gly Pro Ser Val Phe Pro Leu Ala Pro Cys Ser Arg
    130                 135                 140

Ser Thr Ser Glu Ser Thr Ala Ala Leu Gly Cys Leu Val Lys Asp Tyr
145                 150                 155                 160
```

```
Phe Pro Glu Pro Val Thr Val Ser Trp Asn Ser Gly Ala Leu Thr Ser
                165                 170                 175
Gly Val His Thr Phe Pro Ala Val Leu Gln Ser Ser Gly Leu Tyr Ser
            180                 185                 190
Leu Ser Ser Val Val Thr Val Pro Ser Ser Asn Phe Gly Thr Gln Thr
        195                 200                 205
Tyr Thr Cys Asn Val Asp His Lys Pro Ser Asn Thr Lys Val Asp Lys
    210                 215                 220
Thr Val Glu Arg Lys Cys Cys Val Glu Cys Pro Cys Pro Ala Pro
225                 230                 235                 240
Pro Val Ala Gly Pro Ser Val Phe Leu Phe Pro Pro Lys Pro Lys Asp
                245                 250                 255
Thr Leu Met Ile Ser Arg Thr Pro Glu Val Thr Cys Val Val Val Asp
                260                 265                 270
Val Ser His Glu Asp Pro Glu Val Gln Phe Asn Trp Tyr Val Asp Gly
            275                 280                 285
Val Glu Val His Asn Ala Lys Thr Lys Pro Arg Glu Glu Gln Phe Asn
        290                 295                 300
Ser Thr Phe Arg Val Val Ser Val Leu Thr Val Val His Gln Asp Trp
305                 310                 315                 320
Leu Asn Gly Lys Glu Tyr Lys Cys Lys Val Ser Asn Lys Gly Leu Pro
                325                 330                 335
Ala Pro Ile Glu Lys Thr Ile Ser Lys Thr Lys Gly Gln Pro Arg Glu
                340                 345                 350
Pro Gln Val Tyr Thr Leu Pro Pro Ser Arg Glu Glu Met Thr Lys Asn
            355                 360                 365
Gln Val Ser Leu Thr Cys Leu Val Lys Gly Phe Tyr Pro Ser Asp Ile
        370                 375                 380
Ala Val Glu Trp Glu Ser Asn Gly Gln Pro Glu Asn Asn Tyr Lys Thr
385                 390                 395                 400
Thr Pro Pro Met Leu Asp Ser Asp Gly Ser Phe Phe Leu Tyr Ser Lys
                405                 410                 415
Leu Thr Val Asp Lys Ser Arg Trp Gln Gln Gly Asn Val Phe Ser Cys
                420                 425                 430
Ser Val Met His Glu Ala Leu His Asn His Tyr Thr Gln Lys Ser Leu
            435                 440                 445
Ser Leu Ser Pro Gly Lys
        450

<210> SEQ ID NO 17
<211> LENGTH: 642
<212> TYPE: DNA
<213> ORGANISM: homo sapien

<400> SEQUENCE: 17
gacatccaga tgacccagtc tccatcctcc ctgtctgcat ctgtaggaga cagagtcacc      60
atcacttgcc gggcgagtca gggcattagc aattatttag cctggtatca gcagaaacca    120
gggaaagttc ctaagctcct gatctatgct gcatccactt tgcaatcagg gtcccatct     180 cggttcagtg gcagtggatc tgggacagat ttcactctca ccatcagcag cctgcagcct    240
gaagatgttg caacttatta ctgtcaaaag tatgacagtg ccccgtggac gttcggccaa    300
gggaccaagg tggaaatcaa acgaactgtg gctgcaccat ctgtcttcat cttcccgcca    360
tctgatgagc agttgaaatc tggaactgcc tctgttgtgt gcctgctgaa taacttctat    420
```

-continued

```
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gt                      642
```

<210> SEQ ID NO 18
<211> LENGTH: 214
<212> TYPE: PRT
<213> ORGANISM: homo sapien

<400> SEQUENCE: 18

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asp Ser Ala Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 19
<211> LENGTH: 1330
<212> TYPE: DNA
<213> ORGANISM: homo sapien

<400> SEQUENCE: 19

```
caggtgcagc tgcaggagtc gggcccagga ctggtgaagc cttcggagac cctgtccctc    60
acctgcactg tctctggtgg ctccatcagt atttactact ggagctggat ccggcagccc    120
ccagggaagg gactggagtg gattgggtat atctattaca gtgggagcac caactacaac    180
ccctccctca gagtcgagt caccatatca gtagacacgt ccaagaacca gttctccctg    240
aagctgagct ctgtgaccgc tgcggacacg gccgtgtatt actgtgcggt ttggaactac    300
ggggatgctt ttgatatctg gggccaaggg acaatggtca ccgtctcttc agcctccacc    360
aagggcccat cggtcttccc cctggcgccc tgctccagga gcacctccga gagcacagcg    420
```

```
gccctgggct gcctggtcaa ggactacttc cccgaaccgg tgacggtgtc gtggaactca    480
ggcgctctga ccagcggcgt gcacaccttc ccagctgtcc tacagtcctc aggactctac    540
tccctcagca gcgtggtgac cgtgccctcc agcaacttcg gcacccagac ctacacctgc    600
aacgtagatc acaagcccag caacaccaag gtggacaaga cagttgagcg caaatgttgt    660
gtcgagtgcc caccgtgccc agcaccacct gtggcaggac cgtcagtctt cctcttcccc    720
ccaaaaccca aggacaccct catgatctcc cggacccctg aggtcacgtg cgtggtggtg    780
gacgtgagcc acgaagaccc cgaggtccag ttcaactggt acgtggacgg cgtggaggtg    840
cataatgcca agacaaagcc acgggaggag cagttcaaca gcacgttccg tgtggtcagc    900
gtcctcaccg ttgtgcacca ggactggctg aacggcaagg agtacaagtg caaggtctcc    960
aacaaaggcc tcccagcccc catcgagaaa accatctcca aaaccaaagg cagccccga    1020
gaaccacagg tgtacaccct gcccccatcc cgggaggaga tgaccaagaa ccaggtcagc    1080
ctgacctgcc tggtcaaagg cttctacccc agcgacatcg ccgtggagtg ggagagcaat    1140
gggcagccgg agaacaacta caagaccaca cctcccatgc tggactccga cggctccttc    1200
ttcctctaca gcaagctcac cgtggacaag agcaggtggc agcaggggaa cgtcttctca    1260
tgctccgtga tgcatgaggc tctgcacaac cactacacgc agaagagcct ctccctgtct    1320
ccgggtaaaa                                                           1330

<210> SEQ ID NO 20
<211> LENGTH: 443
<212> TYPE: PRT
<213> ORGANISM: homo sapien

<400> SEQUENCE: 20

Gln Val Gln Leu Gln Glu Ser Gly Pro Gly Leu Val Lys Pro Ser Glu
  1               5                   10                  15

Thr Leu Ser Leu Thr Cys Thr Val Ser Gly Gly Ser Ile Ser Ile Tyr
             20                  25                  30

Tyr Trp Ser Trp Ile Arg Gln Pro Pro Gly Lys Gly Leu Glu Trp Ile
         35                  40                  45

Gly Tyr Ile Tyr Tyr Ser Gly Ser Thr Asn Tyr Asn Pro Ser Leu Lys
     50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Val Trp Asn Tyr Gly Asp Ala Phe Asp Ile Trp Gly Gln Gly Thr Met
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205
```

```
Thr Lys Val Asp Lys Thr Val Glu Arg Lys Cys Cys Val Glu Cys Pro
    210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Phe Arg Val Val Ser Val Leu Thr Val
    290                 295                 300

Val His Gln Asp Trp Leu Asn Gly Lys Glu Tyr Lys Cys Lys Val Ser
305                 310                 315                 320

Asn Lys Gly Leu Pro Ala Pro Ile Glu Lys Thr Ile Ser Lys Thr Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Met Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
        435                 440

<210> SEQ ID NO 21
<211> LENGTH: 108
<212> TYPE: PRT
<213> ORGANISM: homo sapien

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Trp
                85                  90                  95

Thr Phe Gly Gln Gly Thr Lys Val Glu Ile Lys Arg
            100                 105

<210> SEQ ID NO 22
<211> LENGTH: 108
<212> TYPE: PRT
<213> ORGANISM: homo sapien
```

<400> SEQUENCE: 22

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asp Ser Ala Pro Trp
                85                  90                  95

Thr Phe Gly Gln Gly Thr Lys Val Glu Ile Lys Arg
            100                 105

<210> SEQ ID NO 23
<211> LENGTH: 108
<212> TYPE: PRT
<213> ORGANISM: homo sapien

<400> SEQUENCE: 23

Asp Ile Gln Met Thr Gln Ser Pro Ser Ser Leu Ser Ala Ser Val Gly
1               5                   10                  15

Asp Arg Val Thr Ser Thr Cys Arg Ala Ser Gln Asp Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asp Ser Ala Pro Trp
                85                  90                  95

Thr Phe Gly Gln Gly Thr Lys Val Glu Ile Lys Arg
            100                 105

<210> SEQ ID NO 24
<211> LENGTH: 105
<212> TYPE: PRT
<213> ORGANISM: homo sapien

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Phe Gly
                85                  90                  95

Gly Gly Thr Lys Val Glu Ile Lys Arg
            100                 105

<210> SEQ ID NO 25
<211> LENGTH: 108
<212> TYPE: PRT
<213> ORGANISM: homo sapiens

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Ser Ser Phe
            20                  25                  30

Leu Asn Trp Tyr Gln Gln Lys Ser Gly Lys Ala Pro Lys Leu Leu Ile
        35                  40                  45

Phe Ala Thr Ser Arg Leu Gln Ser Gly Val Pro Ser Arg Ile Ser Gly
    50                  55                  60

Ser Gly Ser Gly Thr Asp Phe Thr Leu Thr Ile Ser Gly Leu Gln Pro
65                  70                  75                  80

Glu Asp Phe Ala Thr Phe Tyr Cys Gln Gln Ser Tyr Ser Ile Pro Leu
                85                  90                  95

Thr Phe Gly Gly Gly Thr Lys Val Asp Ile Lys Arg
            100                 105

<210> SEQ ID NO 26
<211> LENGTH: 106
<212> TYPE: PRT
<213> ORGANISM: homo sapiens

<400> SEQUENCE: 26

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Thr Phe
                85                  90                  95

Gly Gln Gly Thr Lys Val Glu Ile Lys Arg
            100                 105

<210> SEQ ID NO 27
<211> LENGTH: 108
<212> TYPE: PRT
<213> ORGANISM: homo sapiens

<400> SEQUENCE: 27

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

```
Leu Ala Trp Tyr Gln Gln Lys Pro Gly Lys Ala Pro Lys Leu Leu Ile
        35                  40                  45

Tyr Val Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Gln Gln Ala Asp Ser Phe Pro Arg
                85                  90                  95

Thr Phe Gly Gln Gly Thr Lys Val Glu Ile Lys Arg
            100                 105

<210> SEQ ID NO 28
<211> LENGTH: 108
<212> TYPE: PRT
<213> ORGANISM: homo sapiens

<400> SEQUENCE: 28

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Leu
                85                  90                  95

Thr Phe Gly Gly Gly Thr Lys Val Glu Ile Lys Arg
            100                 105

<210> SEQ ID NO 29
<211> LENGTH: 108
<212> TYPE: PRT
<213> ORGANISM: homo sapiens

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Thr Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Asn Tyr Asp Asn Leu Pro Leu
                85                  90                  95

Thr Phe Gly Gly Gly Thr Lys Val Glu Ile Lys Arg
            100                 105

<210> SEQ ID NO 30
<211> LENGTH: 11
<212> TYPE: PRT
<213> ORGANISM: homo sapiens
```

```
<400> SEQUENCE: 30

Arg Ala Ser Gln Gly Ile Ser Asn Tyr Leu Ala
 1               5                   10

<210> SEQ ID NO 31
<211> LENGTH: 11
<212> TYPE: PRT
<213> ORGANISM: homo sapiens

<400> SEQUENCE: 31

Arg Ala Ser Gln Asp Ile Ser Asn Tyr Leu Ala
 1               5                   10

<210> SEQ ID NO 32
<211> LENGTH: 11
<212> TYPE: PRT
<213> ORGANISM: homo sapiens

<400> SEQUENCE: 32

Arg Ala Ser Gln Asn Ile Ser Ser Phe Leu Asn
 1               5                   10

<210> SEQ ID NO 33
<211> LENGTH: 11
<212> TYPE: PRT
<213> ORGANISM: homo sapiens

<400> SEQUENCE: 33

Gln Ala Ser Gln Asp Ile Ser Asn Tyr Leu Asn
 1               5                   10

<210> SEQ ID NO 34
<211> LENGTH: 11
<212> TYPE: PRT
<213> ORGANISM: homo sapiens

<400> SEQUENCE: 34

Arg Ala Ser Gln Gly Ile Ser Ser Trp Leu Ala
 1               5                   10

<210> SEQ ID NO 35
<211> LENGTH: 7
<212> TYPE: PRT
<213> ORGANISM: homo sapiens

<400> SEQUENCE: 35

Ala Ala Ser Thr Leu Gln Ser
 1               5

<210> SEQ ID NO 36
<211> LENGTH: 7
<212> TYPE: PRT
<213> ORGANISM: homo sapiens

<400> SEQUENCE: 36

Ala Ala Ser Thr Leu Gln Ser
 1               5

<210> SEQ ID NO 37
<211> LENGTH: 7
<212> TYPE: PRT
<213> ORGANISM: homo sapiens
```

```
<400> SEQUENCE: 37

Ala Thr Ser Arg Leu Gln Ser
 1               5

<210> SEQ ID NO 38
<211> LENGTH: 7
<212> TYPE: PRT
<213> ORGANISM: homo sapiens

<400> SEQUENCE: 38

Asp Ala Ser Thr Leu Glu Thr
 1               5

<210> SEQ ID NO 39
<211> LENGTH: 7
<212> TYPE: PRT
<213> ORGANISM: homo sapiens

<400> SEQUENCE: 39

Val Ala Ser Ser Leu Gln Ser
 1               5

<210> SEQ ID NO 40
<211> LENGTH: 9
<212> TYPE: PRT
<213> ORGANISM: homo sapiens

<400> SEQUENCE: 40

Gln Lys Tyr Asp Ser Ala Pro Trp Thr
 1               5

<210> SEQ ID NO 41
<211> LENGTH: 9
<212> TYPE: PRT
<213> ORGANISM: homo sapiens

<400> SEQUENCE: 41

Gln Lys Tyr Asn Ser Ala Pro Trp Thr
 1               5

<210> SEQ ID NO 42
<211> LENGTH: 9
<212> TYPE: PRT
<213> ORGANISM: homo sapiens

<400> SEQUENCE: 42

Gln Gln Ser Tyr Ser Ile Pro Leu Thr
 1               5

<210> SEQ ID NO 43
<211> LENGTH: 9
<212> TYPE: PRT
<213> ORGANISM: homo sapiens

<400> SEQUENCE: 43

Gln Asn Tyr Asp Asn Leu Pro Leu Thr
 1               5

<210> SEQ ID NO 44
<211> LENGTH: 9
<212> TYPE: PRT
<213> ORGANISM: homo sapiens
```

<400> SEQUENCE: 44

Gln Gln Ala Asp Ser Phe Pro Arg Thr
1               5

<210> SEQ ID NO 45
<211> LENGTH: 126
<212> TYPE: PRT
<213> ORGANISM: Homo sapiens

<400> SEQUENCE: 45

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Asp Ser Ser Gly Tyr Tyr Tyr Tyr Tyr Gly Met
                100                 105                 110

Asp Val Trp Gly Gln Gly Thr Thr Val Thr Val Ser Ser Ala
            115                 120                 125

<210> SEQ ID NO 46
<211> LENGTH: 127
<212> TYPE: PRT
<213> ORGANISM: Homo sapiens

<400> SEQUENCE: 46

Gln Glu Gln Ser Gly Gly Gly Val Val Gln Pro Gly Arg Ser Leu Arg
1               5                   10                  15

Leu Ser Cys Ala Ala Ser Gly Phe Thr Phe Ser Asn Tyr Gly Ile His
                20                  25                  30

Trp Val Arg Gln Ala Pro Gly Lys Gly Leu Glu Trp Val Ala Val Ile
            35                  40                  45

Trp Tyr Asp Gly Asn Asn Lys Tyr Tyr Ala Asp Ser Val Lys Gly Arg
        50                  55                  60

Phe Thr Ile Ser Arg Asp Asn Ser Lys Asn Thr Leu Tyr Leu Gln Met
65                  70                  75                  80

Asn Ser Leu Arg Ala Glu Asp Thr Ala Val Tyr Tyr Cys Ala Arg Gly
                85                  90                  95

Gly Tyr Tyr Asp Ser Arg Gly Tyr Tyr Thr Pro Tyr Tyr Tyr Gly
                100                 105                 110

Met Asp Val Trp Gly Gln Gly Thr Thr Val Thr Val Ser Ser Ala
            115                 120                 125

<210> SEQ ID NO 47
<211> LENGTH: 113
<212> TYPE: PRT
<213> ORGANISM: Homo sapiens

<400> SEQUENCE: 47

```
Gln Val Gln Leu Val Glu Ser Gly Gly Val Val Gln Pro Gly Arg
 1               5                  10                  15
Ser Leu Arg Leu Ser Cys Ala Ala Ser Gly Phe Thr Phe Ser Ser Tyr
             20                  25                  30
Gly Met His Trp Val Arg Gln Ala Pro Gly Lys Gly Leu Glu Trp Val
         35                  40                  45
Ala Val Ile Trp Tyr Asp Gly Ser Asn Lys Tyr Tyr Ala Asp Ser Val
     50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                 85                  90                  95
Gly Gly Met Asp Val Trp Gly Gln Gly Thr Thr Val Thr Val Ser Ser
            100                 105                 110
Ala
```

<210> SEQ ID NO 48
<211> LENGTH: 117
<212> TYPE: PRT
<213> ORGANISM: Homo sapiens

<400> SEQUENCE: 48

```
Gln Val Gln Leu Val Glu Ser Gly Gly Gly Val Val Gln Pro Gly Arg
 1               5                  10                  15
Ser Leu Arg Leu Ser Cys Ala Ala Ser Gly Phe Thr Phe Ser Cys Tyr
             20                  25                  30
Gly Met His Trp Val Arg Gln Ala Pro Gly Lys Gly Leu Glu Trp Val
         35                  40                  45
Ala Val Ile Trp Tyr Asp Gly Ser Asn Lys Tyr Tyr Ala Asp Ser Val
     50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                 85                  90                  95
Ala Gly Gly Ala Thr Ala Met Asp Val Trp Gly Gln Gly Thr Thr Val
            100                 105                 110
Thr Val Ser Ser Ala
        115
```

<210> SEQ ID NO 49
<211> LENGTH: 124
<212> TYPE: PRT
<213> ORGANISM: Homo sapiens

<400> SEQUENCE: 49

```
Gln Val Gln Leu Val Gln Ser Gly Ala Glu Val Lys Lys Pro Gly Ala
 1               5                  10                  15
Ser Val Lys Val Ser Cys Lys Val Ser Gly Tyr Thr Leu Thr Glu Leu
             20                  25                  30
Ser Met His Trp Val Arg Gln Ala Pro Gly Lys Gly Leu Glu Trp Met
         35                  40                  45
Gly Gly Phe Asp Pro Glu Asp Gly Glu Thr Ile Tyr Ala Gln Lys Phe
     50                  55                  60
Gln Gly Arg Val Thr Met Thr Glu Asp Thr Ser Thr Asp Thr Ala Tyr
65                  70                  75                  80
```

```
Met Glu Leu Ser Ser Leu Arg Ser Glu Asp Thr Ala Val Tyr Tyr Cys
                85                  90                  95

Ala Tyr Tyr Asp Ile Leu Thr Gly Tyr Tyr Tyr Gly Met Asp Val
            100                 105                 110

Trp Gly Gln Gly Thr Thr Val Thr Val Ser Ser Ala
        115                 120
```

<210> SEQ ID NO 50
<211> LENGTH: 129
<212> TYPE: PRT
<213> ORGANISM: Homo sapiens

<400> SEQUENCE: 50

```
Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Met Phe
    50                  55                  60

Gln Gly Arg Val Thr Met Thr Glu Asp Thr Ser Thr Asp Thr Ala Tyr
65                  70                  75                  80

Met Asp Leu Ser Ser Leu Arg Ser Glu Asp Thr Ala Val Tyr Tyr Cys
                85                  90                  95

Ala Thr Gly Thr Tyr Tyr Asp Ile Leu Thr Gly Pro Ser Tyr Tyr Tyr
            100                 105                 110

Tyr Gly Met Asp Val Trp Gly Gln Gly Thr Thr Val Thr Val Ser Ser
        115                 120                 125

Ala
```

<210> SEQ ID NO 51
<211> LENGTH: 118
<212> TYPE: PRT
<213> ORGANISM: Homo sapiens

<400> SEQUENCE: 51

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Thr Gly Asp Tyr Phe Asp Tyr Trp Gly Gln Gly Thr Leu
            100                 105                 110

Val Thr Val Ser Ser Ala
        115
```

```
<210> SEQ ID NO 52
<211> LENGTH: 118
<212> TYPE: PRT
<213> ORGANISM: Homo sapiens

<400> SEQUENCE: 52

Gln Val Gln Leu Glu Gln Ser Gly Pro Gly Leu Val Lys Pro Ser Gln
 1               5                  10                  15

Thr Leu Ser Leu Thr Cys Thr Val Ser Gly Asp Ser Ile Ser Ser Gly
             20                  25                  30

Gly His Tyr Trp Ser Trp Ile Arg Gln His Pro Gly Lys Gly Leu Glu
         35                  40                  45

Trp Ile Gly Tyr Ile Tyr Tyr Ser Gly Ser Ser Tyr Tyr Asn Pro Ser
     50                  55                  60

Leu Lys Ser Arg Phe Thr Ile Ser Val Asp Thr Ser Lys Asn Gln Phe
 65                  70                  75                  80

Ser Leu Lys Leu Thr Ser Val Thr Ala Ala Asp Thr Ala Val Tyr Tyr
                 85                  90                  95

Cys Ala Arg Thr Gly Asp Tyr Phe Asp Tyr Trp Gly Leu Gly Thr Leu
            100                 105                 110

Val Thr Val Ser Ser Ala
            115

<210> SEQ ID NO 53
<211> LENGTH: 115
<212> TYPE: PRT
<213> ORGANISM: Homo sapiens

<400> SEQUENCE: 53

Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Ser Tyr
             20                  25                  30

Tyr Trp Ser Trp Ile Arg Gln Pro Pro Gly Lys Gly Leu Glu Trp Ile
         35                  40                  45

Gly Tyr Ile Tyr Tyr Ser Gly Ser Thr Asn Tyr Asn Pro Ser Leu Lys
     50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Trp Asn Tyr Ala Phe Asp Ile Trp Gly Gln Gly Thr Met Val Thr Val
            100                 105                 110

Ser Ser Ala
        115

<210> SEQ ID NO 54
<211> LENGTH: 118
<212> TYPE: PRT
<213> ORGANISM: Homo sapiens

<400> SEQUENCE: 54

Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Ile Tyr
             20                  25                  30

Tyr Trp Ser Trp Ile Arg Gln Pro Pro Gly Lys Gly Leu Glu Trp Ile
         35                  40                  45
```

```
Gly Tyr Ile Tyr Tyr Ser Gly Ser Thr Asn Tyr Asn Pro Ser Leu Lys
        50                  55                  60
Ser Arg Val Thr Ile Ser Val Asp Thr Ser Lys Asn Gln Phe Ser Leu
 65                  70                  75                  80
Lys Leu Ser Ser Val Thr Ala Ala Asp Thr Ala Val Tyr Tyr Cys Ala
                 85                  90                  95
Val Trp Asn Tyr Gly Asp Ala Phe Asp Ile Trp Gly Gln Gly Thr Met
            100                 105                 110
Val Thr Val Ser Ser Ala
        115
```

```
<210> SEQ ID NO 55
<211> LENGTH: 25
<212> TYPE: DNA
<213> ORGANISM: Homo sapiens

<400> SEQUENCE: 55
ttactatgat agtcgtggtt attac                                          25

<210> SEQ ID NO 56
<211> LENGTH: 22
<212> TYPE: DNA
<213> ORGANISM: Homo sapiens

<400> SEQUENCE: 56
gtattacgat attttgactg gt                                             22

<210> SEQ ID NO 57
<211> LENGTH: 10
<212> TYPE: PRT
<213> ORGANISM: Homo sapiens

<400> SEQUENCE: 57

Gly Phe Thr Phe Ser Asn Tyr Gly Ile His
 1               5                  10

<210> SEQ ID NO 58
<211> LENGTH: 10
<212> TYPE: PRT
<213> ORGANISM: Homo sapiens

<400> SEQUENCE: 58

Gly Phe Thr Phe Ser Cys Tyr Gly Met His
 1               5                  10

<210> SEQ ID NO 59
<211> LENGTH: 10
<212> TYPE: PRT
<213> ORGANISM: Homo sapiens

<400> SEQUENCE: 59

Gly Tyr Thr Leu Thr Glu Leu Ser Met His
 1               5                  10

<210> SEQ ID NO 60
<211> LENGTH: 12
<212> TYPE: PRT
<213> ORGANISM: Homo sapiens

<400> SEQUENCE: 60

Gly Asp Ser Ile Ser Ser Gly Gly His Tyr Trp Ser
 1               5                  10
```

```
<210> SEQ ID NO 61
<211> LENGTH: 10
<212> TYPE: PRT
<213> ORGANISM: Homo sapiens

<400> SEQUENCE: 61

Gly Gly Ser Ile Ser Ile Tyr Tyr Trp Ser
1               5                   10

<210> SEQ ID NO 62
<211> LENGTH: 17
<212> TYPE: PRT
<213> ORGANISM: Homo sapiens

<400> SEQUENCE: 62

Val Ile Trp Tyr Asp Gly Asn Asn Lys Tyr Tyr Ala Asp Ser Val Lys
1               5                   10                  15

Gly

<210> SEQ ID NO 63
<211> LENGTH: 17
<212> TYPE: PRT
<213> ORGANISM: Homo sapiens

<400> SEQUENCE: 63

Val Ile Trp Tyr Asp Gly Ser Asn Lys Tyr Tyr Ala Asp Ser Val Lys
1               5                   10                  15

Gly

<210> SEQ ID NO 64
<211> LENGTH: 17
<212> TYPE: PRT
<213> ORGANISM: Homo sapiens

<400> SEQUENCE: 64

Gly Phe Asp Pro Glu Asp Gly Glu Thr Ile Tyr Ala Gln Met Phe Gln
1               5                   10                  15

Gly

<210> SEQ ID NO 65
<211> LENGTH: 16
<212> TYPE: PRT
<213> ORGANISM: Homo sapiens

<400> SEQUENCE: 65

Tyr Ile Tyr Tyr Ser Gly Ser Ser Tyr Tyr Asn Pro Ser Leu Lys Ser
1               5                   10                  15

<210> SEQ ID NO 66
<211> LENGTH: 16
<212> TYPE: PRT
<213> ORGANISM: Homo sapiens

<400> SEQUENCE: 66

Tyr Ile Tyr Tyr Ser Gly Ser Thr Asn Tyr Asn Pro Ser Leu Lys Ser
1               5                   10                  15

<210> SEQ ID NO 67
<211> LENGTH: 20
<212> TYPE: PRT
<213> ORGANISM: Homo sapiens
```

```
<400> SEQUENCE: 67

Gly Gly Tyr Tyr Asp Ser Arg Gly Tyr Tyr Thr Pro Tyr Tyr Tyr
1               5                   10                  15

Gly Met Asp Val
            20

<210> SEQ ID NO 68
<211> LENGTH: 7
<212> TYPE: PRT
<213> ORGANISM: Homo sapiens

<400> SEQUENCE: 68

Gly Ala Thr Ala Met Asp Val
1               5

<210> SEQ ID NO 69
<211> LENGTH: 19
<212> TYPE: PRT
<213> ORGANISM: Homo sapiens

<400> SEQUENCE: 69

Gly Thr Tyr Tyr Asp Ile Leu Thr Gly Pro Ser Tyr Tyr Tyr Gly
1               5                   10                  15

Leu Gly Val

<210> SEQ ID NO 70
<211> LENGTH: 7
<212> TYPE: PRT
<213> ORGANISM: Homo sapiens

<400> SEQUENCE: 70

Thr Gly Asp Tyr Phe Asp Tyr
1               5

<210> SEQ ID NO 71
<211> LENGTH: 9
<212> TYPE: PRT
<213> ORGANISM: Homo sapiens

<400> SEQUENCE: 71

Trp Asn Tyr Gly Asp Ala Phe Asp Ile
1               5
```

ANTI-PROPERDIN ANTIBODIES, AND METHODS FOR MAKING AND USING SAME

FIELD OF THE INVENTION

The present invention is in the field of antibodies, and in particular, antibodies specific for properdin.

BACKGROUND OF THE INVENTION

The complement system provides an early acting mechanism to initiate and amplify the inflammatory response to microbial infection and other acute insults. While complement activation provides a valuable first line of defense against pathogens, inappropriate activation of complement poses potential harm to the host. For instance, the complement system has been implicated in contributing to the pathogenesis of several acute and chronic conditions, including post-cardiopulmonary bypass inflammation, myocardial infarction, stroke, acute respiratory distress syndrome (ARDS), septic shock, transplant rejection, burn injury, multiple sclerosis, myasthenia gravis, and rheumatoid arthritis. It is important to note that while complement may not be the sole cause of pathogenesis in these conditions, complement activation appears to be a major contributing factor and represents a site of therapeutic intervention. This growing recognition of the importance of complement-mediated tissue injury in a variety of disease states underscores the need for effective complement inhibitory drugs.

The complement system can be activated through either of two enzymatic cascades, referred to as the classical and alternative pathways. These pathways are shown schematically in FIG. 11. Increasing scientific evidence argues that the alternative complement pathway plays a predominant role in eliciting pathology in many acute and chronic disorders.

The classical pathway is triggered by antibody bound to a foreign pathogen, and thus requires prior exposure to the pathogen for the generation of specific antibody. There are three plasma proteins specifically involved in the classical pathway: C1, C2, and C4. In contrast, the alternative pathway is spontaneously triggered by foreign or other abnormal surfaces (bacteria, yeast, virally infected cells, or damaged tissue) and is therefore capable of an immediate response. There are also three plasma proteins specific to the alternative pathway: factors B and D, and properdin. It is important to note that both the classical and alternative complement pathways share common proteins (C3, C5-9) that are involved in the later stages of the activation cascades. The bioactive molecules produced after activation of either complement pathway include the anaphylatoxins C3a and C5a, as well as the terminal complement complex known as C5b-9, also referred to as the membrane attack complex (MAC). These anaphylatoxins initiate a cellular inflammatory response that is beneficial in the case of a pathogenic infection, but is potentially detrimental when inappropriately generated. For example, MAC causes cellular damage through its insertion into cell membranes. Like C3a and C5a, MAC can play a positive role in the destruction of pathogens, but can be deleterious when it attacks host cells.

Until recently, the role of complement activation in disease pathogenesis was poorly understood. This was due in part, to the absence of specific inhibitors that could be used to directly evaluate the role of complement in animal disease models. The development of a soluble form of the complement receptor 1 (sCR1), an inhibitor of both complement pathways, has shed light on the role complement activation plays in disease pathogenesis. The sCR1 molecule suppresses complement activation by reversibly binding to the C3b and C4b subunits present in the C3-(C4b2a and C3bBb) and C5-convertases (C4b2a3b and (C3b)2Bb) of the two complement pathways. sCR1 has been demonstrated to be beneficial in animal models of inflammation, ischemia-reperfusion, transplant rejection, trauma, and autoimmune disease.

Although sCR1 is effective in inhibiting complement in vivo, it may have limitations as a therapeutic agent. Based on results from animal studies, the effective therapeutic concentration of sCR1 will be quite high. In addition, the clearance of sCR1 from the bloodstream is surprisingly rapid. Also, because sCR1 blocks both the classical and alternative complement cascades, host defense will be compromised.

Further evidence of the importance of inappropriate complement activation in disease pathology has been provided by the use of anti-C5 monoclonal antibodies. Anti-C5 antibodies have been shown to be beneficial in murine models of arthritis and immune complex nephritis. In an ex vivo model of cardiopulmonary bypass (CPB)-induced inflammation, administration of anti-human C5 monoclonal antibody inhibited leukocyte and platelet activation that normally occurs during such procedures.

Although anti-C5 antibodies have demonstrated efficacy in vivo, there are certain shortcomings of C5 as a therapeutic agent. Firstly, C5 is an abundant plasma protein (~85 µg/ml); therefore, high concentrations of an anti-C5 monoclonal antibody would be required to block C5 activity. In addition, it is important to note that this approach would not block the formation of C3a, another potent inflammatory mediator. There is accumulating evidence that C3a can initiate potentially detrimental events, including the release of proinflammatory cytokines and prostaglandins from monocytes, histamine release from mast cells, and degranulation of eosinophils.

Available clinical data suggest that in many acute and chronic injury settings, complement activation is mediated predominantly by the alternative pathway. These findings indicate that it would be advantageous to specifically inhibit alternative pathway-mediated tissue damage in a variety of injury settings, such as post-cardiopulmonary bypass inflammation, myocardial infarction, reperfusion injury, stroke, rheumatoid arthritis, and thermal burns. This would leave aspects of the classical pathway intact to handle immune complex processing and aid in host defense against infection.

The key enzymatic step of the alternative pathway is mediated by the C3-convertase (C3bBb), which cleaves C3 to yield C3a and C3b. The alternative pathway-specific protein, properdin, has been speculated to play a role in the regulation of the alternative pathway by virtue of its ability to increase the half-life of the C3 and C5 convertase complexes (C3bBb and C3bBbC3b, respectively).

There is a need in the art for agents that reduce inflammation and other disorders that are mediated, at least in part, by the alternative complement pathway. The present invention addresses this need.

Literature

Gupta-Bansal et al. (2000) *Mol. Immunol.* 37:191-201; Published U.S. Patent Application No. 20020015701; U.S. Pat. No. 5,770,429; U.S. Pat. No. 6,162,963; U.S. Pat. No. 6,150,584; U.S. Pat. No. 6,114,598; U.S. Pat. No. 6,075,181; Green (1999) *J. Immunol. Methods* 231:11-23; Wells (2000) *Chem Biol* 7:R185-6; and Davis et al. (1999) Cancer Metastasis Rev 18(4):421-5; Vuagnat et al. (2000) *Mol. Immunol.* 37:467-478; Perdikoulis et al. (2001) *Biochim. Biophys. Acta* 1548:265-277.

SUMMARY OF THE INVENTION

The present invention is related to antibodies directed to the antigen properdin and uses of such antibodies. In particular, in accordance with the present invention, there are provided fully human monoclonal antibodies directed to the antigen properdin. Nucleotide sequences encoding, and polypeptides comprising, heavy and light chain immunoglobulin molecules, particularly sequences corresponding to contiguous heavy and light chain sequences spanning the framework regions (FR's) and/or complementarity determining regions (CDR's), specifically from FR1 through FR4 or CDR1 through CDR3, are provided. Hybridomas or other cell lines expressing such immunoglobulin molecules and monoclonal antibodies are also provided.

BRIEF DESCRIPTION OF THE DRAWINGS

FIG. 12 depicts FR1, CDR1, FR2, CDR2, FR3, CDR3, and J regions of exemplary subject antibody light chain variable regions, in comparison with germline ("GL") amino acid sequences. A dash indicates amino acid identity to a give GL sequence; a # symbolizes a gap introduced into a GL sequence.

FIG. 13 compares nucleotide sequences at V-J junctions ("V sequence"; "J sequence"), the number of N sequences added; as well as the position and length of CDRs, and the CDR1, CDR2, and CDR3 amino acid sequences of various exemplary subject antibody light chain variable regions.

FIG. 14 depicts FR1, CDR1, FR2, CDR2, FR3, CDR3, and J regions of exemplary subject antibody heavy chain variable regions, in comparison with germline ("GL") amino acid sequences. A dash indicates amino acid identity to a give GL sequence; a # symbolizes a gap introduced into a GL sequence.

FIG. 15 compares nucleotide sequences at V-D-J junctions ("V sequence"; "D1 sequence"; and "J sequence"), the number of N sequences added; as well as the position and length of CDRs, and the CDR1, CDR2, and CDR3 amino acid sequences of various exemplary subject antibody heavy chain variable regions.

FIGS. 16A-F depict nucleotide sequences of light and heavy chains of exemplary subject antibodies.

FIGS. 17A-C depict amino acid sequences of light and heavy chains of exemplary subject antibodies.

DEFINITIONS

Figure 1:
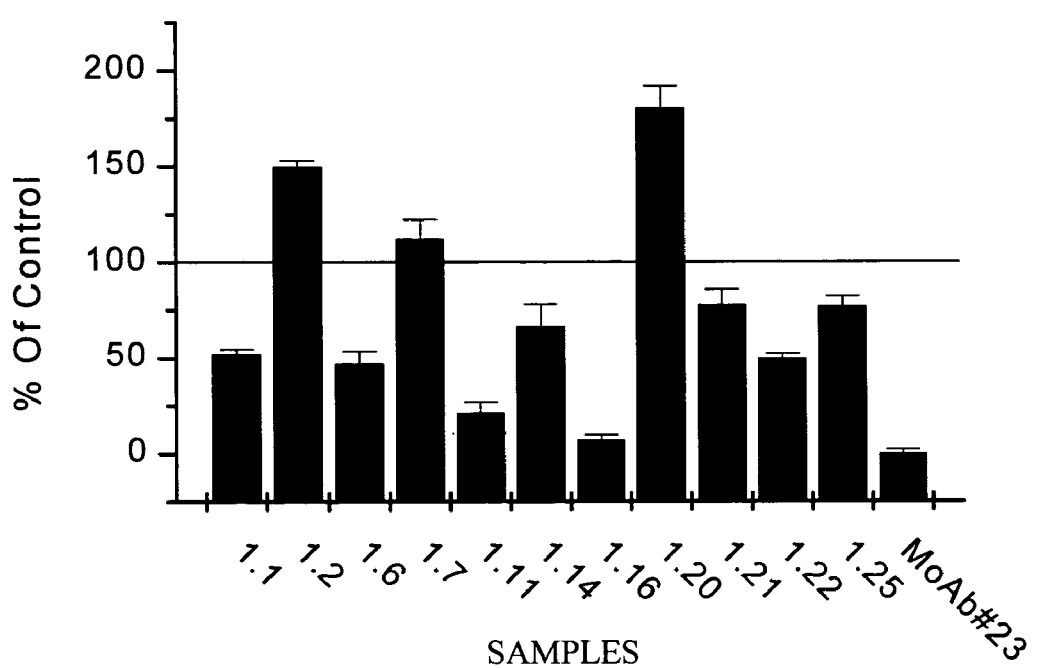
FIG. 1 depicts analysis of IgG2 antibodies in an LPS-activation C5b-9 assay.

The term "isolated polynucleotide" as used herein shall mean a polynucleotide of genomic, cDNA, or synthetic origin or some combination thereof, which by virtue of its origin the "isolated polynucleotide" (1) is not associated with all or a portion of a polynucleotide in which the "isolated polynucleotide" is found in nature, (2) is operably linked to a polynucleotide which it is not linked to in nature, or (3) does not occur in nature as part of a larger sequence.

The term "isolated protein" referred to herein means a protein of cDNA, recombinant RNA, or synthetic origin or some combination thereof, which by virtue of its origin, or source of derivation, the "isolated protein" (1) is not associated with proteins found in nature, (2) is free of other proteins from the same source, e.g. free of murine proteins, (3) is expressed by a cell from a different species, or (4) does not occur in nature.

The term "polypeptide" is used herein as a generic term to refer to native protein, fragments, or analogs of a polypeptide sequence. Hence, native protein, fragments, and analogs are species of the polypeptide genus. Preferred polypeptides in accordance with the invention comprise the human heavy chain immunoglobulin molecules including variable region amino acid sequences represented by FIGS. 17A-C (e.g., SEQ ID NOs:04, 08, 12, 16, and 20) and the human kappa light chain immunoglobulin molecules including variable region amino acid sequences represented by FIGS. 17A-C (e.g., SEQ ID NOs:02, 06, 10, 14, and 18), as well as antibody molecules formed by combinations comprising the heavy chain immunoglobulin molecules with light chain immunoglobulin molecules, such as the kappa light chain immunoglobulin molecules, and vice versa, as well as fragments and analogs thereof.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally-occurring.

The term "operably linked" as used herein refers to positions of components so described are in a relationship permitting them to function in their intended manner. A control sequence "operably linked" to a coding sequence is ligated in such a way that expression of the coding sequence is achieved under conditions compatible with the control sequences.

The term "control sequence" as used herein refers to polynucleotide sequences which are necessary to effect the expression and processing of coding sequences to which they are ligated. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences.

The term "polynucleotide" as referred to herein means a polymeric form of nucleotides of at least 10 bases in length, either ribonucleotides or deoxynucleotides or a modified form of either type of nucleotide. The term includes single and double stranded forms of DNA.

The term "oligonucleotide" referred to herein includes naturally occurring, and modified nucleotides linked together by naturally occurring, and non-naturally occurring oligonucleotide linkages. Oligonucleotides are a polynucleotide subset generally comprising a length of 200 bases or fewer. Preferably oligonucleotides are 10 to 60 bases in length and most preferably 12, 13, 14, 15, 16, 17, 18, 19, or 20 to 40 bases in length. Oligonucleotides are usually single stranded, e.g. for probes; although oligonucleotides may be double stranded, e.g. for use in the construction of a gene mutant. Oligonucleotides of the invention can be either sense or antisense oligonucleotides.

The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes oligonucleotides linkages such as phosphorothioate, phosphorodithioate, phosphoroselenoate, phosphorodiselenoate, phosphoroanilothioate, phoshoraniladate, phosphoroamidate, and the like. See e.g., LaPlanche et al. *Nucl. Acids Res.* 14:9081 (1986); Stec et al. *J. Am. Chem. Soc.* 106:6077 (1984); Stein et al. *Nucl. Acids Res.* 16:3209 (1988); Zon et al. *Anti-Cancer Drug Design* 6:539 (1991); Zon et al. *Oligonucleotides and Analogues: A Practical Approach*, pp. 87-108 (F. Eckstein, Ed., Oxford University Press, Oxford England (1991)); Stec et al. U.S. Pat. No. 5,151,510; Uhlmann and Peyman *Chemical Reviews* 90:543 (1990), the disclosures of which are hereby incorporated by reference. An oligonucleotide can include a label for detection, if desired.

The term "selectively hybridize" referred to herein means to detectably and specifically bind. Polynucleotides, oligonucleotides and fragments thereof in accordance with the invention selectively hybridize to nucleic acid strands under hybridization and wash conditions that minimize appreciable amounts of detectable binding to nonspecific nucleic acids. High stringency conditions can be used to achieve selective hybridization conditions as known in the art and discussed herein. Generally, the nucleic acid sequence homology between the polynucleotides, oligonucleotides, and fragments of the invention and a nucleic acid sequence of interest will be at least 80%, and more typically with preferably increasing homologies of at least 85%, 90%, 95%, 99%, and 100%. Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred.

Alternatively and preferably, two protein sequences (or polypeptide sequences derived from them of at least 30 amino acids in length) are homologous, as this term is used herein, if they have an alignment score of at more than 5 (in standard deviation units) using the program ALIGN with the mutation data matrix and a gap penalty of 6 or greater. See Dayhoff, M. O., in *Atlas of Protein Sequence and Structure*, pp. 101-110 (Volume 5, National Biomedical Research Foundation (1972)) and Supplement 2 to this volume, pp. 1-10. The two sequences or parts thereof are more preferably homologous if their amino acids are greater than or equal to 50% identical when optimally aligned using the ALIGN program. The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The following terms are used to describe the sequence relationships between two or more polynucleotide or amino acid sequences: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing or may comprise a complete cDNA or gene sequence. Generally, a reference sequence is at least 18 nucleotides or 6 amino acids in length, frequently at least 24 nucleotides or 8 amino acids in length, and often at least 48 nucleotides or 16 amino acids in length. Since two polynucleotides or amino acid sequences may each (1) comprise a sequence (i.e., a portion of the complete polynucleotide or amino acid sequence) that is similar between the two molecules, and (2) may further comprise a sequence that is divergent between the two polynucleotides or amino acid sequences, sequence comparisons between two (or more) molecules are typically performed by comparing sequences of the two molecules over a "comparison window" to identify and compare local regions of sequence similarity.

A "comparison window", as used herein, refers to a conceptual segment of at least 18 contiguous nucleotide positions or 6 amino acids wherein a polynucleotide sequence or amino acid sequence may be compared to a reference sequence of at least 18 contiguous nucleotides or 6 amino acid sequences and wherein the portion of the polynucleotide sequence in the comparison window may comprise additions, deletions, substitutions, and the like (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman *Adv. Appl. Math.* 2:482 (1981), by the homology alignment algorithm of Needleman and Wunsch *J. Mol. Biol.* 48:443 (1970), by the search for similarity method of Pearson and Lipman *Proc. Natl. Acad. Sci.* (*U.S.A.*) 85:2444 (1988), by computerized implementations of these algorithms (GAP, BESTFIT, FASTA, and TFASTA in the Wisconsin Genetics Software Package Release 7.0, (Genetics Computer Group, 575 Science Dr., Madison, Wis.), Geneworks, or MacVector software packages), or by inspection, and the best alignment (i.e., resulting in the highest percentage of homology over the comparison window) generated by the various methods is selected.

As used herein, the twenty conventional amino acids and their abbreviations follow conventional usage. See *Immunology-A Synthesis* (2nd Edition, E. S. Golub and D. R. Gren, Eds., Sinauer Associates, Sunderland, Mass. (1991)), which is incorporated herein by reference. Stereoisomers (e.g., D-amino acids) of the twenty conventional amino acids, unnatural amino acids such as α-, α-disubstituted amino acids, N-alkyl amino acids, lactic acid, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the lefthand direction is the amino terminal direction and the righthand direction is the carboxy-terminal direction, in accordance with standard usage and convention.

Similarly, unless specified otherwise, the lefthand end of single-stranded polynucleotide sequences is the 5' end; the lefthand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity, and most preferably at least 99 percent sequence identity. Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, glutamic-aspartic, and asparagine-glutamine.

As discussed herein, minor variations in the amino acid sequences of antibodies or immunoglobulin molecules are contemplated as being encompassed by the present invention, providing that the variations in the amino acid sequence maintain at least 75%, more preferably at least 80%, 90%, 95%, and most preferably 99%. In particular, conservative amino acid replacements are contemplated. Conservative replacements are those that take place within a family of amino acids that are related in their side chains. Genetically encoded amino acids are generally divided into families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cysteine, serine, threonine, tyrosine. More preferred families are: serine and threonine are aliphatic-hydroxy family; asparagine and glutamine are an amide-containing family; alanine, valine, leucine and isoleucine are an aliphatic family; and phenylalanine, tryptophan, and tyrosine are an aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site.

Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al. *Science* 253:164 (1991). Thus, the foregoing examples demonstrate that those of skill in the art can recognize sequence motifs and structural conformations that may be used to define structural and functional domains in accordance with the invention.

Preferred amino acid substitutions are those which: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in *Proteins, Structures and Molecular Principles* (Creighton, Ed., W. H. Freeman and Company, New York (1984)); *Introduction to Protein Structure* (C. Branden and J. Tooze, eds., Garland Publishing, New York, N.Y. (1991)); and Thornton et at. *Nature* 354:105 (1991), which are each incorporated herein by reference.

The term "polypeptide fragment" as used herein refers to a polypeptide that has an amino-terminal and/or carboxyl-terminal deletion, but where the remaining amino acid sequence is identical to the corresponding positions in the naturally-occurring sequence deduced, for example, from a full-length cDNA sequence. Fragments typically are at least 5, 6, 8 or 10 amino acids long, preferably at least 14 amino acids long, more preferably at least 20 amino acids long, usually at least 50 amino acids long, and even more preferably at least 70 amino acids long. The term "analog" as used herein refers to polypeptides which are comprised of a segment of at least 25 amino acids that has substantial identity to a portion of a deduced amino acid sequence and which has at least one biological activity of a corresponding native polypeptide. Typically, polypeptide analogs comprise a conservative amino acid substitution (or addition or deletion) with respect to the naturally-occurring sequence. Analogs typically are at least 20 amino acids long, preferably at least 50 amino acids long or longer, and can often be as long as a full-length naturally-occurring polypeptide.

Peptide analogs are commonly used in the pharmaceutical industry as non-peptide drugs with properties analogous to those of the template peptide. These types of non-peptide compound are termed "peptide mimetics" or "peptidomimetics". Fauchere, *J. Adv. Drug Res.* 15:29 (1986); Veber and Freidinger *TINS* p. 392 (1985); and Evans et al. *J. Med. Chem.* 30:1229 (1987), which are incorporated herein by reference. Such compounds are often developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from the group consisting of: —CH$_2$NH—, —CH$_2$S—, —CH$_2$—CH$_2$—, —CH=CH-(cis and trans), —COCH$_2$—, —CH(OH)CH$_2$—, and —CH$_2$SO—, by methods well known in the art. Systematic substitution of one or more amino acids of a consensus sequence with a D-amino acid of the same type (e.g., D-lysine in place of L-lysine) may be used to generate more stable peptides. In addition, constrained peptides comprising a consensus sequence or a substantially identical consensus sequence variation may be generated by methods known in the art (Rizo and Gierasch *Ann. Rev. Biochem.* 61:387 (1992), incorporated herein by reference); for example, by adding internal cysteine residues capable of forming intramolecular disulfide bridges which cyclize the peptide.

"Antibody" or "antibody peptide(s)" refer to an intact antibody, or a binding fragment thereof that competes with the intact antibody for specific binding. Binding fragments are produced by recombinant DNA techniques, or by enzymatic or chemical cleavage of intact antibodies. Binding fragments include Fab, Fab', F(ab')$_2$, Fv, and single-chain antibodies. An antibody other than a "bispecific" or "bifunctional" antibody is understood to have each of its binding sites identical. An antibody substantially inhibits adhesion of a polypeptide to a specific binding partner when an excess of antibody reduces the quantity of the polypeptide bound to the specific binding partner by at least about 20%, 40%, 60% or 80%, and more usually greater than about 85% (as measured in an in vitro competitive binding assay).

The term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. An antibody is said to specifically bind an antigen when the dissociation constant is $\leq 1$ µM, preferably $\leq 100$ nM and most preferably $\leq 10$ nM.

The term "agent" is used herein to denote a chemical compound, a mixture of chemical compounds, a biological macromolecule, or an extract made from biological materials.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). In certain situations, the label or marker can also be therapeutic. Various methods of labeling polypeptides and glycoproteins are known in the art and may be used. Examples of labels for polypeptides include, but are not limited to, the following: radioisotopes or radionuclides (e.g., $^3$H, $^{14}$C, $^{15}$N, $^{35}$S, $^{90}$Y, $^{99}$Tc, $^{111}$In, $^{125}$I, $^{131}$I), fluorescent labels (e.g., FITC, rhodamine, lanthanide phosphors), enzymatic labels (e.g., horseradish peroxidase, β-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance.

The term "pharmaceutical agent or drug" as used herein refers to a chemical compound or composition capable of inducing a desired therapeutic effect when properly administered to a patient. Other chemistry terms herein are used according to conventional usage in the art, as exemplified by *The McGraw-Hill Dictionary of Chemical Terms* (Parker, S., Ed., McGraw-Hill, San Francisco (1985)), incorporated herein by reference).

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

The terms "patient," "mammalian host," and the like are used interchangeably herein, and refer to mammals, including human and veterinary subjects.

The term "sequence identity" means that two polynucleotide or amino acid sequences are identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T, C, G, U, or I) or residue occurs in both sequences to yield the number of matched positions, dividing the number of matched positions by the total number of positions in the comparison window (i.e., the window size), and multiplying the result by 100 to yield the percentage of sequence identity. The terms "substantial identity" as used herein denotes a characteristic of a polynucleotide or amino acid sequence, wherein the polynucleotide or amino acid comprises a sequence that has at least 85 percent sequence identity, preferably at least 90 to 95 percent sequence identity, more usually at least 99 percent sequence identity as compared to a reference sequence over a comparison window of at least 18 nucleotide (6 amino acid) positions, frequently over a window of at least 24-48 nucleotide (8-16 amino acid) positions, wherein the percentage of sequence identity is calculated by comparing the reference sequence to the sequence which may include deletions or additions which total 20 percent or less of the reference sequence over the comparison window. The reference sequence may be a subset of a larger sequence.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a mammal, particularly in a human, and includes: (a) preventing the disease from occurring in a subject which may be predisposed to the disease or at risk of acquiring the disease but has not yet been diagnosed as having it; (b) inhibiting the disease, i.e., arresting its development; and (c) relieving the disease, i.e., causing regression of the disease.

The term "a disease or disorder associated with the alternative complement pathway," as used herein, refers to a disease or disorder caused, directly or indirectly, by activation of the alternative complement pathway, a disease or disorder that is mediated, directly or indirectly, by one or more components of the alternative complement pathway, or a product generated by the alternative complement pathway. The term also refers to a disease or disorder that is exacerbated by one or more components of the alternative complement pathway, or a product generated by the alternative complement pathway.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. *Molecular Cloning: A Laboratory Manual* (2d ed., Cold Spring Harbor Laboratory Press, Cold Spring Harbor, N.Y. (1989)), which is incorporated herein by reference. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

It must be noted that as used herein and in the appended claims, the singular forms "a", "and", and "the" include plural referents unless the context clearly dictates otherwise. Thus, for example, reference to "an anti-properdin antibody" includes a plurality of such antibody and reference to "the disease" includes reference to one or more diseases and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

The present invention provides fully human anti-properdin antibodies, and compositions comprising the antibodies. A subject antibody is produced by an antibody-producing cell of a XenoMouse®, a genetically modified mouse that produces antibodies having amino acid sequences of human antibodies, e.g., human framework (FR) and human constant region amino acid sequences.

XenoMouse® genetically modified mouse strains are genetically engineered mice in which the murine IgH and Igk loci have been functionally replaced by their Ig counterparts on yeast artificial YAC transgenes. These human Ig transgenes can carry the majority of the human variable repertoire and can undergo class switching from IgM to IgG isotypes. The immune system of the xenomouse recognizes administered human antigens as foreign and produces a strong humoral response. The use of XenoMouse® in conjunction with well-established hybridomas techniques, results in fully human IgG mAbs with sub-nanomolar affinities for human antigens (see U.S. Pat. No. 5,770,429, entitled "Transgenic non-human animals capable of producing heterologous antibodies"; U.S. Pat. No. 6,162,963, entitled "Generation of Xenogenetic antibodies"; U.S. Pat. No. 6,150,584, entitled "Human antibodies derived from immunized xenomice"; U.S. Pat. No. 6,114,598, entitled Generation of xenogeneic antibodies; and U.S. Pat. No. 6,075,181, entitled "Human antibodies derived from immunized xenomice"; for reviews, see Green, Antibody engineering via genetic engineering of the mouse: XenoMouse® strains are a vehicle for the facile generation of therapeutic human monoclonal antibodies, *J. Immunol. Methods* 231:11-23, 1999; Wells, Eek, a XenoMouseg: Abgenix, Inc., Chem Biol August 2000; 7(8):R185-6; and Davis et al., Transgenic mice as a source of fully human antibodies for the treatment of cancer Cancer Metastasis Rev 1999; 18(4):421-5).

A subject antibody is useful in a variety of therapeutic methods. A subject anti-properdin antibody is useful in therapeutic methods for the treatment of diseases mediated, directly or indirectly, by a component of the alternative complement pathway, and/or by a factor generated following activation of the alternative complement pathway.

A subject anti-properdin antibody avoids problems associated with rodent antibodies, i.e., adverse reactions in humans, such as hypersensitivity reactions, including urticaria, dyspnea, hypotension, anaphylaxis, and the like.

Anti-Properdin Antibodies

The present invention provides fully human anti-properdin antibodies, and compositions comprising the antibodies. A subject antibody is produced by an antibody-producing cell of a XenoMouse®, a genetically modified mouse that produces antibodies having amino acid sequences of human antibodies, e.g., human framework (FR) and human constant region amino acid sequences.

Properdin

Properdin polypeptides are known in the art. For example, the amino acid sequences of human and mouse properdin are found in the GenBank database under the following accession numbers: for human properdin, see, e.g., GenBank Accession Nos. AAA36489, NP_002612, AAH15756, AAP43692, S29126, CAA40914; for mouse properdin, see, e.g., GenBank Accession Nos. P11680, and S05478. Human properdin is a 469 amino acid protein that includes a signal peptide (amino acids 1-28), and six, non-identical thrombospondin type 1 repeats (TSR) of about 60 amino acids each, as follows: amino acids 80-134 (TSR1), amino acids 139-191 (TSR2), amino acids 196-255 (TSR3), amino acids 260-313 (TSR4), amino acids 318-377 (TSR5), and amino acids 382-462 (TSR6). Properdin is formed by oligomerization of a rod-like monomer into cyclic dimers, trimers, and tetramers.

Antibody Activities

A subject anti-properdin antibody exhibits one or more of the following activities: (1) inhibits binding of properdin to C3b; (2) inhibits oligomerization of properdin monomers; (3) reduces the level and/or production of a component of the alternative complement pathway, or a factor produced by action of a component of the alternative complement pathway; (4) reduces formation of membrane attack complex (MAC); (5) reduces formation of anaphylatoxins, e.g., C3a and/or C5a; and (6) reduces formation of C3c.

In some embodiments, a subject antibody binds to an epitope within a TSR of properdin, e.g., a subject antibody binds to an epitope within TSR1, TSR2, TSR3, TSR4, TSR5, or TSR6. In some embodiments, a subject antibody binds to two or more TSRs of a properdin polypeptide, e.g., where an epitope is shared between or among TSRs, and where shared epitopes may, but need not, be identical in amino acid sequence.

In some embodiments, a subject antibody inhibits binding of properdin to C3b. In these embodiments, a subject antibody effects an at least about 20%, at least about 30%, at least about 40%, at least about 50%, at least about 60%, at least about 70%, at least about 80%, at least about 90%, or more, inhibition of binding of properdin to C3b.

Whether a subject antibody inhibits properdin/C3b binding can be determined by using any of a number of well-known assays to detect protein-protein binding, including, but not limited to, a fluorescence resonance energy transfer (FRET) assay, a bioluminescence resonance energy transfer (BRET) assay, a fluorescence quenching assay; a fluorescence anisotropy assay; an immunological assay; and an assay involving binding of a detectably labeled protein to an immobilized protein. Immunological assays, and assays involving binding of a detectably labeled protein to an immobilized protein can be arranged in a variety of ways. For example, C3b is immobilized on a solid support, and binding of properdin to C3b in the presence of a test antibody is detected. The properdin can be detectably labeled, either directly or indirectly, as described in Example 1.

A subject antibody inhibits the level and/or production in a mammalian host of one or more components of the alternative complement pathway and/or one or more factors produced by action of one or more components of the alternative complement pathway. Exemplary, non-limiting examples of components and factors that are reduced include MAC (C5b-9), C3c, and anaphylatoxins, such as C3a and C5a, and the like. A subject antibody reduces the levels of one or more components of the alternative complement pathway and/or one or more factors produced by action of one or more components of the alternative complement pathway by at least about 20%, at least about 30%, at least about 40%, at least about 50%, at least about 60%, at least about 70%, at least about 80%, at least about 90%, or more, compared to the level of the component or factor in the absence of the subject antibody.

In some embodiments, a subject antibody reduces the level and/or production of MAC in a mammalian host. In these embodiments, a subject antibody reduces formation of MAC by at least about 20%, at least about 30%, at least about 40%, at least about 50%, at least about 60%, at least about 70%, at least about 80%, at least about 90%, or more, compared to the level of MAC in a mammalian host not treated with the antibody. Whether a subject antibody reduces formation of MAC can be readily determined using any known assay, e.g., an in vitro assay such as described in Example 1. For example, human serum is contacted, in the presence or absence of a test antibody, with immobilized lipopolysaccharide (LPS) to activate complement, which results in covalent attachment of C5b-9 to the immobilized LPS. LPS-bound C5b-9 is detected using an antibody specific for C5b-9.

In some embodiments, a subject antibody reduces the level and/or production of an anaphylatoxin, such as C3a and C5a, in a mammalian host. In these embodiments, a subject antibody reduces formation of an anaphylatoxin by at least about 20%, at least about 30%, at least about 40%, at least about 50%, at least about 60%, at least about 70%, at least about 80%, at least about 90%, or more, compared to the level of an anaphylatoxin in a mammalian host not treated with the antibody. Whether the level of an anaphylatoxin is reduced is readily determined using any known method, including the methods described in the Examples.

Detectable labels

In some embodiments, a subject antibody is detectably labeled. Detectable labels include, but are not limited to, fluorescent proteins; enzymes (e.g., β-galactosidase, luciferase, horse radish peroxidase, etc.); radioisotopes, e.g., $^{32}P$, $^{35}S$, $^{3}H$; etc.; fluorescers, e.g., fluorescein isothiocyanate (FITC), rhodamine, Texas Red, phycoerythrin, allophycocyanin, and fluorescent proteins; chemiluminescers; specific binding molecules; particles, e.g. magnetic particles, and the like. Specific binding molecules include pairs, such as biotin and streptavidin, digoxin and antidigoxin etc. Suitable fluorescent proteins include those described in Matz et al. ((1999) *Nature Biotechnology* 17:969-973), a green fluorescent protein from any species or a derivative thereof; e.g., a GFP from another species such as *Renilla reniformis, Renilla mulleri*, or *Ptilosarcus guernyi*, as described in, e.g., WO 99/49019 and Peelle et al. (2001) *J. Protein Chem.* 20:507-519; "humanized" recombinant GFP (hrGFP) (Stratagene); a GFP from *Aequoria victoria* or fluorescent mutant thereof, e.g., as described in U.S. Pat. Nos. 6,066,476; 6,020,192; 5,985,577; 5,976,796; 5,968,750; 5,968,738; 5,958,713; 5,919,445; 5,874,304.

Antibody Structure

The basic antibody structural unit is known to comprise a tetramer. Each tetramer is composed of two identical pairs of polypeptide chains, each pair having one "light" (about 25-kDa) and one "heavy" chain (about 50-70 kDa). The amino-terminal portion of each chain includes a variable region of about 100 to 110 or more amino acids primarily responsible for antigen recognition. The carboxyl-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgA, and IgE, respectively. Within light and heavy chains, the variable and constant regions are joined by a "J" region of about 12 or more amino acids, with the heavy chain also including a "D" region of about 10 more amino acids. See generally, *Fundamental Immunology* Ch. 7 (Paul, W., ed., 2nd ed. Raven Press, N.Y. (1989)) (incorporated by reference in its entirety for all purposes). The variable regions of each light/heavy chain pair form the antibody binding site.

Thus, an intact antibody has two binding sites. Except in bifunctional or bispecific antibodies, the two binding sites are the same.

The chains all exhibit the same general structure of relatively conserved framework regions (FR) joined by three hyper variable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat *Sequences of Proteins of Immunological Interest* (National Institutes of Health, Bethesda, Md. (1987 and 1991)), or Chothia & Lesk *J. Mol. Biol.* 196:901-917 (1987); Chothia et al. *Nature* 342:878-883 (1989).

In some embodiments, a subject antibody comprises a light chain comprising an amino acid sequence having at least about 80%, at least about 85%, at least about 90%, at least about 95%, at least about 98%, or at least about 99% amino acid sequence identity to any one of SEQ ID NOs:02, 06, 10, 14, and 18, as shown in FIGS. 17A-C. In some embodiments, a subject antibody comprises a light chain comprising an amino acid sequence that differs from any one of SEQ ID NOs:02, 06, 10, 14, and 18 by only one, two, three, four, five, six, seven, eight, nine, or ten amino acids. Those of ordinary skill in the art can readily determine which amino acids in a light chain variable region can be altered. For example, by comparing the amino acid sequences of light chain variable regions of antibodies with the same specificity, those skilled in the art can determine which amino acids can be altered without altering the specificity. See, e.g., FIG. 12 for a comparison of CDR amino acid sequences of exemplary anti-properdin antibody light chains. Furthermore, whether the specificity is altered can be readily determined using an antigen binding assay. In some embodiments, a subject antibody comprises a light chain comprising an amino acid sequence as set forth in any one of SEQ ID NOs:02, 06, 10, 14, and 18.

In some embodiments, a subject antibody comprises a heavy chain comprising an amino acid sequence having at least about 80%, at least about 85%, at least about 90%, at least about 95%, at least about 98%, or at least about 99% amino acid sequence identity to any one of SEQ ID NOs:04, 08, 12, 16, or 20, as shown in FIGS. 17A-C. In some embodiments, a subject antibody comprises a heavy chain comprising an amino acid sequence that differs from any one of SEQ ID NOs:04, 08, 12, 16, or 20 by only one, two, three, four, five, six, seven, eight, nine, or ten amino acids. Those of ordinary skill in the art can readily determine which amino acids in a heavy chain variable region can be altered. For example, by comparing the amino acid sequences of heavy chain variable regions of antibodies with the same specificity, those skilled in the art can determine which amino acids can be altered without altering the specificity. See, e.g., FIG. 14 for a comparison of CDR amino acid sequences of exemplary anti-properdin antibody heavy chains. Furthermore, whether the specificity is altered can be readily determined using an antigen binding assay. In some embodiments, a subject antibody comprises a heavy chain comprising an amino acid sequence as set forth in any one of SEQ ID NOs:04, 08, 12, 16, or 20.

In some embodiments, a subject antibody comprises a light chain comprising an amino acid sequence as set forth in any one of SEQ ID NOs:02, 06, 10, 14, and 18; and a heavy chain comprising an amino acid sequence as set forth in any one of SEQ ID NOs:04, 08, 12, 16, or 20. In some embodiments, a subject antibody comprises a light chain comprising an amino acid sequence as set forth in SEQ ID NO:02 and a heavy chain comprising an amino acid sequence as set forth in SEQ ID NO:04. In some embodiments, a subject antibody comprises a light chain comprising an amino acid sequence as set forth in SEQ ID NO:06 and a heavy chain comprising an amino acid sequence as set forth in SEQ ID NO:08. In some embodiments, a subject antibody comprises a light chain comprising an amino acid sequence as set forth in SEQ ID NO:10 and a heavy chain comprising an amino acid sequence as set forth in SEQ ID NO:12. In some embodiments, a subject antibody comprises a light chain comprising an amino acid sequence as set forth in SEQ ID NO:14 and a heavy chain comprising an amino acid sequence as set forth in SEQ ID NO:16. In some embodiments, a subject antibody comprises a light chain comprising an amino acid sequence as set forth in SEQ ID NO:18 and a heavy chain comprising an amino acid sequence as set forth in SEQ ID NO:20.

A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann *Clin. Exp. Immunol.* 79: 315-321 (1990), Kostelny et al. *J. Immunol.* 148:1547-1553 (1992). Production of bispecific antibodies can be a relatively labor intensive process compared with production of conventional antibodies and yields and degree of purity are generally lower for bispecific antibodies. Bispecific antibodies do not exist in the form of fragments having a single binding site (e.g., Fab, Fab', and Fv).

Human Antibodies and Humanization of Antibodies

Human antibodies avoid certain of the problems associated with antibodies that possess murine or rat variable and/or constant regions. The presence of such murine or rat derived proteins can lead to the rapid clearance of the antibodies or can lead to the generation of an immune response against the antibody by a patient. In order to avoid the utilization of murine or rat derived antibodies, it has been postulated that one can develop humanized antibodies or generate fully human antibodies through the introduction of human antibody function into a rodent so that the rodent would produce fully human antibodies.

Human Antibodies

The ability to clone and reconstruct megabase-sized human loci in YACs and to introduce them into the mouse germline provides a powerful approach to elucidating the functional components of very large or crudely mapped loci as well as generating useful models of human disease. Furthermore, the utilization of such technology for substitution of mouse loci with their human equivalents could provide unique insights into the expression and regulation of human gene products during development, their communication with other systems, and their involvement in disease induction and progression.

An important practical application of such a strategy is the "humanization" of the mouse humoral immune system. Introduction of human immunoglobulin (Ig) loci into mice in which the endogenous Ig genes have been inactivated offers the opportunity to study the mechanisms underlying programmed expression and assembly of antibodies as well as their role in B-cell development. Furthermore, such a strategy could provide an ideal source for production of fully human monoclonal antibodies (Mabs)—an important milestone towards fulfilling the promise of antibody therapy in human disease. Fully human antibodies are expected to minimize the immunogenic and allergic responses intrinsic to mouse or mouse-derivatized Mabs and thus to increase the efficacy and safety of the administered antibodies. The use of fully human antibodies can be expected to provide a substantial advantage in the treatment of chronic and recurring human diseases, such as inflammation, autoimmunity, and cancer, which require repeated antibody administrations.

One approach towards this goal was to engineer mouse strains deficient in mouse antibody production with large fragments of the human Ig loci in anticipation that such mice would produce a large repertoire of human antibodies in the absence of mouse antibodies. Large human Ig fragments would preserve the large variable gene diversity as well as the proper regulation of antibody production and expression. By exploiting the mouse machinery for antibody diversification and selection and the lack of immunological tolerance to human proteins, the reproduced human antibody repertoire in these mouse strains should yield high affinity antibodies against any antigen of interest, including human antigens. Using the hybridoma technology, antigen-specific human Mabs with the desired specificity could be readily produced and selected.

This general strategy was demonstrated in connection with our generation of the first XenoMouse™ strains as published in 1994. See Green et al. Nature Genetics 7:13-21 (1994). The XenoMouse™ strains were engineered with yeast artificial chromosomes (YACs) containing 245 kb and 190 kb-sized germline configuration fragments of the human heavy chain locus and kappa light chain locus, respectively, which contained core variable and constant region sequences. Id. The human Ig containing YACs proved to be compatible with the mouse system for both rearrangement and expression of antibodies and were capable of substituting for the inactivated mouse Ig genes. This was demonstrated by their ability to induce B-cell development, to produce an adult-like human repertoire of fully human antibodies, and to generate antigen-specific human Mabs. These results also suggested that introduction of larger portions of the human Ig loci containing greater numbers of V genes, additional regulatory elements, and human Ig constant regions might recapitulate substantially the full repertoire that is characteristic of the human humoral response to infection and immunization. The work of Green et al. was recently extended to the introduction of greater than approximately 80% of the human antibody repertoire through introduction of megabase sized, germline configuration YAC fragments of the human heavy chain loci and kappa light chain loci, respectively, to produce XenoMouse™ mice. See Mendez et al. Nature Genetics 15:146-156 (1997) and U.S. patent application Ser. No. 08/759,620, filed Dec. 3, 1996, the disclosures of which are hereby incorporated by reference.

Such approach is further discussed and delineated in U.S. Pat. Nos. 6,162,963, 6,150,584, 6,114,598, 6,075,181, and 5,939,598 and Japanese Patent Nos. 3 068 180 B2, 3 068 506 B2, and 3 068 507 B2. See also Mendez et al. Nature Genetics 15:146-156 (1997) and Green and Jakobovits J. Exp. Med. 188:483-495 (1998). See also European Patent No., EP 0 463 151 B 1, grant published Jun. 12, 1996, International Patent Application No., WO 94/02602, published Feb. 3, 1994, International Patent Application No., WO 96/34096, published Oct. 31, 1996, WO 98/24893, published Jun. 11, 1998, WO 00/76310, published Dec. 21, 2000. The disclosures of each of the above-cited patents, applications, and references are hereby incorporated by reference in their entirety.

In an alternative approach, others, including GenPharm International, Inc., have utilized a "minilocus" approach. In the minilocus approach, an exogenous Ig locus is mimicked through the inclusion of pieces (individual genes) from the Ig locus. Thus, one or more $V_H$ genes, one or more $D_H$ genes, one or more $J_H$ genes, a mu constant region, and a second constant region (preferably a gamma constant region) are formed into a construct for insertion into an animal. This approach is described in U.S. Pat. No. 5,545,807 to Surani et al. and U.S. Pat. Nos. 5,545,806, 5,625,825, 5,625,126, 5,633,425, 5,661, 016, 5,770,429, 5,789,650, 5,814,318, 5,877,397, 5,874,299, and 6,255,458 each to Lonberg and Kay, U.S. Pat. Nos. 5,591, 669 and 6,023.010 to Krimpenfort and Berns, U.S. Pat. Nos. 5,612,205, 5,721,367, and 5,789,215 to Berns et al., and U.S. Pat. No. 5,643,763 to Choi and Dunn, and GenPharm International U.S. patent application Ser. Nos. 07/574,748, filed Aug. 29, 1990, 07/575,962, filed Aug. 31, 1990, Ser. No. 07/810,279, filed Dec. 17, 1991, Ser. No. 07/853,408, filed Mar. 18, 1992, Ser. No. 07/904,068, filed Jun. 23, 1992, Ser. No. 07/990,860, filed Dec. 16, 1992, Ser. No. 08/053,131, filed Apr. 26, 1993, Ser. No. 08/096,762, filed Jul. 22, 1993, Ser. No. 08/155,301, filed Nov. 18, 1993, Ser. No. 08/161, 739, filed Dec. 3, 1993, Ser. No. 08/165,699, filed Dec. 10, 1993, Ser. No. 08/209,741, filed Mar. 9, 1994, the disclosures of which are hereby incorporated by reference. See also European Patent No. 0 546 073 B1, International Patent Application Nos. WO 92/03918, WO 92/22645, WO 92/22647, WO 92/22670, WO 93/12227, WO 94/00569, WO 94/25585, WO 96/14436, WO 97/13852, and WO 98/24884 and U.S. Pat. No. 5,981,175, the disclosures of which are hereby incorporated by reference in their entirety. See further Taylor et al., 1992, Chen et al., 1993, Tuaillon et al., 1993, Choi et al., 1993, Lonberg et al., (1994), Taylor et al., (1994), and Tuaillon et al., (1995), Fishwild et al., (1996), the disclosures of which are hereby incorporated by reference in their entirety.

The inventors of Surani et al., cited above and assigned to the Medical Research Counsel (the "MRC"), produced a transgenic mouse possessing an Ig locus through use of the minilocus approach. The inventors on the GenPharm International work, cited above, Lonberg and Kay, following the lead of the present inventors, proposed inactivation of the endogenous mouse Ig locus coupled with substantial duplication of the Surani et al. work.

An advantage of the minilocus approach is the rapidity with which constructs including portions of the Ig locus can be generated and introduced into animals. Commensurately, however, a significant disadvantage of the minilocus approach is that, in theory, insufficient diversity is introduced through the inclusion of small numbers of V, D, and J genes. Indeed, the published work appears to support this concern. B-cell development and antibody production of animals produced through use of the minilocus approach appear stunted. Therefore, research surrounding the present invention has consistently been directed towards the introduction of large portions of the Ig locus in order to achieve greater diversity and in an effort to reconstitute the immune repertoire of the animals.

Kirin has also demonstrated the generation of human antibodies from mice in which, through microcell fusion, large pieces of chromosomes, or entire chromosomes, have been introduced. See European Patent Application Nos. 773 288 and 843 961, the disclosures of which are hereby incorporated by reference.

Human anti-mouse antibody (HAMA) responses have led the industry to prepare chimeric or otherwise humanized antibodies. While chimeric antibodies have a human constant region and a murine variable region, it is expected that certain human anti-chimeric antibody (HACA) responses will be observed, particularly in chronic or multi-dose utilizations of the antibody. Thus, it would be desirable to provide fully human antibodies against properdin in order to vitiate concerns and/or effects of HAMA or HACA response.

Humanization and Display Technologies

As was discussed above in connection with human antibody generation, there are advantages to producing antibodies with reduced immunogenicity. To a degree, this can be accomplished in connection with techniques of humanization and display techniques using appropriate libraries. It will be appreciated that murine antibodies or antibodies from other species can be humanized or primatized using techniques well known in the art. See e.g., Winter and Harris *Immunol Today* 14:43-46 (1993) and Wright et al. *Crit, Reviews in Immunol.* 12125-168 (1992). The antibody of interest may be engineered by recombinant DNA techniques to substitute the CH1, CH2, CH3, hinge domains, and/or the framework domain with the corresponding human sequence (see WO 92/02190 and U.S. Pat. Nos. 5,530,101, 5,585,089, 5,693, 761, 5,693,792, 5,714,350, and 5,777,085). Also, the use of Ig cDNA for construction of chimeric immunoglobulin genes is known in the art (Liu et al. *P.N.A.S.* 84:3439 (1987) and *J. Immunol.* 139:3521 (1987)). mRNA is isolated from a hybridoma or other cell producing the antibody and used to produce cDNA. The cDNA of interest may be amplified by the polymerase chain reaction using specific primers (U.S. Pat. Nos. 4,683,195 and 4,683,202). Alternatively, a library is made and screened to isolate the sequence of interest. The DNA sequence encoding the variable region of the antibody is then fused to human constant region sequences. The sequences of human constant regions genes may be found in Kabat et al. (1991) Sequences of Proteins of Immunological Interest, N.I.H. publication no. 91-3242. Human C region genes are readily available from known clones. The choice of isotype will be guided by the desired effector functions, such as complement fixation, or activity in antibody-dependent cellular cytotoxicity. Preferred isotypes are IgG1, IgG3 and IgG4. Either of the human light chain constant regions, kappa or lambda, may be used. The chimeric, humanized antibody is then expressed by conventional methods.

Antibody fragments, such as Fv, F(ab')$_2$ and Fab may be prepared by cleavage of the intact protein, e.g. by protease or chemical cleavage. Alternatively, a truncated gene is designed. For example, a chimeric gene encoding a portion of the F(ab')$_2$ fragment would include DNA sequences encoding the CH1 domain and hinge region of the H chain, followed by a translational stop codon to yield the truncated molecule.

Consensus sequences of H and L J regions may be used to design oligonucleotides for use as primers to introduce useful restriction sites into the J region for subsequent linkage of V region segments to human C region segments. C region cDNA can be modified by site directed mutagenesis to place a restriction site at the analogous position in the human sequence.

Expression vectors include plasmids, retroviruses, YACs, EBV derived episomes, and the like. A convenient vector is one that encodes a functionally complete human CH or CL immunoglobulin sequence, with appropriate restriction sites engineered so that any VH or VL sequence can be easily inserted and expressed. In such vectors, splicing usually occurs between the splice donor site in the inserted J region and the splice acceptor site preceding the human C region, and also at the splice regions that occur within the human CH exons. Polyadenylation and transcription termination occur at native chromosomal sites downstream of the coding regions. The resulting chimeric antibody may be joined to any strong promoter, including retroviral LTRs, e.g. SV-40 early promoter, (Okayama et al. *Mol. Cell. Bio.* 3:280 (1983)), Rous sarcoma virus LTR (Gorman et al. *P.N.A.S.* 79:6777 (1982)), and moloney murine leukemia virus LTR (Grosschedl et al. *Cell* 41:885 (1985)). Also, as will be appreciated, native Ig promoters and the like may be used.

Further, human antibodies or antibodies from other species can be generated through display-type technologies, including, without limitation, phage display, retroviral display, ribosomal display, and other techniques, using techniques well known in the art and the resulting molecules can be subjected to additional maturation, such as affinity maturation, as such techniques are well known in the art. Wright and Harris, supra., Hanes and Plucthau *PNAS USA* 94:4937-4942 (1997) (ribosomal display), Parmley and Smith *Gene* 73:305-318 (1988) (phage display), Scott *TIBS* 17:241-245 (1992), Cwirla et al. *PNAS USA* 87:6378-6382 (1990), Russel et al. *Nucl. Acids Research* 21:1081-1085 (1993), Hoganboom et al. *Immunol. Reviews* 130:43-68 (1992), Chiswell and McCafferty *TIBTECH* 10:80-84 (1992), and U.S. Pat. No. 5,733,743. If display technologies are utilized to produce antibodies that are not human, such antibodies can be humanized as described above.

Using these techniques, antibodies can be generated to properdin-expressing cells, properdin itself, forms of properdin epitopes or peptides thereof, and expression libraries thereto (see e.g. U.S. Pat. No. 5,703,057) which can thereafter be screened as described above for the activities described above.

Additional Criteria for Antibody Therapeutics

As discussed herein, the function of a subject anti-properdin antibody appears important to at least a portion of its mode of operation. By function, we mean, by way of example, the activity of the anti-properdin antibody in inhibiting the alternative complement pathway, e.g., a subject anti-properdin antibody exhibits one or more of the following properties: (1) inhibits binding of properdin to C3b; (2) inhibits oligomerization of properdin monomers; (3) reduces formation of a component of the alternative complement pathway, or a factor produced by action of a component of the alternative complement pathway; (4) reduces formation of membrane attack complex (MAC); (5) reduces formation of anaphylatoxins, e.g., C3a and/or C5a; and (6) reduces formation of C3c.

A subject antibody will in some embodiments comprise an IgG₁ human heavy chain constant region; in other embodiments an IgG2 human heavy chain constant region; and in other embodiments an IgG3 human heavy chain constant region. It will be appreciated that antibodies that are generated need not initially possess such an isotype but, rather, the antibody as generated can possess any isotype and the antibody can be isotype switched thereafter using conventional techniques that are well known in the art. Such techniques include the use of direct recombinant techniques (see e.g., U.S. Pat. No. 4,816,397), cell-cell fusion techniques (see e.g., U.S. Pat. Nos. 5,916,771 and 6,207,418), among others.

In the cell-cell fusion technique, a myeloma or other cell line is prepared that possesses a heavy chain with any desired isotype and another myeloma or other cell line is prepared that possesses the light chain. Such cells can, thereafter, be fused and a cell line expressing an intact antibody can be isolated.

By way of example, the anti-properdin antibody discussed herein is a human anti-properdin IgG2 antibody. If such antibody possessed desired binding to a properdin polypeptide or epitope or fragment thereof, it could be readily isotype switched to generate a human IgM, human IgG1, or human IgG3 isotype, while still possessing the same variable region (which defines the antibody's specificity and some of its affinity).

Accordingly, as antibody candidates are generated that meet desired "structural" attributes as discussed above, they can generally be provided with at least certain of the desired "functional" attributes through isotype switching.

Design and Generation of Other Therapeutics

In accordance with the present invention and based on the activity of the antibodies that are produced and characterized herein with respect to inhibition of the alternative complement pathway, the design of other therapeutic modalities beyond antibody moieties is facilitated. Such modalities include, without limitation, advanced antibody therapeutics, such as bispecific antibodies, immunotoxins, and radiolabeled therapeutics, generation of peptide therapeutics, gene therapies, particularly intrabodies, antisense therapeutics, and small molecules.

In connection with the generation of advanced antibody therapeutics, where complement fixation is a desirable attribute, it may be possible to sidestep the dependence on complement for cell killing through the use of bispecifics, immunotoxins, or radiolabels, for example.

For example, in connection with bispecific antibodies, bispecific antibodies can be generated that comprise (i) two antibodies one with a specificity to properdin and another to a second molecule that are conjugated together, (ii) a single antibody that has one chain specific to properdin and a second chain specific to a second molecule, or (iii) a single chain antibody that has specificity to properdin and the other molecule. Such bispecific antibodies can be generated using techniques that are well known for example, in connection with (i) and (ii) see e.g., Fanger et al. *Immunol Methods* 4:72-81 (1994) and Wright and Harris, supra. and in connection with (iii) see e.g., Traunecker et al. *Int. J. Cancer (Suppl.)* 7:51-52 (1992). In each case, the second specificity can be made to the heavy chain activation receptors, including, without limitation, CD16 or CD64 (see e.g., Deo et al. 18:127 (1997)) or CD89 (see e.g., Valerius et al. *Blood* 90:4485-4492 (1997)). Bispecific antibodies prepared in accordance with the foregoing would be likely to kill cells expressing properdin and particularly those cells in which the anti-properdin antibodies of the invention are effective.

In connection with immunotoxins, antibodies can be modified to act as immunotoxins utilizing techniques that are well known in the art. See e.g., Vitetta *Immunol Today* 14:252 (1993). See also U.S. Pat. No. 5,194,594. In connection with the preparation of radiolabeled antibodies, such modified antibodies can also be readily prepared utilizing techniques that are well known in the art. See e.g., Junghans et al. in *Cancer Chemotherapy and Biotherapy* 655-686 (2d edition, Chafner and Longo, eds., Lippincott Raven (1996)). See also U.S. Pat. Nos. 4,681,581, 4,735,210, 5,101,827, 5,102,990 (RE 35,500), U.S. Pat. Nos. 5,648,471, and 5,697,902. Each of immunotoxins and radiolabeled molecules would be likely to kill cells expressing properdin, and particularly those cells in which the antibodies of the invention are effective.

In connection with the generation of therapeutic peptides, through the utilization of structural information related to properdin and antibodies thereto, such as the antibodies of the invention (as discussed below in connection with small molecules) or screening of peptide libraries, therapeutic peptides can be generated that are directed against properdin. Design and screening of peptide therapeutics is discussed in connection with Houghten et al. *Biotechniques* 13:412-421 (1992), Houghten *PNAS USA* 82:5131-5135 (1985), Pinalla et al. *Biotechniques* 13:901-905 (1992), Blake and Litzi-Davis *BioConjugate Chem.* 3:510-513 (1992). Immunotoxins and radiolabeled molecules can also be prepared, and in a similar manner, in connection with peptidic moieties as discussed above in connection with antibodies.

Assuming that the properdin molecule (or a form, such as a splice variant or alternate form) is functionally active in a disease process, it will also be possible to design gene and antisense therapeutics thereto through conventional techniques. Such modalities can be utilized for modulating the function of properdin. In connection therewith the antibodies of the present invention facilitate design and use of functional assays related thereto. A design and strategy for antisense therapeutics is discussed in detail in International Patent Application No. WO 94/29444. Design and strategies for gene therapy are well known. However, in particular, the use of gene therapeutic techniques involving intrabodies could prove to be particularly advantageous. See e.g., Chen et al. *Human Gene Therapy* 5:595-601 (1994) and Marasco *Gene Therapy* 4:11-15 (1997). General design of and considerations related to gene therapeutics is also discussed in International Patent Application No. WO 97/38137.

Small molecule therapeutics can also be envisioned in accordance with the present invention. Drugs can be designed to modulate the activity of properdin based upon the present invention. Knowledge gleaned from the structure of the properdin molecule and its interactions with other molecules in accordance with the present invention, such as the antibodies of the invention, properdin, and others can be utilized to rationally design additional therapeutic modalities. In this regard, rational drug design techniques such as X-ray crystallography, computer-aided (or assisted) molecular modeling (CAMM), quantitative or qualitative structure-activity relationship (QSAR), and similar technologies can be utilized to focus drug discovery efforts. Rational design allows prediction of protein or synthetic structures which can interact with the molecule or specific forms thereof which can be used to modify or modulate the activity of properdin. Such structures can be synthesized chemically or expressed in biological systems. This approach has been reviewed in Capsey et al. *Genetically Engineered Human Therapeutic Drugs* (Stockton Press, NY (1988)). Further, combinatorial libraries can be designed and sythesized and used in screening programs, such as high throughput screening efforts.

Therapeutic Administration and Formulations

It will be appreciated that the therapeutic entities in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15$^{th}$ ed, Mack Publishing Company, Easton, Pa. (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." *Regul. Toxicol. Pharmacol.* 32(2):210-8 (2000), Wang W. "Lyophilization and development of solid protein pharmaceuticals."*Int. J. Pharm.* 203(1-2):1-60 (2000), Charman W N "Lipids, lipophilic drugs, and oral drug delivery-some emerging concepts." *J. Pharm Sci.* 89(8):967-78 (2000), Powell et al. "Compendium of excipients for parenteral formulations" *PDA J Pharm Sci Technol.* 52:238-311 (1998) and the citations therein for additional information related to formulations, excipients and carriers well known to pharmaceutical chemists.

Preparation of Antibodies

Antibodies in accordance with the invention are preferably prepared through the utilization of a transgenic mouse that has a substantial portion of the human antibody producing genome inserted but that is rendered deficient in the production of endogenous, murine, antibodies. Such mice, then, are capable of producing human immunoglobulin molecules and antibodies and are deficient in the production of murine immunoglobulin molecules and antibodies. Technologies utilized for achieving the same are disclosed in the patents, applications, and references disclosed in the Background, herein. In particular, however, a preferred embodiment of transgenic production of mice and antibodies therefrom is disclosed in U.S. patent application Ser. No. 08/759,620, filed Dec. 3, 1996 and International Patent Application Nos. WO 98/24893, published Jun. 11, 1998 and WO 00/76310, published Dec. 21, 2000, the disclosures of which are hereby incorporated by reference. See also Mendez et al. *Nature Genetics* 15:146-156 (1997), the disclosure of which is hereby incorporated by reference.

Through use of such technology, we have produced fully human monoclonal antibodies to a variety of antigens. Essentially, we immunize XenoMouse® lines of mice with an antigen of interest, recover lymphatic cells (such as B-cells) from the mice that express antibodies, fuse such recovered cells with a myeloid-type cell line to prepare immortal hybridoma cell lines, and such hybridoma cell lines are screened and selected to identify hybridoma cell lines that produce antibodies specific to the antigen of interest. We utilized these techniques in accordance with the present invention for the preparation of antibodies specific to properdin. Herein, we describe the production of multiple hybridoma cell lines that produce antibodies specific to properdin. Further, we provide a characterization of the antibodies produced by such cell lines, including nucleotide and amino acid sequence analyses of the heavy and light chains of such antibodies.

The hybridoma cell lines discussed herein are readily generated by those of ordinary skill in the art, given the guidance provided herein. Each of the antibodies produced by the subject cell lines are either fully human IgG2 or IgG4 heavy chains with human kappa light chains. In general, antibodies in accordance with the invention possess very high affinities, typically possessing Kd's of from about $10^{-9}$ through about $10^{-11}$ M, when measured by either solid phase and solution phase.

As will be appreciated, antibodies in accordance with the present invention can be expressed in cell lines other than hybridoma cell lines. Sequences encoding particular antibodies can be used for transformation of a suitable mammalian host cell. Transformation can be by any known method for introducing polynucleotides into a host cell, including, for example packaging the polynucleotide in a virus (or into a viral vector) and transducing a host cell with the virus (or vector) or by transfection procedures known in the art, as exemplified by U.S. Pat. Nos. 4,399,216, 4,912,040, 4,740, 461, and 4,959,455 (which patents are hereby incorporated herein by reference). The transformation procedure used depends upon the host to be transformed. Methods for introduction of heterologous polynucleotides into mammalian cells are well known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are well known in the art and include many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), and a number of other cell lines. Cell lines of particular preference are selected through determining which cell lines have high expression levels and produce antibodies with constitutive properdin binding properties.

The results demonstrated in accordance with the present invention indicate that antibodies in accordance with the present invention possess certain qualities that may make the present antibodies more efficacious than currently available antibodies against properdin Antibodies in accordance with the invention have high affinities and appear efficacious in inhibiting the alternative complement pathway, and therefore in treating disorders associated with and/or mediated by the alternative complement pathway.

Polynucleotides, Vectors, and Host Cells

The present invention further provides polynucleotides, including isolated polynucleotides, that comprise a nucleotide sequence encoding a subject antibody. The present invention further provides vectors, including expression vectors, comprising a subject polynucleotide. The present invention further provides host cells, including isolated host cells, that comprise a subject polynucleotide or a subject vector. In many embodiments, a subject host cell produces a subject antibody.

The present invention provides polynucleotides ("nucleic acids"), including isolated polynucleotides, that comprise a nucleotide sequence encoding a subject antibody, as well as compositions comprising such nucleic acids. By nucleic acid composition is meant a composition comprising a sequence of DNA having an open reading frame that encodes a subject antibody and is capable, under appropriate conditions, of being expressed as a subject antibody.

Nucleic acids encoding a subject antibody may be cDNA or genomic DNA or a fragment thereof. The term gene shall be intended to mean the open reading frame encoding specific antibodies of the subject invention, and introns, as well as adjacent 5' and 3' non-coding nucleotide sequences involved in the regulation of expression, up to about 20 kb beyond the coding region, but possibly further in either direction. The gene may be introduced into an appropriate vector for extra-chromosomal maintenance or for integration into a host genome.

The term "cDNA" as used herein is intended to include all nucleic acids that share the arrangement of sequence elements found in native mature mRNA species, where sequence elements are exons and 3' and 5' non-coding regions. Normally mRNA species have contiguous exons, with the intervening introns, when present, being removed by nuclear RNA splicing, to create a continuous open reading frame encoding a protein according to the subject invention.

In some embodiments, a subject nucleic acid encoding a subject antibody light chain comprises a nucleotide sequence that has at least about 80%, at least about 85%, at least about 90%, at least about 95%, at least about 98%, or at least about 99% nucleotide sequence identity to any of SEQ ID NOs:01, 05, 09, 13, and 17, as shown in FIGS. 16A-F. In some embodiments, a subject nucleic acid encoding a subject antibody light chain differs by only one, two, three, four, five, six, seven, eight, nine, ten, 11, 12, 13, 14, 15, 16, 17, 18, 19, 20, 21, 22, 23, 24, or 25 nucleotides from any of SEQ ID NOs:01, 05, 09, 13, and 17. In some embodiments, a subject nucleic acid encoding a subject antibody light chain comprises a nucleotide sequence as set forth in any of SEQ ID NOs:01, 05, 09, 13, and 17.

In some embodiments, a subject nucleic acid encoding a subject antibody heavy chain comprises a nucleotide sequence that has at least about 80%, at least about 85%, at least about 90%, at least about 95%, at least about 98%, or at least about 99% nucleotide sequence identity to any of SEQ ID NOs:03, 07, 11, 15, and 19, as shown in FIGS. 16A-F. In some embodiments, a subject nucleic acid encoding a subject antibody heavy chain differs by only one, two, three, four, five, six, seven, eight, nine, ten, 11, 12, 13, 14, 15, 16, 17, 18, 19, 20, 21, 22, 23, 24, or 25 nucleotides from any of SEQ ID NOs:03, 07, 11, 15, and 19. In some embodiments, a subject nucleic acid encoding a subject antibody heavy chain comprises a nucleotide sequence as set forth in any of SEQ ID NOs:03, 07, 11, 15, and 19.

Exemplary, non-limiting antibodies are as follows: (1) an antibody designated GL001H8_7 comprising an antibody light chain variable region having an amino acid sequence as set forth in SEQ ID NO:02 and encoded by a nucleic acid having a nucleotide sequence as set forth in SEQ ID NO:01, an antibody heavy chain variable region having an amino acid sequence as set forth in SEQ ID NO:04 and encoded by a nucleic acid having a nucleotide sequence as set forth in SEQ ID NO:03; (2) an antibody designated GL001H8_14 comprising an antibody light chain variable region having an amino acid sequence as set forth in SEQ ID NO:06 and encoded by a nucleic acid having a nucleotide sequence as set forth in SEQ ID NO:05, an antibody heavy chain variable region having an amino acid sequence as set forth in SEQ ID NO:08 and encoded by a nucleic acid having a nucleotide sequence as set forth in SEQ ID NO:07; (3) an antibody designated GL001H8_11 comprising an antibody light chain variable region having an amino acid sequence as set forth in SEQ ID NO:10 and encoded by a nucleic acid having a nucleotide sequence as set forth in SEQ ID NO:09, an antibody heavy chain variable region having an amino acid sequence as set forth in SEQ ID NO:12 and encoded by a nucleic acid having a nucleotide sequence as set forth in SEQ ID NO:11; (4) an antibody designated GL001H1_6_2 comprising an antibody light chain variable region having an amino acid sequence as set forth in SEQ ID NO:14 and encoded by a nucleic acid having a nucleotide sequence as set forth in SEQ ID NO:13, an antibody heavy chain variable region having an amino acid sequence as set forth in SEQ ID NO:16 and encoded by a nucleic acid having a nucleotide sequence as set forth in SEQ ID NO:15; and (5) an antibody designated GL001H1_12_1 comprising an antibody light chain variable region having an amino acid sequence as set forth in SEQ ID NO:18 and encoded by a nucleic acid having a nucleotide sequence as set forth in SEQ ID NO:17, an antibody heavy chain variable region having an amino acid sequence as set forth in SEQ ID NO:20 and encoded by a nucleic acid having a nucleotide sequence as set forth in SEQ ID NO:19.

A genomic sequence of interest comprises the nucleic acid present between the initiation codon and the stop codon, as defined in the listed sequences, including all of the introns that are normally present in a native chromosome. It may further include the 3' and 5' untranslated regions found in the mature mRNA. It may further include specific transcriptional and translational regulatory sequences, such as promoters, enhancers, etc., including about 1 kb, but possibly more, of flanking genomic DNA at either the 5' or 3' end of the transcribed region. The genomic DNA may be isolated as a fragment of 100 kbp or smaller; and substantially free of flanking chromosomal sequence. The genomic DNA flanking the coding region, either 3' or 5', or internal regulatory sequences as sometimes found in introns, contains sequences required for proper tissue and stage specific expression.

The subject nucleic acid molecules may also be provided as part of a vector (e.g., a "construct"), a wide variety of which are known in the art and need not be elaborated upon herein. Vectors include, but are not limited to, plasmids; cosmids; viral vectors; artificial chromosomes (YAC's, BAC's, etc.); mini-chromosomes; and the like. Vectors are amply described in numerous publications well known to those in the art, including, e.g., Short Protocols in Molecular Biology, (1999) F. Ausubel, et al., eds., Wiley & Sons. Vectors may provide for expression of the subject nucleic acids, may provide for propagating the subject nucleic acids, or both.

The subject genes are isolated and obtained in substantial purity, generally as other than an intact chromosome. Usually, the DNA will be obtained substantially free of other nucleic acid sequences that do not include a sequence or fragment thereof of the subject genes, generally being at least about 50%, usually at least about 90% pure and are typically "recombinant", i.e. flanked by one or more nucleotides with which it is not normally associated on a naturally occurring chromosome.

The subject nucleic acid compositions find use in the preparation of all or a portion of a subject antibody. For expression, an expression cassette may be employed. The expression vector will provide a transcriptional and translational initiation region, which may be inducible or constitutive, where the coding region is operably linked under the transcriptional control of the transcriptional initiation region, and a transcriptional and translational termination region. These control regions may be native to a gene encoding the subject peptides, or may be derived from exogenous sources.

Expression vectors generally have convenient restriction sites located near the promoter sequence to provide for the insertion of nucleic acid sequences encoding heterologous proteins. A selectable marker operative in the expression host may be present. Expression vectors may be used for the production of fusion proteins, where the exogenous fusion peptide provides additional functionality, i.e. increased protein synthesis, stability, reactivity with defined antisera, an enzyme marker, e.g. β-galactosidase, etc.

A subject antibody may be expressed in prokaryotes or eukaryotes in accordance with conventional ways, depending upon the purpose for expression. For large scale production of the protein, a unicellular organism, such as E. coli, B. subtilis, S. cerevisiae, insect cells in combination with baculovirus vectors, or cells of a higher organism such as vertebrates, particularly mammals, e.g. COS 7 cells, may be used as the expression host cells. In some situations, it is desirable to express the nucleic acid in eukaryotic cells, where the encoded protein will benefit from native folding and post-translational modifications.

The present invention provides host cells, including isolated host cells, that comprise a subject polynucleotide or a subject vector. In many embodiments, a subject host cell is a eukaryotic host cell that is capable of producing antibody after being genetically modified with a subject expression vector. In many embodiments, a subject host cell is a hybridoma cell that is produced by fusing an antibody-producing cell from a XenoMouseg that has been immunized with properdin with a cell that serves as a fusion partner, e.g., a myeloma fusion partner that does not produce antibody.

Treatment Methods

The present invention provides therapeutic methods involving use of a subject anti-properdin antibody in therapeutic methods carried out on a mammalian host, including methods of inhibiting the alternative complement pathway, including methods of reducing the level of a polypeptide generated following activation of the alternative complement pathway; methods of reducing the level of membrane attack complex (MAC); methods of reducing the level of an anaphylatoxin; methods of reducing the level of C3c; and methods of treating a disease or disorder mediated by the alternative complement pathway. The methods generally involve administering to a mammalian subject in need thereof an effective amount of a subject antibody.

An "effective amount" of a subject antibody is an amount that is effective to reduce the production and/or level of a polypeptide generated following activation of the alternative complement pathway by at least about 20%, at least about 30%, at least about 40%, at least about 50%, at least about 60%, at least about 70%, at least about 80%, at least about 90%, or more.

A subject antibody is administered to an individual in a formulation with a pharmaceutically acceptable excipient(s). A wide variety of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., $7^{th}$ ed., Lippincott, Williams, & Wilkins; and Handbook of Pharmaceutical Excipients (2000) A. H. Kibbe et al., eds., 3 ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In the subject methods, a subject antibody may be administered to the host using any convenient means capable of resulting in the desired therapeutic effect. Thus, the antibody can be incorporated into a variety of formulations for therapeutic administration. More particularly, a subject antibody can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

As such, administration of a subject antibody can be achieved in various ways, including oral, buccal, rectal, parenteral, intraperitoneal, intradermal, subcutaneous, intramuscular, transdermal, intranasal, pulmonary, intratracheal, etc., administration.

Subcutaneous administration of a subject antibody is accomplished using standard methods and devices, e.g., needle and syringe, a subcutaneous injection port delivery system, and the like. Intramuscular administration is accomplished by standard means, e.g., needle and syringe, continuous delivery system, etc.

In some embodiments, a subject antibody is delivered by a continuous delivery system. The term "continuous delivery system" is used interchangeably herein with "controlled delivery system" and encompasses continuous (e.g., controlled) delivery devices (e.g., pumps) in combination with catheters, injection devices, and the like, a wide variety of which are known in the art. Mechanical or electromechanical infusion pumps can also be suitable for use with the present invention. Examples of such devices include those described in, for example, U.S. Pat. Nos. 4,692,147; 4,360,019; 4,487,603; 4,360,019; 4,725,852; 5,820,589; 5,643,207; 6,198,966; and the like. In general, the present methods of drug delivery can be accomplished using any of a variety of refillable, pump systems. Pumps provide consistent, controlled release over time.

In pharmaceutical dosage forms, the agents may be administered in the form of their pharmaceutically acceptable salts, or they may also be used alone or in appropriate association, as well as in combination, with other pharmaceutically active compounds. The following methods and excipients are merely exemplary and are in no way limiting.

A subject antibody can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of a subject antibody calculated in an amount sufficient to produce the desired effect in association with a pharmaceutically acceptable diluent, carrier or vehicle. The specifications for the unit dosage forms of the present invention depend on the particular compound employed and the effect to be achieved, and the pharmacodynamics associated with each compound in the host.

A subject antibody is administered to an individual at a frequency and for a period of time so as to achieve the desired therapeutic effect. For example, a subject antibody is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid), or substantially continuously, or continuously, over a period of time ranging from about one day to about one week, from about two weeks to about four weeks, from about one month to about two months, from about two months to about four months, from about four months to about six months, or longer.

Combination Therapy

A subject antibody will in some embodiments be administered in an effective amount in combination therapy with a second therapeutic agent. Suitable second therapeutic agents include, but are not limited to, anti-inflammatory agents; agents used for the treatment of cardiovascular disorders; steroidal anti-inflammatory agents; and the like.

Suitable anti-inflammatory agents include, but are not limited to, non-steroidal anti-inflammatory drugs (NSAIDs) acetaminophen, salicylate, acetyl-salicylic acid (aspirin, diflunisal), ibuprofen, Motrin, Naprosyn, Nalfon, and Trilisate, indomethacin, glucametacine, acemetacin, sulindac, naproxen, piroxicam, diclofenac, benoxaprofen, ketoprofen, oxaprozin, etodolac, ketorolac tromethamine, ketorolac, nabumetone, and the like, and mixtures of two or more of the foregoing. Other suitable anti-inflammatory agents include methotrexate.

Suitable steroidal anti-inflammatory agents include, but are not limited to, hydrocortisone, prednisone, prednisolone, methylprednisolone, dexamethasone, betamethasone, and triamcinolone.

Suitable agents for cardiovascular indications include GP IIb-IIIa inhibitors such as Integrilin® (eptifibatide); aprotinin; ReoPro® (abciximab); and the like.

Suitable second therapeutic agents include beta adrenergics which include bronchodilators including albuterol, isoproterenol sulfate, metaproterenol sulfate, terbutaline sulfate, pirbuterol acetate and salmeterol formotorol; steroids including beclomethasone dipropionate, flunisolide, fluticasone, budesonide and triamcinolone acetonide. Anti-inflammatory drugs used in connection with the treatment of respiratory diseases include steroids such as beclomethasone dipropionate, triamcinolone acetonide, flunisolide and fluticasone. Other suitable anti-inflammatory drugs include cromoglycates such as cromolyn sodium. Other respiratory drugs which would qualify as bronchodilators include anticholenergics including ipratropium bromide. Antihistamines include, but are not limited to, diphenhydramine, carbinoxamine, clemastine, dimenhydrinate, pryilamine, tripelennamine, chlorpheniramine, brompheniramine, hydroxyzine, cyclizine, meclizine, chlorcyclizine, promethazine, doxylamine, loratadine, and terfenadine. Particular anti-histamines include rhinolast (Astelin), claratyne (Claritin), claratyne D (Claritin D), telfast (Allegra), zyrtec, and beconase.

In some embodiments, a subject antibody is administered concurrently with a second therapeutic agent. As used herein, the term "concurrently" indicates that the subject antibody and the second therapeutic agent are administered separately and are administered within about 5 seconds to about 15 seconds, within about 15 seconds to about 30 seconds, within about 30 seconds to about 60 seconds, within about 1 minute to about 5 minutes, within about 5 minutes to about 15 minutes, within about 15 minutes to about 30 minutes, within about 30 minutes to about 60 minutes, within about 1 hour to about 2 hours, within about 2 hours to about 6 hours, within about 6 hours to about 12 hours, within about 12 hours to about 24 hours, or within about 24 hours to about 48 hours of one another.

In some embodiments, a subject antibody is administered during the entire course of treatment with the second therapeutic agent. In other embodiments, a subject antibody is administered for a period of time that is overlapping with that of the treatment with the second therapeutic agent, e.g., the antibody treatment can begin before the treatment with the second therapeutic agent begins and end before the treatment with the second therapeutic agent ends; the antibody treatment can begin after the treatment with the second therapeutic agent begins and end after the antibody treatment ends; the antibody treatment can begin after the treatment with the second therapeutic agent begins and end before the treatment with the second therapeutic agent ends; or antibody treatment can begin before the treatment with the second therapeutic agent begins and end after the treatment with the second therapeutic agent ends.

Subjects Suitable for Treatment

Subjects suitable for treatment with a subject method include individuals suffering from one or more of the following disorders: post-cardiopulmonary bypass inflammation, myocardial infarction, stroke, acute respiratory distress syndrome (ARDS), septic shock, transplant rejection, burn injury, multiple sclerosis, myasthenia gravis, cardiovascular disorders, and rheumatoid arthritis. Subjects suitable for treatment with a subject method also include individuals suffering from any inflammatory disorder, including, but not limited to, systemic lupus erythematosus, membranous nephritis, pemphigoid, dermatomyositis, and anti-phospholipid syndrome. Subjects suitable for treatment also include subjects undergoing renal dialysis.

Incorporation by Reference

All references cited herein, including patents, patent applications, papers, text books, and the like, and the references cited therein, to the extent that they are not already, are hereby incorporated herein by reference in their entirety. In addition, the following references are also incorporated by reference herein in their entirety, including the references cited in such references:

Equivalents

The foregoing description and Examples detail certain preferred embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s, second(s); min, minute(s); hr, hour(s); and the like.

Example 1

Preparation and Characterization of Anti-Properdin Monoclonal Antibodies

Summary

The aim of this study was to identify fully human monoclonal antibodies (MoAbs) that bind to human properdin with high affinity and block the complement alternative pathway. Since it is important that these MoAbs do not themselves trigger inflammation via activation of complement or Fcγ receptors, IgG2 and IgG4 XenoMouse strains were targeted for immunization. Human properdin was used as the immunogen and several IgG2 and IgG4 XenoMouse animals received either footpad or tail-vein immunizations. Fusions with splenocytes from both IgG2 and IgG4 animals were performed, and IgG2 hybridoma supernatant samples were determined to bind to human properdin. These samples were evaluated for their ability to neutralize properdin function. The results reveal that several of the fully human anti-properdin MoAbs block properdin function.

Materials and Methods

Generation of Hybridomas

Xenomouse animals were immunized via footpad route for all injections. Total volume of each injection was 50 µl per mouse, or 25 µl per footpad Initial injections were with 10 µg human properdin in pyrogen free DPBS, admixed 1:1 v/v with TiterMax Gold per mouse. Subsequent boosts were made with 10 ug Human Properdin in pyrogen free DPBS admixed with 25 µg of Adju-Phos (aluminum phosphate gel) per mouse for six times, then a final boost of 10 µg human properdin in pyrogen free DPBS without adjuvant per mouse. The animals were immunized on days 0, 3, 6, 10, 13, 17, 20, and 24 for this protocol; and fusions were performed on day 29. Following the immunization regimen described above, mice were euthanized, then inguinal and lumbar lymph nodes were recovered.

Lymphocytes were released by mechanical disruption of the lymph nodes using a tissue grinder, followed by depletion of T cells by CD90 negative selection. The fusion was performed by mixing washed enriched B cells and nonsecretory myeloma P3X63Ag8.653 cells purchased from ATCC, cat. # CRL 1580 (Kearney et al, J. Immunol. 123, 1979, 1548-1550) at a ratio of 1:1. The cell mixture was gently pelleted by centrifugation at 800 g. After complete removal of the supernatant, the cells were treated with 2-4 mL of Pronase solution (CalBiochem, cat. # 53702; 0.5 mg/ml in phosphate buffered saline (PBS)) for no more than 2 minutes. Then 3-5 ml of fetal bovine serum (FBS) was added to stop the enzyme activity and the suspension was adjusted to 40 ml total volume using electro-cell fusion solution, ECFS (0.3M Sucrose, Sigma, Cat# S7903, 0.1 mM Magnesium Acetate, Sigma, Cat# M2545, 0.1 mM Calcium Acetate, Sigma, Cat# C4705). The supernatant was removed after centrifugation and the cells were resuspended in 40 ml ECFS. This wash step was repeated and the cells again were resuspended in ECFS to a concentration of $2 \times 10^6$ cells/ml. Electro-cell fusion was performed using a fusion generator (model ECM2001, Genetronic, Inc., San Diego, Calif.). The fusion chamber size used was 2.0 ml using the following instrument settings.

Alignment condition: voltage: 50 v, time: 50 s
Membrane breaking at: voltage: 3000 v, time: 30 µs
Post-fusion holding time: 3 s After fusion, the cells were resuspended in hybridoma fusion medium: DMEM (JRH Biosciences), 15% FBS (Hyclone), containing 0.5× Azaserine hypoxanthine (HA) (Sigma, cat. # A9666), and supplemented with L-glutamine, pen/strep, OPI (oxaloacetate, pyruvate, bovine insulin) (all from Sigma) and IL-6 (Boehringer Mannheim) for culture at 37° C., and 10% $CO_2$ in air. Cells were plated in flat bottomed 96-well tissue culture plates at $4 \times 10^4$ cells per well. Cultures were maintained in hybridoma fusion medium for 2 weeks before transfer to Hybridoma medium: DMEM (JRH Biosciences), 15% FBS (Hyclone), and supplemented with L-glutamine, pen/strep (penicillin/streptomycin), OPI (oxaloacetate, pyruvate, bovine insulin) (all from Sigma) and IL-6 (Boehringer Mannheim). Hybridomas were selected for by survival in 0.5×HA hybridoma fusion medium and supernatants from those wells containing hybridomas were screened for antigen reactivity by enzyme-linked immunosorbent assay (ELISA).

Cloning was performed on selected antigen-positive wells using limited dilution plating. Plates were visually inspected for the presence of single colony growth and supernatants from single colony wells were then screened by antigen-specific ELISAs as described above. Highly reactive clones were assayed to verify purity of human gamma and kappa chain by multiplex ELISA using a Luminex instrument.

Enzyme-Linked Immunosorbent Assay (ELISA)

The ELISA format entailed incubating supernatants on antigen coated plates (human properdin coated plates) and detecting human anti-human properdin binding antibodies using horseradish peroxidase (HRP) labeled mouse anti-human IgG. All positive samples were confirmed by two sets of ELISA in parallel, which entailed incubating supernatants on antigen coated plates (human properdin coated plates) and detecting human anti-human properdin binding antibodies using horseradish peroxidase (HRP) labeled mouse anti-human Gamma and Kappa chain.

LPS Complement Activation—C5b-9 Assay

Complement within human serum is activated by lipopolysaccharide (LPS) that has been immobilized onto microtiter wells. This results in the covalent attachment of C5b-9 to the LPS. Briefly, microtiter wells (medium binding plates, Corning Costar) were coated with 1 µg/50 µl/well of LPS from *Salmonella typhosa* (Sigma Chemical) in 50 mM sodium bicarbonate buffer pH 9.5 overnight at 4° C. After aspirating the LPS solution, wells were blocked with 1% BSA in PBS for 2 hours at room temperature. At the end of this incubation, wells were washed with PBS and incubated with 8% normal human serum in either a) 0.4% HSA (human serum albumin) in Mg++-EGTA-VBS buffer (5 mM diethyl barbiturate, 120 mM NaCl, 5 mM $MgCl_2$, 5 mM EGTA, pH 7.2) or b) 0.4% HSA in EDTA-VBS buffer (5 mM diethyl barbiturate, 120 mM NaCl, 20 mM EDTA). Samples in EDTA-VBS served as background controls.

The microtiter plates were incubated at 37° C. for 1 hour in a water bath to allow LPS-mediated complement activation to occur. The plates were washed with PBS and the deposited C5b-9 was detected by adding a mouse anti-human C5b-9 monoclonal antibody (Quidel Corp, San Diego, Calif.) at 1:1000 dilution in 1% blocking solution.

Following a 1 hour incubation at room temperature, the plates were washed again with PBS and a peroxidase-conjugated goat anti-mouse antibody (Sigma, 1:2000 dilution in blocking solution) was added. Following a 1 hour incubation at room temperature the plates were rinsed extensively with PBS, and 100 µl of 3,3',5,5' tetramethyl benzidine (TMB) substrate (Kirkegaard & Perry Laboratories) was added. The reaction of TMB was quenched by the addition of 100 µl of 1 M phosphoric acid, and plates were read at 450 nm in an ELISA plate reader.

The effect of IgG2 samples on C5b-9 formation was evaluated by adding 3 βg/ml of IgG to a fixed concentration of human serum. The extent of inhibition of C5b-9 formation was determined using the antibody detection system described above.

C3b-Properdin Binding Assay

Polystyrene microtiter plates (96-well medium binding plates, Corning Costar) were coated with human C3b (0.5 µg/50 µl/well; Calbiochem, San Diego, Calif.) in PBS overnight at 4° C. After aspirating the C3b solution, wells were blocked with PBS containing 1% BSA for 2 hours at room temperature. Wells without C3b coating served as background controls. The ability of IgG2 samples to inhibit C3b-properdin binding was evaluated by adding various IgG2 samples (final concentration 3 µg/ml) to a constant concentration of properdin (1 nM). Following a 2 hour incubation at room temperature, the wells were extensively rinsed with PBS. C3b-bound properdin was detected by the addition of mouse anti-human properdin monoclonal antibody P#2 (Quidel, San Diego, Calif.) at 1:1000 dilution in blocking solution, which was allowed to incubate for 1 hour at room temperature. After washing plates with PBS, peroxidase-conjugated goat anti-mouse antibody (1:1000 dilution in blocking solution) was added and allowed to incubate for 1 hour. The plates were again rinsed thoroughly with PBS, and 100 µl of TMB substrate was added. The reaction of TMB was quenched by the addition of 100 µl of 1 M phosphoric acid and the plates were read at 450 nm in a microplate reader.

LPS Complement Activation—C3c Assay

Complement within human serum is activated by lipopolysaccharide (LPS) that has been immobilized onto microtiter wells. This results in the covalent attachment of C3c to the LPS. Briefly, polystyrene microtiter plates (medium binding plates, Corning Costar) were coated with LPS from *Salmonella typhosa* (1 µg/50 µl/well, Sigma Chemical Co) in 50 mM bicarbonate buffer, pH 9.5 overnight at 4° C. After aspirating the LPS solution, wells were blocked with PBS containing 1% BSA for 1 hr at room temperature and then washed with PBS and placed on ice. Samples containing IgG (1 µg/ml) and 8% normal human serum in either $Mg^{++}$-EGTA-GVB buffer (13 mM $MgCl_2$, 13 mM EGTA in gelatin veronal buffer, pH 7.3) or EDTA-GVB buffer (20 mM EDTA in gelatin veronal buffer, pH 7.3) were prepared at 4° C. and samples (50 µl/well) transferred to the microtiter plates.

Complement was activated by heating the microtiter plates at 37° C. for 30 min. The plates were then cooled to 0° C. in a water bath to stop further complement activation and washed extensively with cold PBS-Tween (0.05% Tween 20™ non-ionic detergent in PBS). Rabbit anti-human C3c (DAKO #A0062, 1:10,000 dilution) in PBS-bovine serum albumin (BSA) (PBS containing 2 mg/ml BSA) was added and allowed to incubate for 1 hr at room temperature. After washing the plate with PBS, peroxidase-conjugated goat anti-rabbit antibody (American Qualex, 1:10,000 dilution) in PBS-BSA was added and allowed to incubate for 1 hour at room temperature. The plate was again rinsed thoroughly with PBS, and 100 µl of TMB substrate was added. The reaction of TMB was quenched by the addition of 100 µl of 1 M phosphoric acid, and the plate was read at 450 nm in a microplate reader.

Results

Eleven samples were analyzed for their ability to 1) inhibit lipopolysaccharide (LPS)-induced activation of the complement alternative pathway and 2) to block properdin binding to the complement protein, C3b. The samples are designated 1.1, 1.2, 1.6, 1.7, 1.11, 1.14, 1.16, 1.20, 1.21, 1.22, and 1.25 in FIGS. 1, 2, and 3. Monoclonal antibody #23 (MoAb #23) was included as a positive control.

Several of the IgG2 supernatant samples caused a reduction in the formation of the complement activation product, C5b-9, when tested at 3 µg/ml in the LPS-activated alternative pathway assay (FIG. 1). In particular, samples 1.1, 1.6, 1.11, 1.16, and 1.22 caused ≧50% inhibition of C5b-9 formation. The activities of samples 1.11 and 1.16 approached the level of inhibition observed with MoAb #23, a potent blocking murine anti-human properdin IgG1 that was included as a positive control in the assay.

Figure 2:
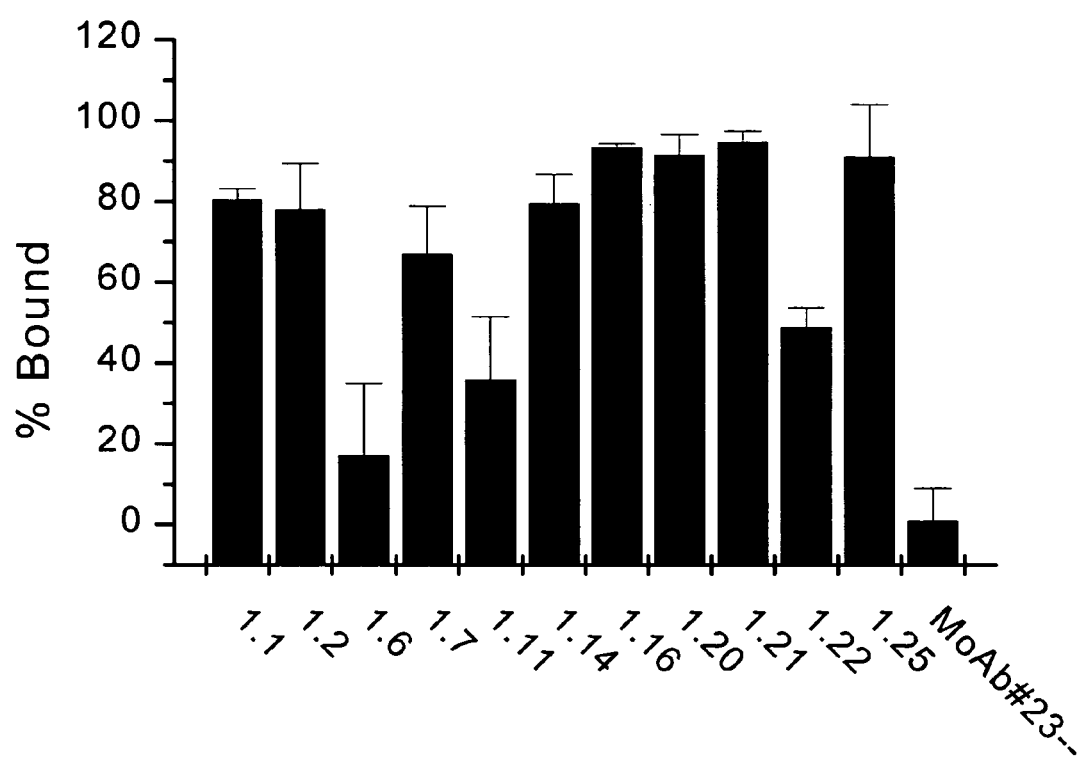
FIG. 2 depicts analysis of IgG2 antibodies in a C3b-properdin binding assay.

Analysis of the supernatant samples in the C3b-properdin binding assay revealed a general concordance with the results of the LPS-activation assay. In particular, samples 1.6, 1.11 and 1.22 caused 50% or more inhibition of properdin binding to C3b (FIG. 2). Interestingly, samples 1.1 and 1.16, which were active in the LPS-activation assay, showed little activity in the C3b-properdin binding assay. This suggests that these samples may block complement alternative pathway function without disrupting properdin binding to C3b. The samples containing low concentrations of IgG2 were also tested in this assay at the highest concentrations practicable. The results of this analysis, which are summarized in Table 1, indicate that sample 1.12 was an effective inhibitor of C3b-properdin binding, since 0.25 µg/ml caused a significant effect. Given the relativity low concentration that was tested, it also appears that sample 1.13 has appreciable blocking activity.

TABLE 1

Analysis of Dilute IgG2 Samples in a C3b-Properdin Binding Assay

| Sample # | µg/ml | % Bound | SD |
|---|---|---|---|
| 1.3 | 0.27 | 92.1 | 0.5 |
| 1.8 | 0.12 | 95.9 | 4.6 |
| 1.12 | 0.25 | 23.1 | 4.7 |
| 1.13 | 0.43 | 58.9 | 2.5 |
| 1.17 | 0.57 | 81.4 | 3.0 |
| 1.19 | 0.80 | 64.4 | 1.9 |
| 1.24 | 1.40 | 87.1 | 2.2 |

Figure 3:
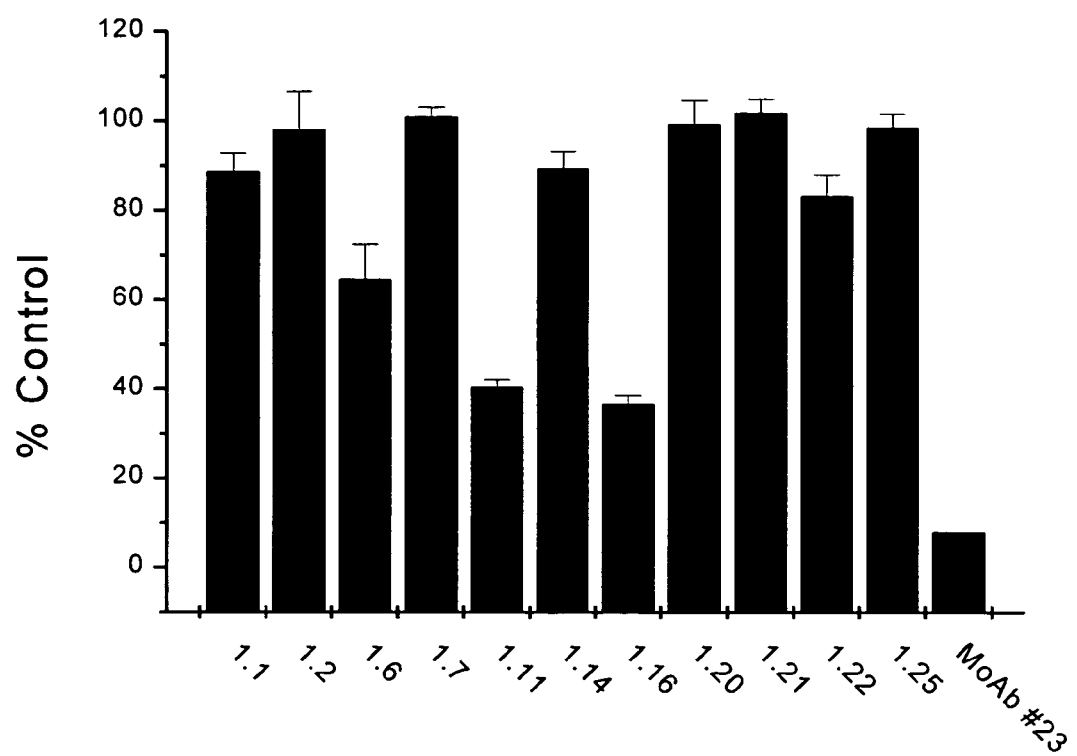
FIG. 3 depicts analysis of IgG2 antibodies in an LPS-activation C3c assay.

A second complement alternative pathway assay was utilized to confirm that sample 1.1 and 1.16 could inhibit complement activation, even though they did not block C3b-properdin binding. This assay also relies on LPS activation of complement, but measures the formation of the activation product, C3c, instead of C5b-9. It should be noted that this assay was run with 1 µg/ml of the samples instead of the 3 µg/ml used in the previous examples. In agreement with the results presented in FIG. 1, the most active samples in the C3c assay were 1.11 and 1.16 (FIG. 3). In addition, sample 1.6 appeared to partially inhibit alternative pathway activation. None of the samples were as active as the standard anti-properdin MoAb #23. However, since these samples are likely to be mixtures of clones, there may be multiple IgG2 species in each sample supernatant. The observation that sample 1.16 was active in two separate functional assays, but inactive in the C3b-properdin binding assay, appears to confirm that this MoAb is acting by a unique mechanism.

The aforementioned lines exhibiting activity in the above assays were cloned and further evaluated to confirm their potency in inhibiting complement activation. More specifically, lines 1.16, 1.11, 1.22, and 1.6 were cloned and re-evaluated. Clones of the 1.16, 1.22, and 1.11 lines were determined to be only partial inhibitors of C3c generation. Based on those results, no further studies were performed on clones derived from lines 1.16, 1.22, and 1.11. However, clones of the 1.6 line were determined to be potent inhibitors of C3c generation. The lead candidate clone from the 1.6 line is designated as 1.6.2.1.3 and was further analyzed to determine its efficacy in inhibiting complement activation.

Example 2

Anti-Properdin Nonoclonal Antibodies Inhibit C3c and sC5b-9 Generation in 8% Human Serum Materials and Methods Human C3c and sMAC ELISA Assay Sigma *S. typhosa* LPS L6386 (25 mg/sample) was used. LPS (3 mg) was dissolved in 1 ml of carbonate buffer, and diluted to 20 µg/ml in carbonate buffer (1:150 dilution). LPS stock solution was made fresh before use. Wells were coated overnight at 4° C. with 50 µl/well of 20 µg/ml LPS in 50 mM carbonate buffer pH 9.5 (1 µg LPS/well).

Carbonate buffer was made by dissolving 0.265 g of $Na_2CO_3$ in 50 ml sterile $H_2O$ for 50 mM stock solution. AP Buffer (13 mM EGTA, 13 mM $MgCl_2$ in Gelatin Veronal Buffer (Sigma-Aldrich, Catalog number: G6514) pH 7.3) was made. As a negative control, 13 mM EDTA in Gelatin Veronal Buffer was used. Human serum (QED BioScience, Inc.) was prepared by diluting human serum to 16% with AP buffer, or with EDTA-Gelatin Veronal Buffer. Antibody samples were diluted to a concentration of 180 µg/ml in 2 mg/ml BSA-PBS and labeled as STOCK A. Stocks B, C, and D were made by preparing serial 1:10 dilutions of Stock A in 2 mg/ml BSA-PBS.

ELISA assays were carried out as follows. Wells of a 96-well microtiter plate were coated with 1 µg of freshly-prepared LPS in a volume of 50 µl per well. Plates were incubated overnight at 4° C. Wells were washed 3 times with 200 µl PBS. 100 µl Blocking Buffer (30 ml PBS, 300 mg BSA, i.e. 1% BSA) were added; and plates were incubated for 1 hour at room temperature. Wells were washed 3 times using 200 µl PBS. The plates were subsequently kept on ice, and 50 µl sample added per well (in quadruplicate). The plates were incubated for 30 minutes at 37° C. in a water bath. The reaction was stopped by transferring the plate from water bath to ice bucket with ice-water mix. The supernatant sample was harvested into a 0.7 ml tube on ice for subsequent C3a and sC5b-9 ELISA assays. Sample were stored at −70° C.

Wells were washed 3 times using 200 µl of ice cold PBS-Tween 20 (0.05% Tween 20 in PBS-250 µl Tween 20 in 500 ml PBS). Washes were performed on ice. Wells were washed twice with 200 µl PBS at room temperature. 100 µl/well of a 1:10,000 dilution of DAKO A0062 rabbit anti-human C3c (primary Ab) in PBS-BSA (2 mg/ml) was added. Plates were incubated for 1 hour at room temperature. Wells were washed 5 times with 200 µl PBS. 100 µl of a 1:10,000 dilution of American Qualex (A102PU) peroxidase conjugated goat anti-rabbit IgG (secondary antibody) in PBS-2 mg/ml BSA was added. A solution containing 2.2 µl of antibody was prepared. Plates were incubated for 1 hour at room temperature. Following the incubation, plates were washed 5 times with 200 µl PBS. Substrate pre-warmed to room temperature was added (100 µl/well), and plates were incubated for approximately 5 minutes (at room temperature). The reaction was stopped with 100 µl 1N $H_3PO_4$ and $OD_{450}$ measured.

Results

Figure 4:
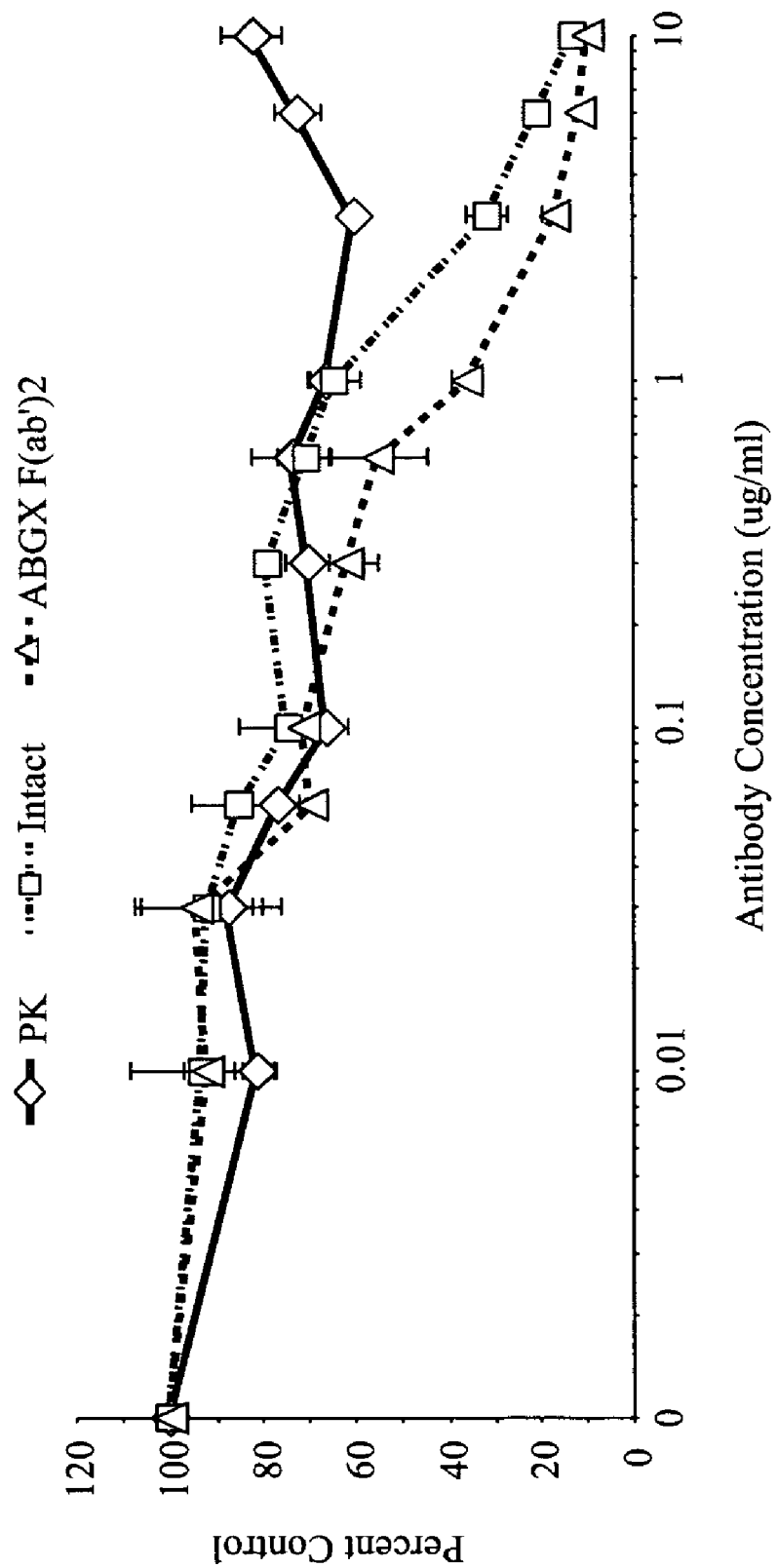
FIG. 4 depicts inhibition of membrane attack complex production by anti-properdin antibodies.
Figure 5:
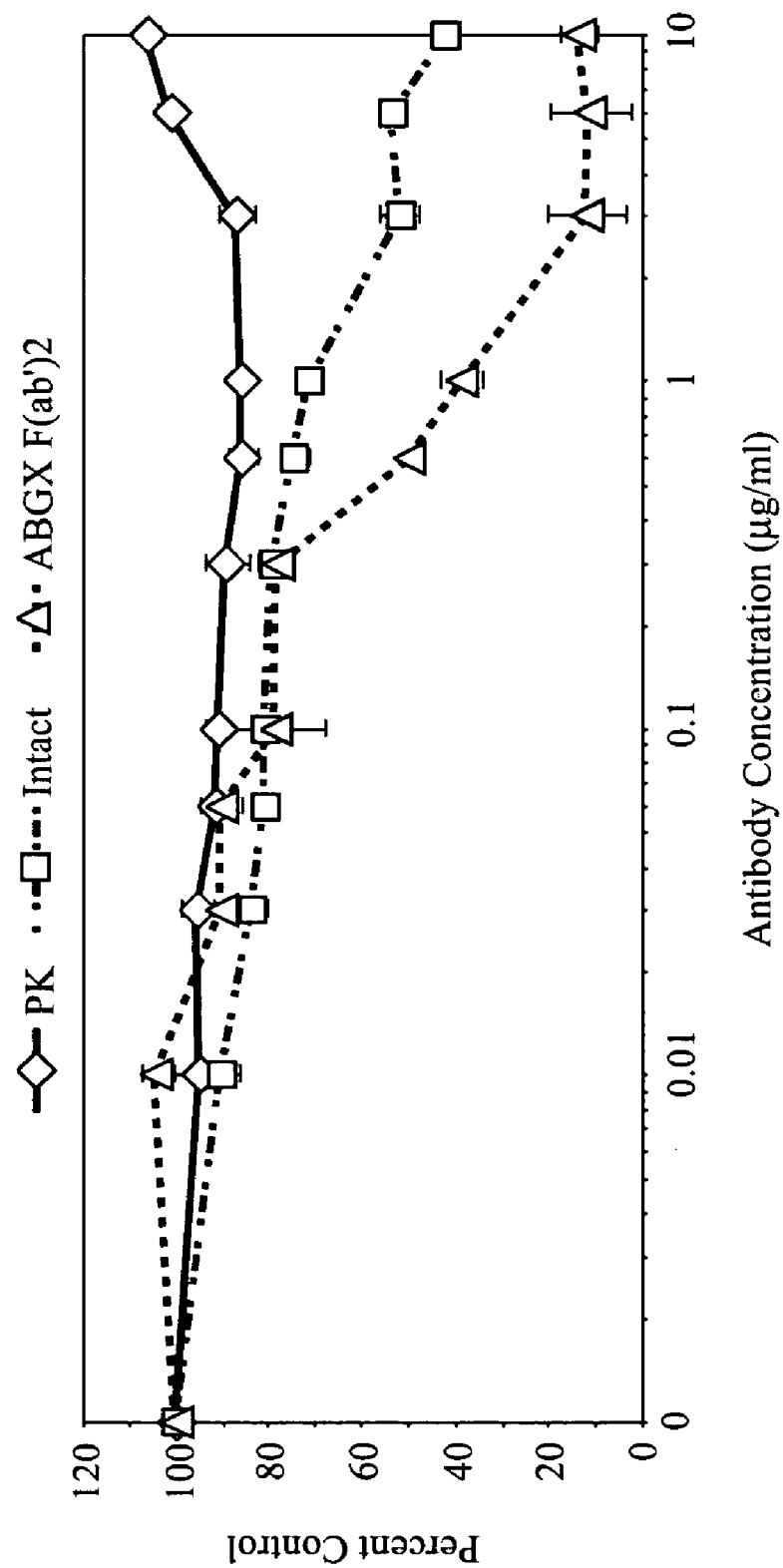
FIG. 5 depicts inhibition of C3a production by anti-properdin antibodies.

The results are shown in FIGS. 4 and 5. FIG. 4 demonstrates a dose-dependent inhibition of sMAC production in an in vitro LPS assay using anti-properdin antibodies. As shown above, using an isotype PK control antibody, no inhibition of sMAC production is observed. A fully intact anti-properdin (clone 1.6.2.1.3) or F(ab)'2 antibody exhibited near complete inhibition of sMAC production at a concentration of 10 µg/ml. FIG. 5 demonstrates a dose-dependent inhibition of C3a production in an in vitro LPS assay using anti-properdin antibodies. As shown above, using an isotype PK control antibody, no inhibition of sMAC production is observed. A fully intact anti-properdin (clone 1.6.2.1.3) or F(ab)'2 antibody exhibited significant inhibition of C3a production at a concentration of 10 µg/ml.

Example 3

The Effects of Anti-Properdin Monoclonal Antibodies on Inhibition of Complement Activation in a Tubing Loop Model of Cardiopulmonary Bypass Experimental Design In this experiment, tubing loops were filled with 1.5 ml of diluted blood from a healthy volunteer. The tubing loops were rotated vertically in a water bath at 37° C. for 2 hours to allow for complement activation to occur. Blood samples from the tubing loops were transferred into polypropylene tubes that were pre-loaded with EDTA for determining complement activation. The addition of EDTA prevents further complement activation that would otherwise occur during sample processing. Blood samples were centrifuged to separate plasma and aliquoted for analysis.

Materials/Reagents

Blood (25 ml) was collected in a 50-ml polypropylene tube containing 125 µl of porcine heparin. Blood was diluted 1:1 with plasmalyte-148 (Baxter Healthcare Corporation) for a final heparin concentration of 2.5 units per ml of diluted blood. To each tube was added 700 µl PBS (untreated), intact antibody, or F(ab)'$_2$ antibody (final concentration of 200 µg/ml or 133 µg/ml respectively). As a negative control, 1.5 ml of diluted blood was added to a polypropylene tube containing 48 µl of EDTA (20 mM final concentration). The negative control sample was not be added to the tubing loop and represented a background control.

The polyethylene tubing (16.5 inches) was filled with 1.5 ml of blood sample and closed into a loop with a piece of silicone tubing. The tubing was incubated in a water bath at 37° C., and rotated vertically. Following the 2 hour incubation at 37° C., the blood samples were aliquoted into polypropylene tubes (4.0 ml capacity) preloaded with 0.5M EDTA (final EDTA concentration of 20 mM). The blood samples were centrifuged at 4° C. (2,500 G for 20 minutes) to collect the plasma. C3a, sMAC, and C5a levels were evaluated by ELISA.

Results

Figure 6:
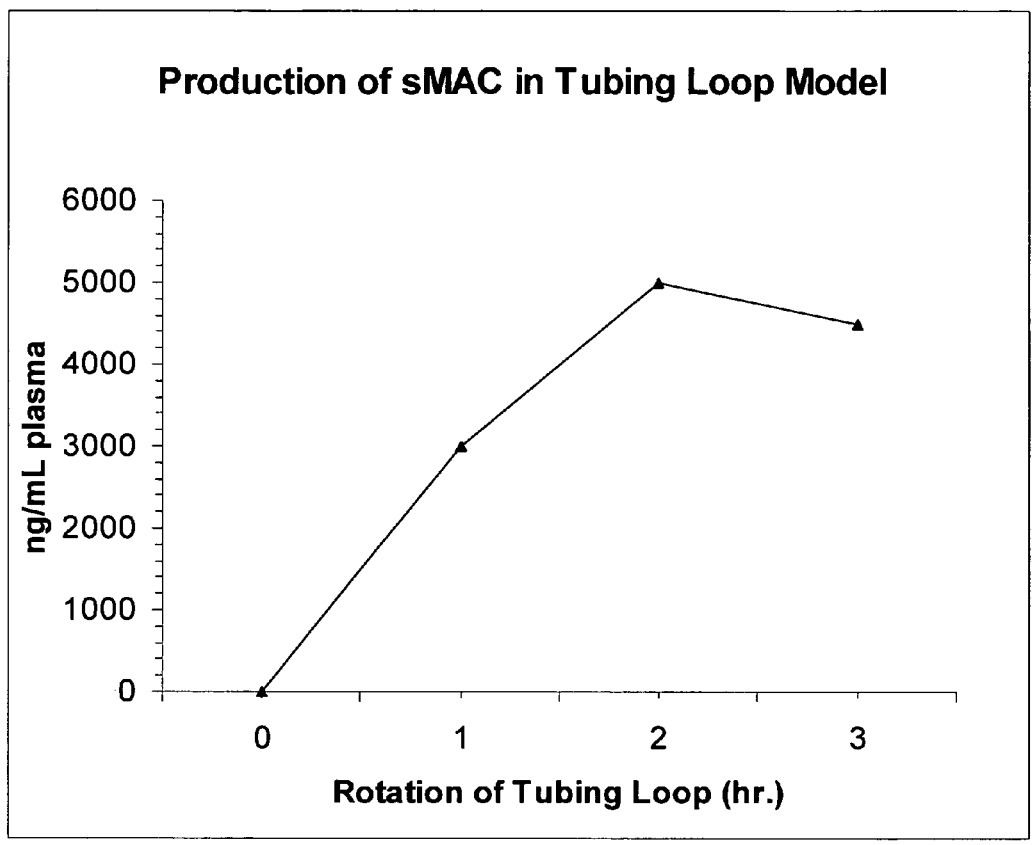
FIG. 6 depicts production of membrane attack complex in the tubing loop model.
Figure 7:
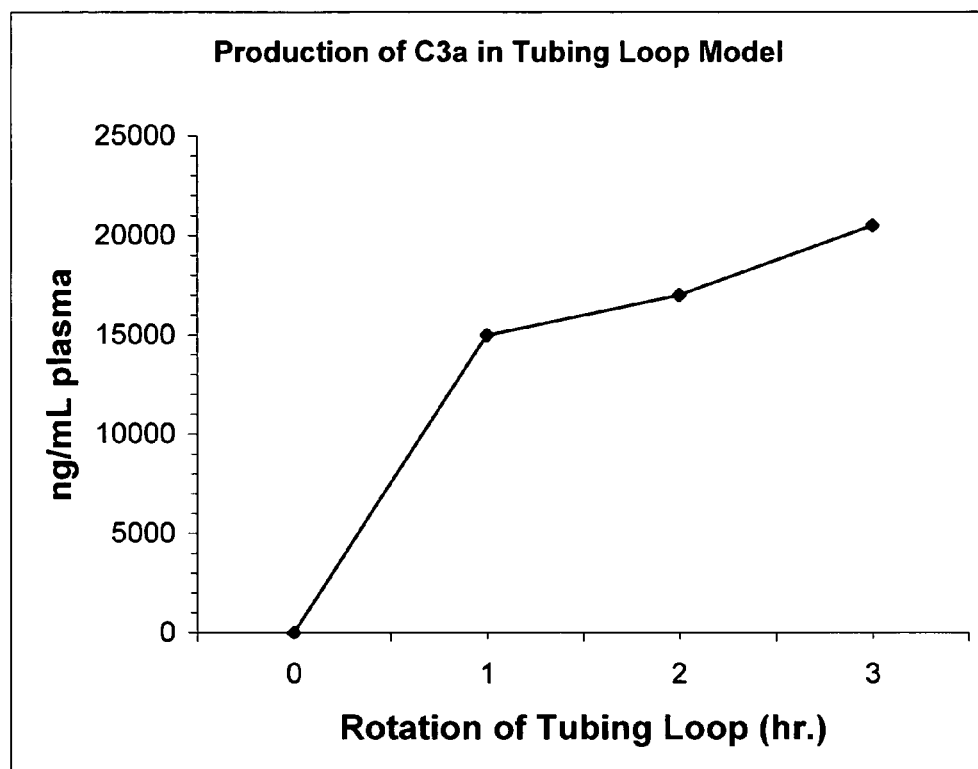
FIG. 7 depicts production of C3a in the tubing loop model.
Figure 8:
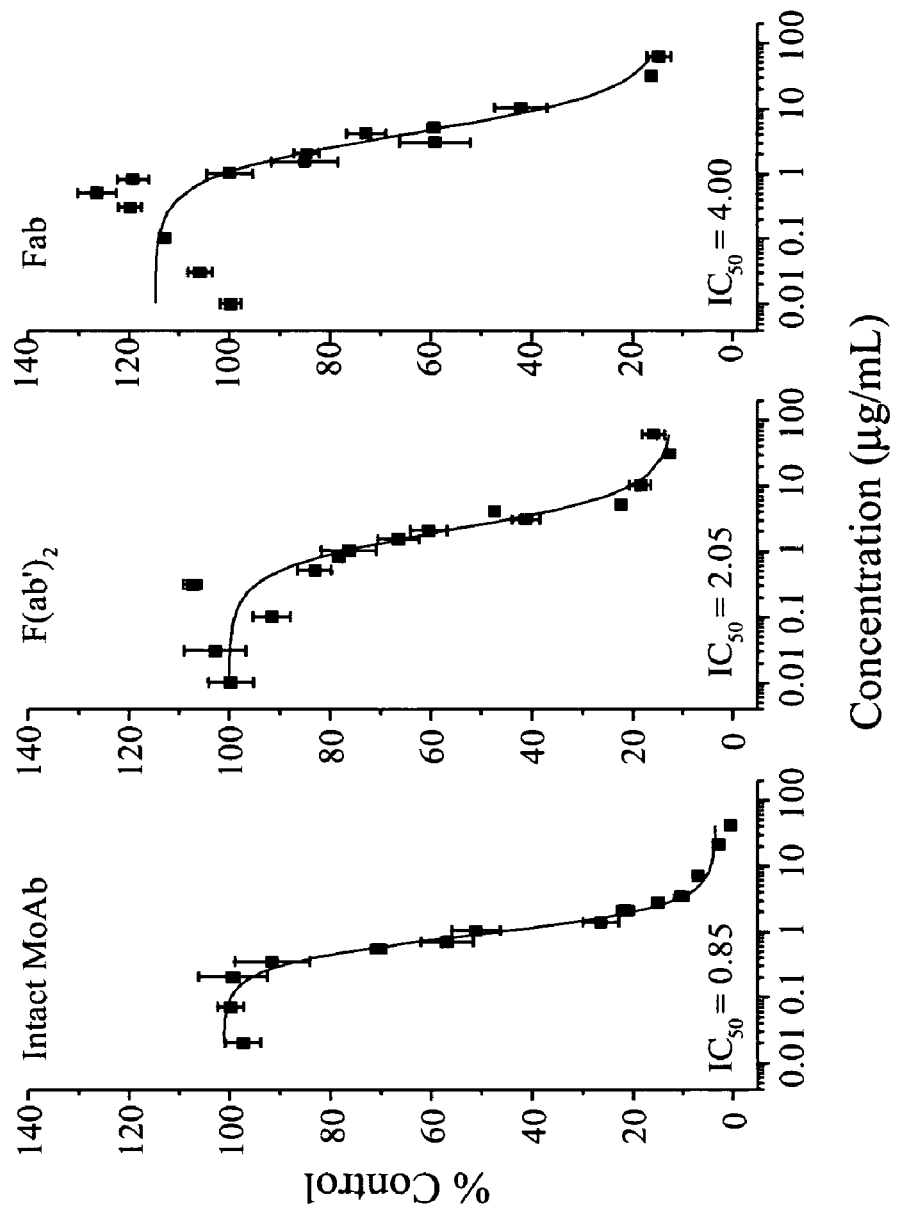
FIG. 8 depicts inhibition of C3a production by anti-properdin antibodies (intact antibody, F(ab')$_2$ fragment, and Fab fragment) in the tubing loop model.

The results are shown in FIGS. 6, 7, and 8. FIG. 6 illustrates the production of sMAC levels in the tubing loop model using blood diluted 1:1 in plasmalyte-148. This study demonstrates that sMAC levels increase rapidly and peak at 2 hours. FIG. 7 illustrates the production of C3a levels in the tubing loop model using blood diluted 1:1 in plasmalyte-148. This study demonstrates that C3a levels increase rapidly and peak at 3 hours. FIG. 8 demonstrates that anti-properdin antibodies effectively inhibit C3a production in the tubing loop model in a dose dependent manner. In the above study, a fully intact (clone 1.6.2.1.3), a F(ab')$_2$, and a Fab anti-properdin antibody was evaluated. All of the aforementioned antibodies provided near complete inhibition of C3a production at a concentration of 10 μg/ml of blood.

Example 4

The Effects of Anti-Properdin Monoclonal Antibodies on Complement in Blood Exposed to Extracorporeal Circulation Experimental Design A fully-human anti-properdin monoclonal F(ab')2 antibody fragment was generated to evaluate its ability to inhibit complement activation in a CPB model. More specifically, the study shown below was designed to evaluate the effects of the anti-properdin F(ab')2 antibody on the activation of complement in blood exposed to extracorporeal circulation via the use of pediatric cardiopulmonary bypass (CPB) units. Briefly, pediatric bypass circuits were assembled in a fashion that is consistent with their use during clinical practice. Two circuits were run simultaneously with freshly collected heparin-treated human blood, using a common roller pump, oxygenator and temperature regulator. The blood in one of the parallel circuits was treated with the F(ab')2 anti-properdin antibody, whereas the blood in the other circuit was treated with an isotype-matched antibody. At regular intervals during the simulated CPB procedure, blood samples were collected to allow for the measurement of complement activation products.

Test Method (1) Extracorporeal circuits were assembled using a hollow-fiber pediatric membrane oxygenator with an integrated heat exchanger module (D 901 Lilliput 1; Dideco, Mirandola, Italy), a pediatric venous reservoir with an integrated cardiotomy filter (D754 Venomidicard; Dideco), a perfusion tubing set (Sorin Biomedical, Inc., Irvine, Calif.) and a multiflow roller pump. To allow precise comparison of the effect of addition of test and control antibody to blood, each experiment consisted of simultaneously running both blood samples in parallel extracorporeal circuits using the same multiflow roller pump.

(2) On the day of the experiment, fresh whole human blood (2 volumes of ~225 mL each) were drawn into transfer packs containing porcine heparin (1125 units). Prior to participation, volunteers were required to meet the following entrance criteria:

Inclusion Criteria:
1. Males
2. Rated Class 1 (normal, healthy) under the American Society of Anesthesiologists (ASA) guidelines
3. Between the ages of 18 and 65 years old
4. Weigh at least 110 pounds Exclusion Criteria:
1. Donated blood in the past eight weeks
2. Currently taking drugs that could inhibit platelet aggregation
3. Pre-draw abnormal blood pressure, pulse rate, temperature, or hematocrit (3). The anti-properdin F(ab')2 antibody or isotype-matched antibody control agent were added to the transfer packs following collection. Transfer packs were weighed in order to determine the exact amount of blood used in each circuit. The total amount of heparin used should be 5 units per mL of blood (4). Prior to the addition of blood to the extracorporeal circuit, two 1.5-mL samples of blood were removed from the transfer pack and mixed with an equal volume of plasmalyte-148. This diluted blood sample is treated as described in step 7 below. This sample represents t=0 min.

(5). The CPB circuits were primed with 450 mL of plasmalyte-148 at 32° C. and circulated at 500 mL/min while the sweep gas flow was maintained at 0.25 liters per min using 100% oxygen. The sweep gas was changed to a mixture of oxygen (95%) and carbon dioxide (5%) after the blood was added to the circuit. Once the system was primed, 200 mL of blood was added to the reservoir via the prime port. Following the addition of the blood, 250-mL of prime fluid (plasmalyte-148) was simultaneously withdrawn distal to the oxygenator outlet to yield a final circuit volume of 400 mL. The pH, $pCO_2$, $PO^2$ and perfusate temperature were continuously recorded throughout the recirculation period. Blood was circulated with the prime fluid to allow complete mixing for 3-min. After the 3 minutes, a 3-mL aliquot of circulated blood:plasmalyte-148 (1:1) was collected from the circuit (t=3 min). (Note, the final heparin concentration, after dilution with the prime fluid is 2.5 units of heparin/mL of diluted blood).

(6). To mimic the procedures of surgical operation under hypothermia, the following protocol is followed for cooling and re-warming of blood. Following the mixing of the blood and plasmalyte-148, the blood was: a) cooled to 27° C. over a 5 min period; b) circulated through the CPB circuit for 60 min; c) rewarmed to 37° C. over a 30 mm period.

(7). Two 1.5-mL blood samples were collected at various time intervals from each CPB circuit (3, 8, 15, 30, 40, 50, 60, 68, 80, 90, and 98 minutes, as well as a terminal sample). The timetable shown in Table 2 was observed:

TABLE 2

| Time | Event |
| --- | --- |
| Pre-run | Prime circuits with 200 mL plasmalyte-148 |
| | Draw Blood |
| | Collect samples |
| 0 min | Add 200 mL blood to circuit |
| | Run circuit for 3 min to mix |
| 3 min | Collect samples |
| | Initiate cooling to 27° C. for 5 min |
| 8 min | Collect samples |
| | Run circuit for 60 min |
| 15 min | Collect samples |
| 30 min | Collect samples |
| 40 min | Collect samples |
| 50 min | Collect samples |
| 60 min | Collect samples |
| 68 min | Collect samples |
| | Initiate warming to 37° C. for 30 min |
| 80 min | Collect samples |
| 90 min | Collect samples |
| 98 min | Collect samples |
| | Terminate circulation |

(8). Immediately upon collection of the blood samples, the two samples were individually centrifuged at 2000×g at 4° C. to separate the plasma.

(9). The resultant plasma samples were frozen on dry ice and stored at −80° C. for subsequent analysis in the complement activation assays.

Results

Figure 9:
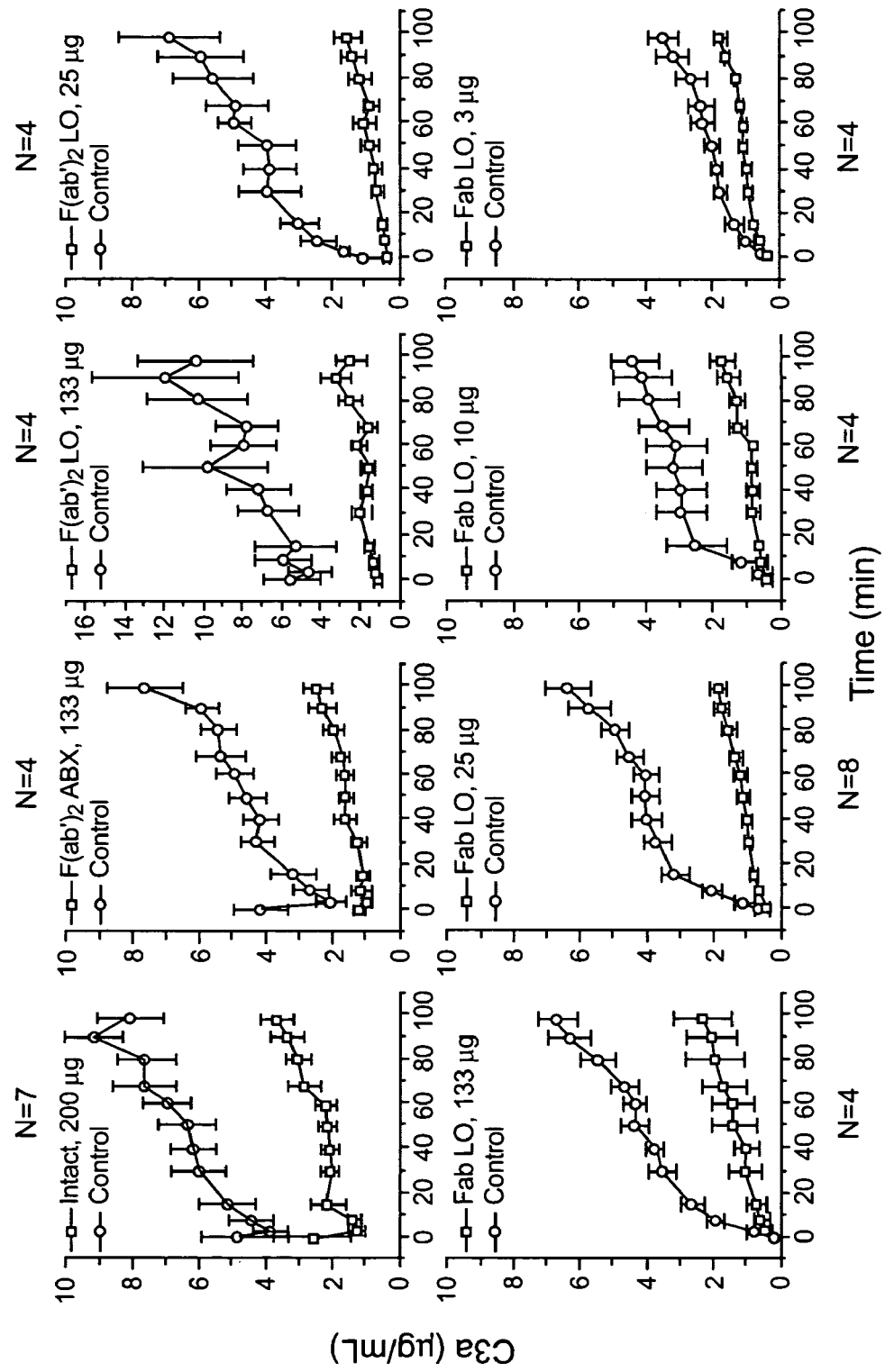
FIG. 9 depicts inhibition of membrane attack complex by anti-properdin antibodies (intact antibody, F(ab')$_2$ fragment, and Fab fragment) in an ex vivo cardiopulmonary bypass model.
Figure 10:
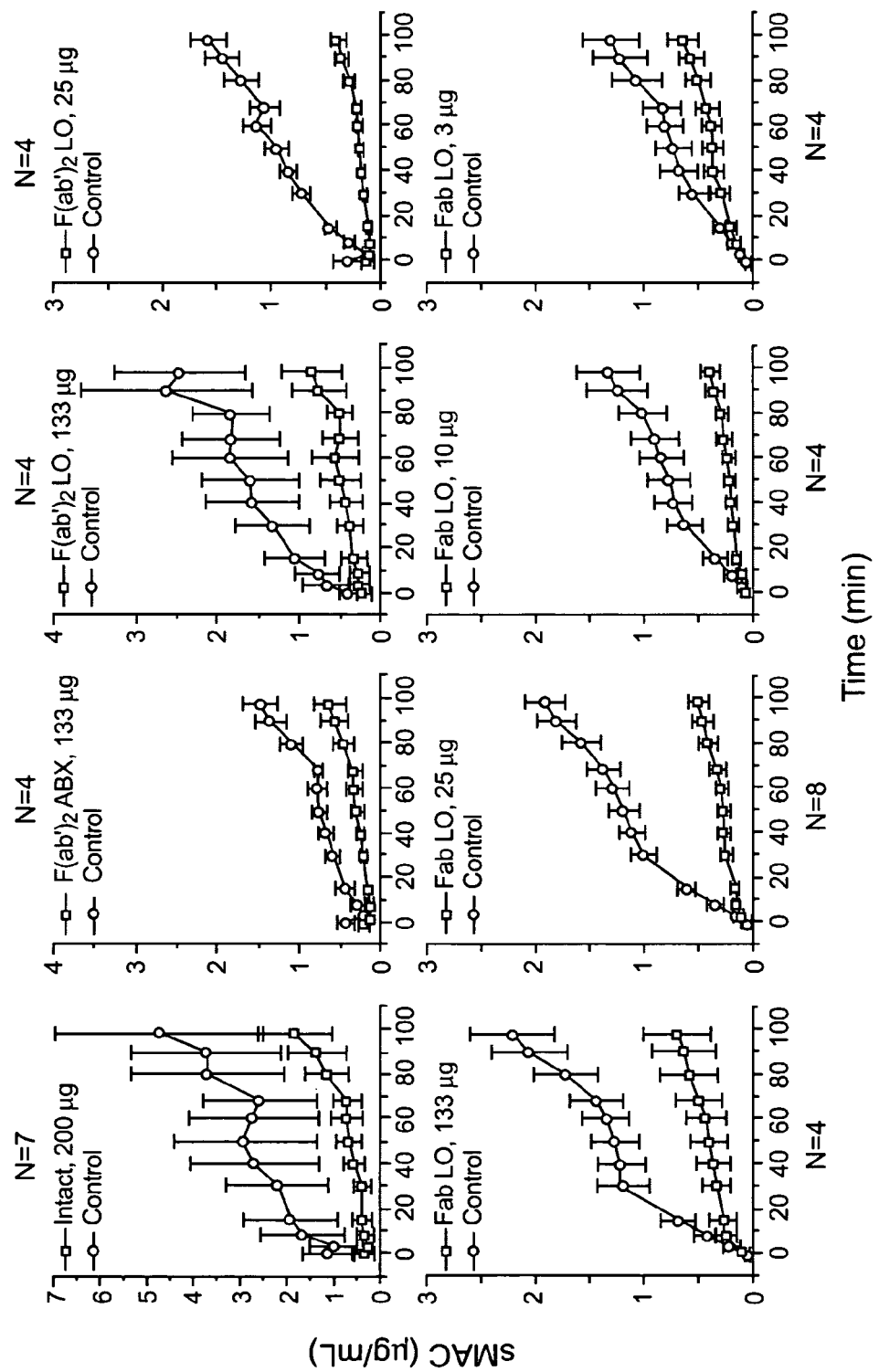
FIG. 10 depicts inhibition of MAC production by anti-properdin antibodies (intact antibody, F(ab')$_2$ fragment, and Fab fragment) in an ex vivo cardiopulmonary bypass model.
Figure 11:
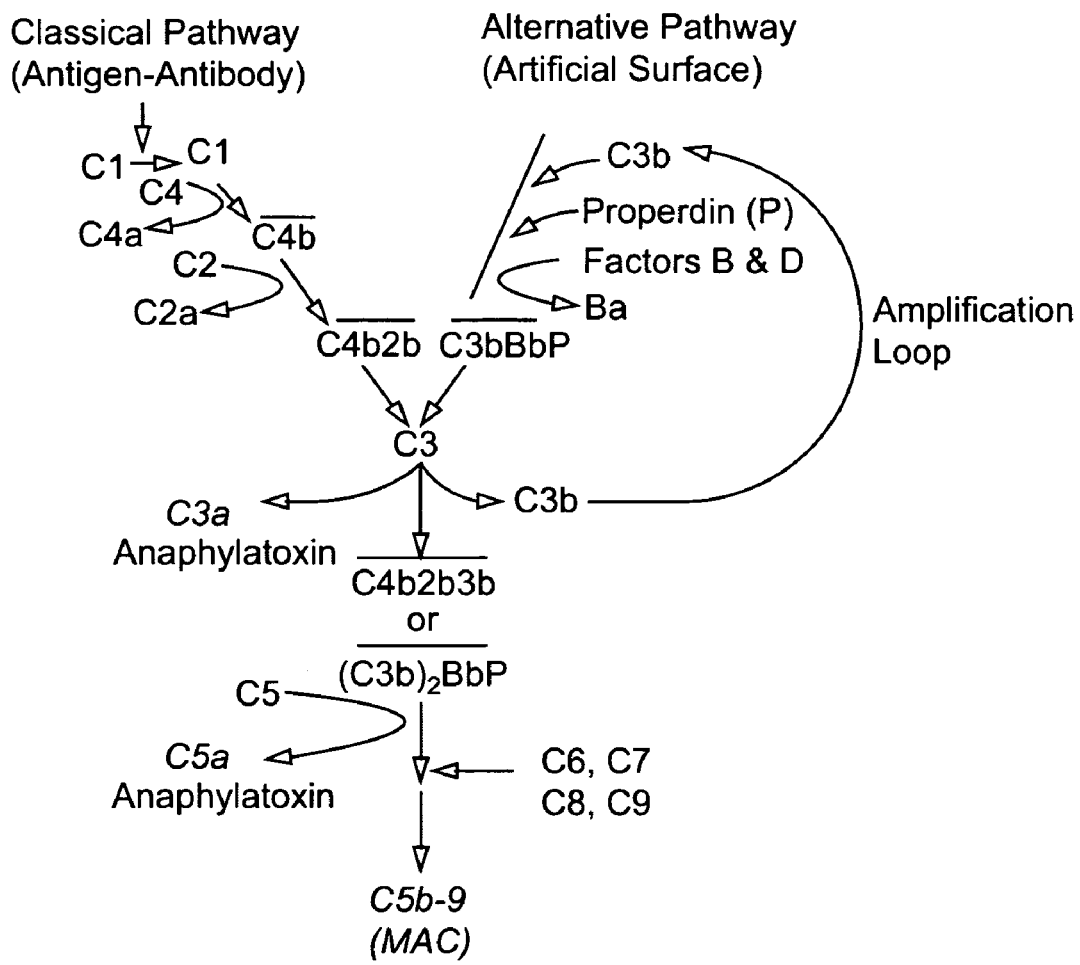
FIG. 11 depicts schematically two pathways to complement activation.

The results are shown in FIGS. 9 and 10.

FIG. 9 illustrates the effects of anti-properdin antibodies in an ex vivo CPB model. More specifically, a fully intact (clone 1.6.2.1.3), a F(ab)'$_2$, and Fab anti-properdin antibody was evaluated at various concentrations to determine efficacy in inhibiting complement activation. These results represent the average C3a values from several individuals for each respective cohort as indicated in the figure. The standard deviations are represented as vertical bars. A pronounced activation of complement is evident in the above study as measured by C3a levels in the control samples. A significant inhibition of C3a levels was observed when a fully intact anti-properdin antibody was used (dosage of 200 μg/ml of blood), as well as when a molar equivalent dose of F(ab)'$_2$ at 133 μg/ml of blood was evaluated. It is also important to note that an equivalent level of inhibition was observed with the F(ab)'$_2$ antibody at a dose of 25 μg/ml. Lastly, this study also demonstrates that an anti-properdin Fab antibody effectively inhibited C3a production in the above model. Surprisingly, the Fab antibody demonstrated efficacy at a dosage as low as 3 μg/ml of blood.

FIG. 10 illustrates the effects of anti-properdin antibodies in an ex-vivo CPB model. More specifically, a fully intact (clone 1.6.2.1.3), a F(ab)'$_2$, and Fab anti-properdin antibody was evaluated at various concentrations to determine efficacy in inhibiting complement activation. These results represent the average C3a values from several individuals for each respective cohort as indicated in the figure. The standard deviations are represented as vertical bars. A pronounced activation of complement is evident in the above study as measured by sMAC levels in the control samples. A significant inhibition of sMAC levels was observed when a fully intact anti-properdin antibody was used (dosage of 200 μg/ml of blood), as well as when a molar equivalent dose of F(ab)'$_2$ at 133 μg/ml of blood was evaluated. These results are consistent with the findings observed measuring C3a levels. It is also important to note that an equivalent level of inhibition was observed with the F(ab)'$_2$ antibody at a dose of 25 μg/ml. Lastly, this study also demonstrates that an anti-properdin Fab antibody effectively inhibited sMAC production in the above model. Surprisingly, the Fab antibody demonstrated efficacy at a dosage as low as 3 μg/ml of blood.

High resolution Biacore analysis was conducted on anti-properdin antibodies using human properdin. Affinity measurements were recorded for intact, Fab, and F(ab)'$_2$ anti-properdin antibodies. The data are presented in Table 3, below.

TABLE 3

| 25° C. | ka ($M^{-1}s^{-1}$) | | | kd ($s^{-1}$) | | | Kd (pM) | | |
|---|---|---|---|---|---|---|---|---|---|
| | AVG | SD | 95% C.I. | AVG | SD | 95% C.I. | AVG | SD | 95% C.I. |
| Intact Ab | 3.40E+04 | 20489.3 | 50868.21 | 9.75E-07 | 1.01E-06 | 2.515E-06 | 41.33 | 56.92 | 141.32 |
| Fab | 5.64E+04 | 17902.82 | 44445.68 | 9.73E-08 | 4.20E-08 | 1.043E-07 | 1.67 | 0.208 | 0.517 |
| F(ab)'$_2$ | 5.29E+04 | 7526.772 | 18686.02 | 8.23E-07 | 2.80E-07 | 6.953E-07 | 15.83 | 7.42 | 18.43 |

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

---

What is claimed is:

1. An isolated human antibody or antigen binding fragment thereof that specifically binds properdin, wherein said antibody inhibits oligomerization of a properdin monomer.

2. The antibody of claim 1, wherein said antibody is a monoclonal antibody.

3. The antibody of claim 1, wherein said antibody comprises a constant region comprising an amino acid sequence that is at least about 85% identical to a constant region amino acid sequence of a naturally occurring human antibody.

4. The antibody of claim 1, wherein said antibody comprises a framework region comprising an amino acid sequence that is at least about 85% identical to a framework region amino acid sequence of a naturally-occurring human antibody.

5. The antibody of claim 1, wherein said antibody is a single chain antibody.

6. The antibody of claim 1, wherein said antigen binding fragment is a Fab fragment.

7. The antibody of claim 1, wherein said antigen binding fragment is a F(ab)'$_2$ fragment.

8. The antibody of claim 1, wherein said antibody comprises a detectable label.

9. The antibody of claim 8, wherein the detectable label is selected from an enzyme, a fluorescent label, and a bioluminescent label.

10. An isolated human antibody or antigen binding fragment thereof that specifically binds properdin, wherein the antibody specifically binds an epitope within a thrombospondin type 1 repeat of properdin.

11. The antibody of claim 10, wherein properdin is human properdin.

12. The antibody of claim 10, wherein said antibody inhibits binding of properdin to complement component C3b.

13. A composition comprising the antibody of claim 10.

14. The composition of claim 13, wherein said composition comprises a pharmaceutically acceptable excipient.

15. An isolated human antibody or antigen binding fragment thereof that specifically binds properdin, wherein said antibody comprises a light chain variable region comprising an amino acid sequence selected from the group consisting of SEQ ID NO: 2, SEQ ID NO: 6, SEQ ID NO: 10, SEQ ID NO: 14 and SEQ ID NO: 18.

16. An isolated human antibody or antigen binding fragment thereof that specifically binds properdin, wherein said antibody comprises a heavy chain variable region comprising an amino acid sequence selected from the group consisting of SEQ ID NO: 4, SEQ ID NO: 8, SEQ ID NO: 12, SEQ ID NO: 16 and SEQ ID NO: 20.

17. The antibody of claim 15, wherein said antibody comprises a light chain variable region comprising an amino acid sequence as set forth in SEQ ID NO: 2 and a heavy chain variable region comprising an amino acid sequence as set forth in SEQ ID NO: 4.

18. The antibody of claim 15, wherein said antibody comprises a light chain variable region comprising an amino acid sequence as set forth in SEQ ID NO: 6 and a heavy chain variable region comprising an amino acid sequence as set forth in SEQ ID NO: 8.

19. The antibody of claim 15, wherein said antibody comprises a light chain variable region comprising an amino acid sequence as set forth in SEQ ID NO: 10 and a heavy chain variable region comprising an amino acid sequence as set forth in SEQ ID NO: 12.

20. The antibody of claim 15, wherein said antibody comprises a light chain variable region comprising an amino acid sequence as set forth in SEQ ID NO: 14 and a heavy chain variable region comprising an amino acid sequence as set forth in SEQ ID NO: 16.

21. The antibody of claim 15, wherein said antibody comprises a light chain variable region comprising an amino acid sequence as set forth in SEQ ID NO: 18 and a heavy chain variable region comprising an amino acid sequence as set forth in SEQ ID NO: 20.

22. The antibody of claim 10, wherein said antibody reduces the level and/or production of a component of the alternative complement pathway, or a factor produced by action of a component of the alternative complement pathway.

23. The antibody of claim 10, wherein said antibody reduces formation of membrane attack complex (MAC).

24. The antibody of claim 10, wherein said antibody reduces formation of an anaphylatoxin.

25. The antibody of claim 24, wherein said anaphylatoxin is C3a or C5a.

26. The antibody of claim 10, wherein said antibody reduces formation of C3c.

27. The antibody of claim 10, wherein said antibody is a monoclonal antibody.

28. The antibody of claim 10, wherein said antibody is a single chain antibody.

29. The antibody of claim 10, wherein said antigen binding fragment is a Fab fragment.

30. The antibody of claim 10, wherein said antigen binding fragment is a F(ab)'$_2$ fragment.

31. The antibody of claim 10, wherein said antibody comprises a detectable label.

32. The antibody of claim 31, wherein the detectable label is selected from an enzyme, a fluorescent label, and a bioluminescent label.

33. The antibody of claim 1, wherein the properdin is human properdin.

34. The antibody of claim 10, wherein said thrombospondin type 1 repeat of properdin is selected from the group consisting of TSR1, TSR2, TSR3, TSR4, TSR5 and TSR6.

* * * * *

UNITED STATES PATENT AND TRADEMARK OFFICE
CERTIFICATE OF CORRECTION

PATENT NO. : 7,423,128 B2
APPLICATION NO. : 10981300
DATED : September 9, 2008
INVENTOR(S) : Gazit-Bornstein et al.

It is certified that error appears in the above-identified patent and that said Letters Patent is hereby corrected as shown below:

| Issued Patent | | 1. Description of Error |
|---|---|---|
| Column | Line | |
| 1 | 67 | Change "sCR1molecule" to --sCR1 molecule--. |
| 12 | 61-62 | Change "XenoMouseg:" to --XenoMouse®:--. |
| 15 | 8 (Approx.) | Change "25-kDa)" to --25 kDa)--. |
| 18 | 14 | Change "B 1," to --B1,--. |
| 21 | 2 | Change "IgG$_1$" to --IgG1--. |
| 22 | 66 | Change "sythesized" to --synthesized--. |
| 27 | 28 | Change "XenoMouseg" to --XenoMouse®--. |
| 27 | 64 | Change "3 ed." to --3$^{rd}$ ed.--. |
| 29 | 53-54 | Change "anticholenergics" to --anticholinergics--. |
| 30 | 47 | Change "references:" to --references.--. |
| 33 | 1-10 | Delete "Following a 1…..ELISA plate reader." and insert the same in Col. 32, Line 67, after "solution." as a continuation of same paragraph. |
| 33 | 18 | Change "Coming" to --Corning--. |
| 34 | 11 | Change "1.7,1.11," to --1.7, 1.11,--. |
| 35 | 19 | Change "Nonoclonal" to --Monoclonal--. |
| 37 | 67 | After "hematocrit" insert --.--. |
| 38 | 6 | After "blood" insert --.--. |
| 38 | 22 | Change "PO$^{2}$" to --pO$_2$--. |
| 38 | 35 | Change "mm" to --min--. |
| 86 | 54 | In Claim 9, before "and" insert --a luminescent label,--. |

UNITED STATES PATENT AND TRADEMARK OFFICE
CERTIFICATE OF CORRECTION

PATENT NO. : 7,423,128 B2
APPLICATION NO. : 10981300
DATED : September 9, 2008
INVENTOR(S) : Gazit-Bornstein et al.

It is certified that error appears in the above-identified patent and that said Letters Patent is hereby corrected as shown below:

| Issued Patent | | 1. Description of Error |
| --- | --- | --- |
| Column | Line | |
| 86 | 58-59 | In Claim 10, change "tbrombospondin" to --thrombospondin--. |

Signed and Sealed this

Twenty-fourth Day of February, 2009

JOHN DOLL
*Acting Director of the United States Patent and Trademark Office*